United States Patent
Hwang et al.

(10) Patent No.: US 11,122,258 B2
(45) Date of Patent: Sep. 14, 2021

(54) METHOD AND APPARATUS FOR GENERATING AND DISPLAYING 360-DEGREE VIDEO BASED ON EYE TRACKING AND PHYSIOLOGICAL MEASUREMENTS

(71) Applicant: PCMS Holdings, Inc., Wilmington, DE (US)

(72) Inventors: Sungjae Hwang, Gyeonggi-do (KR); Jongho Kim, Seoul (KR)

(73) Assignee: PCMS Holdings, Inc., Wilmington, DE (US)

(*) Notice: Subject to any disclaimer, the term of this patent is extended or adjusted under 35 U.S.C. 154(b) by 0 days.

(21) Appl. No.: 16/626,214

(22) PCT Filed: Jun. 22, 2018

(86) PCT No.: PCT/US2018/039086
§ 371 (c)(1),
(2) Date: Dec. 23, 2019

(87) PCT Pub. No.: WO2019/005622
PCT Pub. Date: Jan. 3, 2019

(65) Prior Publication Data
US 2020/0128232 A1   Apr. 23, 2020

Related U.S. Application Data

(60) Provisional application No. 62/527,752, filed on Jun. 30, 2017.

(51) Int. Cl.
*H04N 13/383*    (2018.01)
*H04N 13/117*    (2018.01)
(Continued)

(52) U.S. Cl.
CPC ....... *H04N 13/383* (2018.05); *G02B 27/0093* (2013.01); *G02B 27/0172* (2013.01);
(Continued)

(58) Field of Classification Search
CPC .. H04N 13/117; H04N 13/344; H04N 13/383; G02B 2027/014;
(Continued)

(56) References Cited

U.S. PATENT DOCUMENTS

| 5,422,653 A | 6/1995 | Maguire, Jr. |
| 6,798,443 B1 | 9/2004 | Maguire, Jr. |

(Continued)

FOREIGN PATENT DOCUMENTS

| EP | 1445938 A1 | 8/2004 |
| WO | 2016102763 | 6/2016 |

OTHER PUBLICATIONS

Avidan, Shai, et al., "Seam Carving for Content-Aware Image Resizing". ACM Transactions on Graphics (TOG), vol. 26, Issue 3, Jul. 2007, ISSN: 0730-0301, 9 pages.

(Continued)

*Primary Examiner* — Afroza Chowdhury
(74) *Attorney, Agent, or Firm* — Invention Mine LLC

(57) ABSTRACT

Some embodiments of a method may include: identifying an object of interest in a multi-view video based on a point of view and physiological data of a camera operator; displaying the multi-view video; and displaying a visual effect associated with the object of interest. Some embodiments of a method may include: capturing a multi-view video with a camera; tracking a point of view of a camera operator controlling the camera; measuring physiological data of the camera operator; identifying an object of interest in the multi-view video based on the point of view and the physi- (Continued)

ological data; and storing the multi-view video and information indicating the object of interest identified.

20 Claims, 40 Drawing Sheets

(51) Int. Cl.
    *G02B 27/00*     (2006.01)
    *G02B 27/01*     (2006.01)
    *G06T 7/73*     (2017.01)
    *G06F 3/01*     (2006.01)
    *H04N 13/344*     (2018.01)

(52) U.S. Cl.
    CPC ............... *G06F 3/016* (2013.01); *G06T 7/74* (2017.01); *H04N 13/117* (2018.05); *H04N 13/344* (2018.05); *G02B 2027/014* (2013.01); *G02B 2027/0178* (2013.01); *G02B 2027/0181* (2013.01)

(58) Field of Classification Search
    CPC .... G02B 2027/0178; G02B 2027/0181; G02B 27/0093; G02B 27/0172; G06F 3/016; G06T 7/74
    See application file for complete search history.

(56) References Cited

U.S. PATENT DOCUMENTS

| | | | |
|---|---|---|---|
| 7,206,022 B2 | 4/2007 | Miller | |
| 8,510,166 B2 | 8/2013 | Neven | |
| 8,670,183 B2 | 3/2014 | Clavin | |
| 8,704,879 B1 | 4/2014 | Cheng | |
| 8,994,613 B1 | 3/2015 | Johnson | |
| 9,392,212 B1 | 7/2016 | Ross | |
| 10,007,350 B1* | 6/2018 | Holz | G06T 7/246 |
| 2004/0101178 A1* | 5/2004 | Fedorovskaya | H04N 1/32 382/128 |
| 2008/0024594 A1 | 1/2008 | Ritchey | |
| 2012/0113209 A1* | 5/2012 | Ritchey | G06F 3/015 348/14.02 |
| 2013/0258089 A1 | 10/2013 | Lyons | |
| 2014/0063055 A1* | 3/2014 | Osterhout | G06F 3/165 345/633 |
| 2015/0003819 A1 | 1/2015 | Ackerman | |
| 2015/0022627 A1 | 1/2015 | Sato | |
| 2016/0085302 A1 | 3/2016 | Publicover | |
| 2016/0179201 A1 | 6/2016 | Anderson | |
| 2017/0109936 A1 | 4/2017 | Powderly | |

OTHER PUBLICATIONS

Vockeroth, Johannes, et al., "The Combination of a Mobile Gaze-Driven and a Head-Mounted Camera in a Hybrid Perspective Setup". IEEE International Conference on Systems, Man and Cybernetics, (2007), 6 pages.

S. Highton, "The 360° Video Conundrum—Cinematic VR Considerations," Virtual Reality Photography, Jan. 2015, http://www.vrphotography.com/360videovr/.

Christoforou, Christoforos, et al. "From the Eyes and the Heart: A Novel Eye-Gaze Metric That Predicts Video Preferences of a Large Audience". Frontiers in Psychology, vol. 6, Art 579, May 2015, pp. 1-11.

International Search Report and Written Opinion of the International Searching Authority for PCT/US2018/039086 dated Sep. 18, 2018.

Miller, Gregor, et. al., "MediaDiver: Viewing and Annotating Multi-View Video". CH 2011—Interactivity 2 Open, May 7, 2011, 6 pages.

Manpreet, Kaur, et. al., "ROI Based Medical Image Compression for Telemedicine Application". Fourth International Conference on Eco-Friendly Computing and Communication Systems, ICECCS, (2015), pp. 579-585.

International Preliminary Report on Patentability for PCT/US2018/039086 dated Dec. 31, 2019, 12 pages.

Gutwin, Carl, et al., "A Descriptive Framework of Workspace Awareness for Real-Time Groupware", Computer Supporter Cooperative Work, vol. 11, No. 3-4, Sep. 1, 2002, pp. 411-446. 36 pages.

* cited by examiner

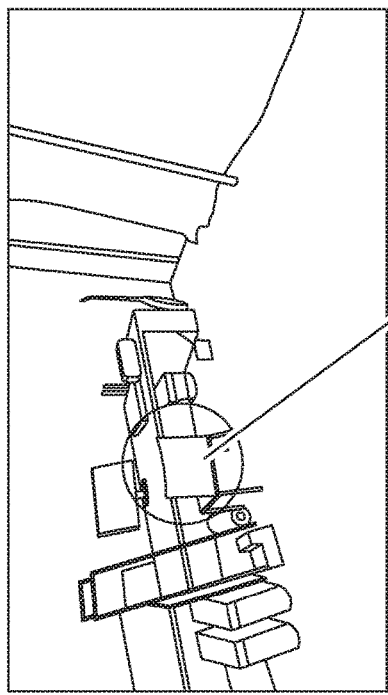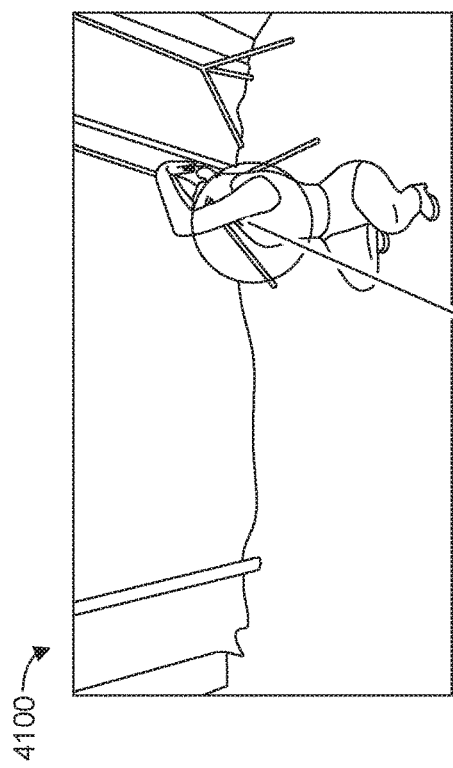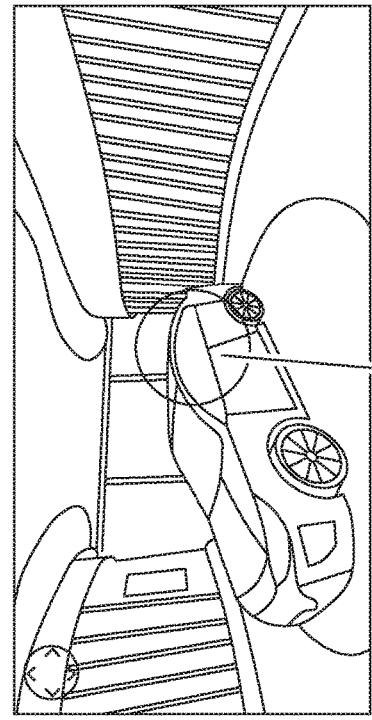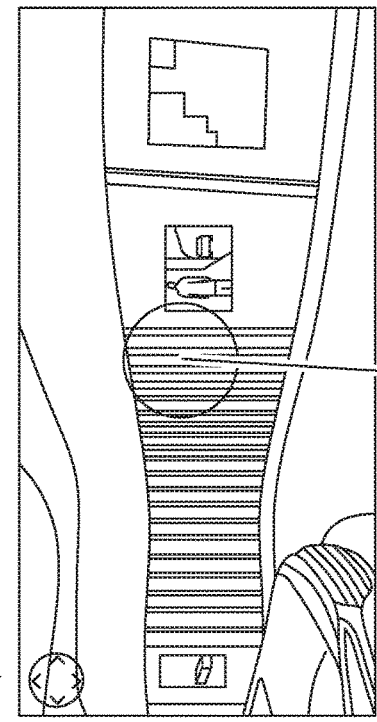
FIG. 41
FIG. 42

4400

DISPLAYING A PORTION OF A MULTI-VIEW VIDEO ON A VIEWABLE DISPLAY OF A HEAD-MOUNTED DEVICE (HMD) WORN BY A USER, WHEREIN THE VIEWABLE DISPLAY OF THE HMD DEFINES A POINT OF VIEW OF THE USER WITH RESPECT TO THE MULTI-VIEW VIDEO
4402

RECEIVING INFORMATION REGARDING A POINT OF VIEW OF A CAMERA OPERATOR OTHER THAN THE USER AND AN OBJECT OF INTEREST IN THE MULTI-VIEW VIDEO, THE POINT OF VIEW OF THE CAMERA OPERATOR BEING WITH RESPECT TO THE MULTI-VIEW VIDEO, AND THE OBJECT OF INTEREST IS IDENTIFIED AS BEING WITHIN THE POINT OF VIEW OF THE CAMERA OPERATOR AND IS INDICATED AS BEING OF INTEREST TO THE CAMERA OPERATOR 4404

RESPONSIVE TO DETERMINING THAT THE POINT OF VIEW OF THE USER AS DEFINED BY THE VIEWABLE DISPLAY OF THE HMD OVERLAPS WITH THE POINT OF VIEW OF THE CAMERA OPERATOR, RENDERING THE OBJECT OF INTEREST IN THE PORTION OF THE MULTI-VIEW VIDEO DISPLAYED TO THE USER AND WITHIN THE POINT OF VIEW OF THE USER
4406

DETERMINING THAT THE POINT OF VIEW OF THE USER AS DEFINED BY THE VIEWABLE DISPLAY OF THE HMD NO LONGER OVERLAPS WITH THE POINT OF VIEW OF THE CAMERA OPERATOR
4408

RESPONSIVELY IMPLEMENTING A DISPLAY EFFECT TO CONTINUE RENDERING THE OBJECT OF INTEREST WITHIN THE POINT OF VIEW OF THE USER EVEN AS THE POINT OF VIEW OF THE USER AS DEFINED BY THE VIEWABLE DISPLAY OF THE HMD NO LONGER OVERLAPS WITH THE POINT OF VIEW OF THE CAMERA OPERATOR
4410

FIG. 44

METHOD AND APPARATUS FOR GENERATING AND DISPLAYING 360-DEGREE VIDEO BASED ON EYE TRACKING AND PHYSIOLOGICAL MEASUREMENTS

CROSS-REFERENCE TO RELATED APPLICATIONS

The present application is a national stage application under 35 U.S.C. § 371 of International Application No. PCT/US2018/039086, entitled "METHOD AND APPARATUS FOR GENERATING AND DISPLAYING 360-DEGREE VIDEO BASED ON EYE TRACKING AND PHYSIOLOGICAL MEASUREMENTS," filed on Jun. 22, 2018, which claims benefit under 35 U.S.C. § 119(e) from U.S. Provisional Patent Application Ser. No. 62/527,752, entitled "Method and Apparatus for Generating and Displaying 360-Degree Video Based on Eye Tracking and Physiological Measurements," filed Jun. 30, 2017, the entirety of which is incorporated herein by reference.

BACKGROUND

Multi-view videos (for example, 360-degree videos), also known as immersive videos or spherical videos, are video recordings such that views in multiple directions are recorded at the same time, such as by using an omnidirectional camera or a collection of cameras. During playback, the viewer has control of the viewing direction, such as with a digital panorama photo.

Omnidirectional cameras and rigs have been developed for the purpose of filming multi-view (e.g., 360-degree) video, including rigs such as GoPro's Omni and Odyssey, the Nokia OZO, the Facebook Surround 360, the Kodak Pixpro SP360 4K Dual Pack Pro and the Axon's AZilPix Studio.One (all of which consist of multiple cameras installed into a single rig), the Vuze camera, handheld dual-lens cameras such as the Ricoh Theta S and Samsung Gear 360, and the Kogeto Dot 360—panoramic camera lens accessory developed for the iPhone 4, 4S, and Samsung Galaxy Nexus. In many videoconferencing systems, 360° cameras are used so that multiple (e.g., all) participants at one location may be recorded with one camera.

SUMMARY

Some embodiments of a method may include: capturing a multi-view video with a camera; tracking a point of view of a camera operator controlling the camera; measuring physiological data of the camera operator; identifying an object of interest in the multi-view video based on the point of view and the physiological data; and storing the multi-view video and information indicating the object of interest identified.

For some embodiments, a method may further include: displaying the multi-view video; and displaying a visual effect based on at least one of the point of view of the camera operator and the physiological data of the camera operator.

For some embodiments, a method may further include: rendering the multi-view video to emphasize the object of interest; and displaying the rendered multi-view video.

For some embodiments, rendering the multi-view video to emphasize the object of interest may include: identifying a first portion of the multi-view video with the object of interest; identifying a second portion of the multi-view video without the object of interest; reducing a data size of the second portion of the multi-view video; and rendering the first portion of the multi-view video and the reduced data size second portion of the multi-view video.

For some embodiments, a method may further include: matching the object of interest with an emotional state based on the physiological data; and displaying a visual effect for the object of interest based on the matched emotional state.

For some embodiments, a method may further include: determining a portion of the multi-view video containing the object of interest; selecting a portion of the physiological data associated with the portion of the multi-view video containing the object of interest; and displaying a visual effect based on the selected portion of the physiological data.

For some embodiments, a method may further include displaying a visual effect of the object of interest based on a comparison of a point of view of a viewer of the multi-view video with a point of view of the camera operator.

For some embodiments, a method may further include: comparing a point of view (POV) of the camera operator with a POV of a viewer of the multi-view video; and determining an amount of overlap between the POV of the camera operator and the POV of the viewer.

For some embodiments, physiological data may include measurements of at least one of a pupil size of the camera operator, a pulse rate of the camera operator, and a motion of the camera operator.

For some embodiments, a method may further include: displaying the multi-view video; determining a point of view (POV) overlap as an amount of area overlap between a POV of the camera operator and a POV of a viewer of the multi-view video; setting a visual effect intensity proportional to the POV overlap; and displaying a visual effect with an intensity equal to the visual effect intensity.

For some embodiments, a method may further include setting the visual effect based on an overall emotional state of the camera operator and a characteristic identified with the object of interest.

For some embodiments, a method may further include responsive to detecting the object of interest in the POV of the viewer, increasing the visual effect intensity.

For some embodiments, a method may further include: displaying the multi-view video to be synchronous with a head movement of a viewer of the multi-view video; and responsive to detecting an alignment of the POV of the viewer and the POV of the camera operator, displaying a visual effect for an emotional state associated with the object of interest.

For some embodiments, a method may further include: displaying the multi-view video to be synchronous with a head movement of a viewer of the multi-view video; and responsive to detecting a proximity between a point of view (POV) of the viewer and the POV of the camera operator, displaying a visual effect indicating the proximity between the POV of the viewer and the POV of the camera operator.

For some embodiments, identifying the object of interest in the multi-view video based on the point of view and the physiological data may include: identifying a plurality of objects in the multi-view video; determining, for each of the plurality of objects, a sustaining time equal to a length of time that the point of view of the camera operator points to the respective object; determining, for each of the plurality of objects, an object frequency equal to a frequency of times that the point of view of the camera operator points to the respective object; associating, for each of the plurality of objects, a portion of the physiological data to the respective object; and determining, for each of the plurality of objects, a level of interest based on the sustaining time, the object frequency, and the portion of the physiological data for the respective object.

For some embodiments, tracking the point of view of the camera operator may track the eye position of the camera operator.

For some embodiments, tracking the point of view of the camera operator may include: capturing an image of at least one eye of the camera operator; and determining the eye direction of the camera operator using the image of at least one eye of the camera operator.

For some embodiments, a method may further include: presenting an effect based on at least one of the point of view of the camera operator and the physiological data of the camera operator, wherein the effect may include at least one of a sonic effect and a haptic effect.

For some embodiments, the multi-view video may include a 360-degree video.

Some embodiments of an apparatus may include: a processor; and a non-transitory computer-readable medium storing instructions that are operative, when executed by the processor, to perform a method described above.

For some embodiments, an apparatus may further include: a gaze-tracking sensor; a camera; a physiological sensor; and a display.

For some embodiments, an apparatus may further include: a point of view comparison module; an emotion estimation module; an emotion tagging module; and a memory storage device.

Some embodiments of a method may include: identifying an object of interest in a multi-view video based on a point of view and physiological data of a camera operator; displaying the multi-view video; and displaying a visual effect associated with the object of interest.

Some embodiments of a method may include: capturing a multi-view video with a multi-view camera; tracking a view direction and a point of view of a camera operator controlling the camera using an eye tracker mounted on the camera; measuring physiological data of the camera operator; identifying an object of interest in the multi-view video based on the view direction and the physiological data, wherein the object of interest is within the point of view of the camera operator; displaying a portion of the multi-view video on a viewable display of a head-mounted device (HMD) worn by a user other than the camera operator, wherein the viewable display of the HMD defines a point of view of the user; rendering the identified object of interest in the portion of the multi-view video displayed to the user and within the point of view of the user when the point of the view of the user is determined to overlap with the point of view of the camera operator; and implementing a display effect to continue rendering the identified object of interest within the point of view of the user even when the point of the view user no longer overlaps with the point of view of the camera operator.

Some embodiments of an apparatus may include: a processor; and a non-transitory computer-readable medium storing instructions that are operative, when executed by the processor, to perform a method listed above.

For some embodiments, an apparatus may further include: a gaze-tracking sensor; a camera; a physiological sensor; and a display.

Some embodiments of a method may include: displaying a portion of a multi-view video on a viewable display of a head-mounted device (HMD) worn by a user, wherein the viewable display of the HMD defines a point of view of the user with respect to the multi-view video; receiving information regarding a point of view of a camera operator other than the user and an object of interest in the multi-view video, the point of view of the camera operator being with respect to the multi-view video, and the object of interest is identified as being within the point of view of the camera operator and is indicated as being of interest to the camera operator; responsive to determining that the point of view of the user as defined by the viewable display of the HMD overlaps with the point of view of the camera operator, rendering the object of interest in the portion of the multi-view video displayed to the user and within the point of view of the user; determining that the point of view of the user as defined by the viewable display of the HMD no longer overlaps with the point of view of the camera operator; and responsively implementing a display effect to continue rendering the object of interest within the point of view of the user even as the point of view of the user as defined by the viewable display of the HMD no longer overlaps with the point of view of the camera operator.

For some embodiments, a method may further include: measuring physiological data of the camera operator; and tracking eye position of the camera operator, wherein the object of interest may be identified as being within the point of view of the camera operator and may be indicated as being of interest to the camera operator based on the physiological data and the eye position of the camera operator.

Some embodiments of an apparatus may include: a processor; and a non-transitory computer-readable medium storing instructions that are operative, when executed by the processor, to perform a method listed above.

For some embodiments, an apparatus may further include: a gaze-tracking sensor; a camera; a physiological sensor; and a display.

BRIEF DESCRIPTION OF THE DRAWINGS

FIG. 41 is a process diagram illustrating an example for handling restricted viewpoints according to some embodiments.

FIG. 42 is a process diagram illustrating an example for adjusting a viewers starting viewpoint according to some embodiments.

FIG. 44 is a flowchart illustrating an example process for implementing a display effect based on the point of view of the camera operator and the viewer according to some embodiments.

Figure 1A:
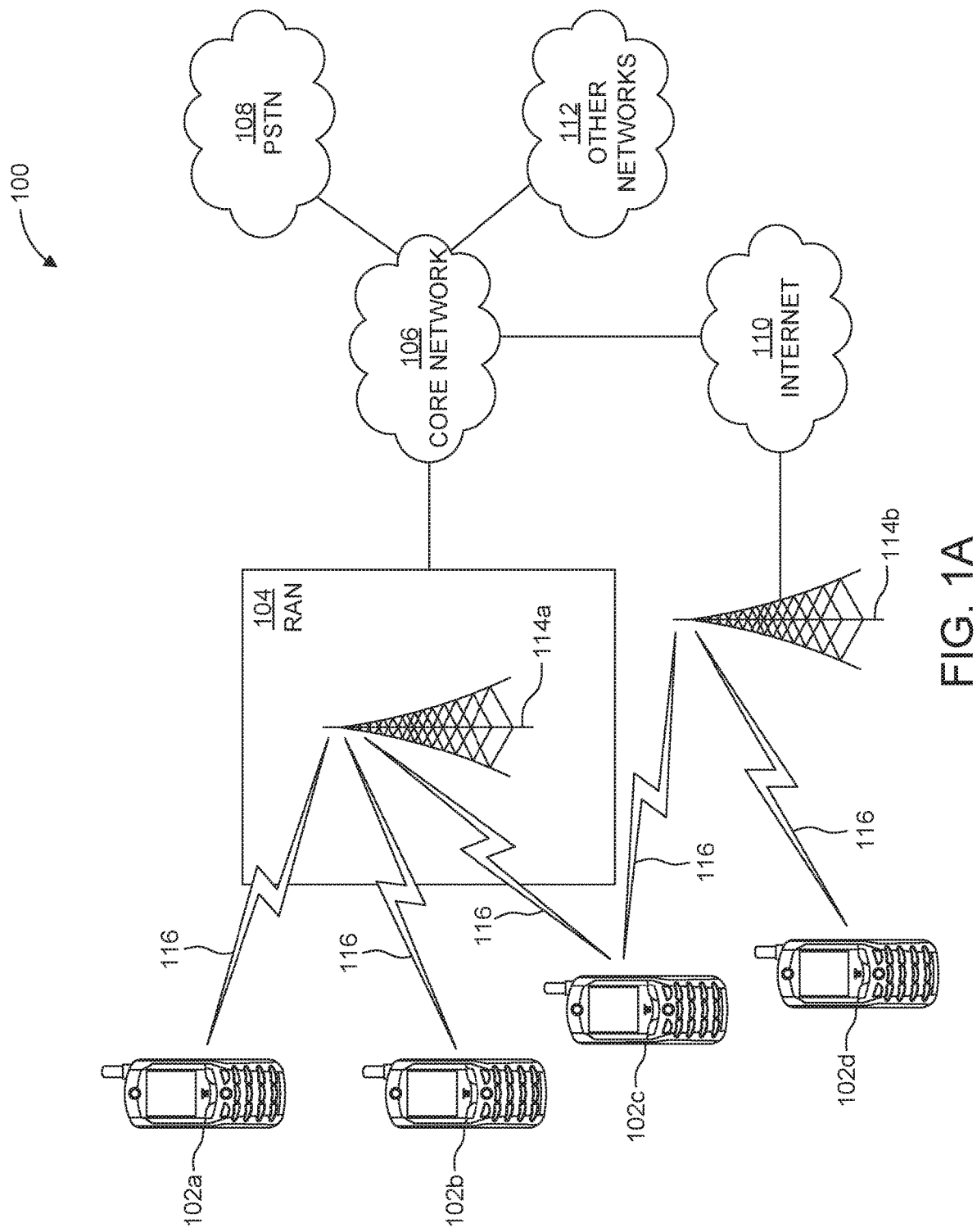
FIG. 1A is a system diagram of an example system illustrating an example communications system according to some embodiments.

It will be appreciated that elements in the figures are illustrated for simplicity and clarity and have not necessarily been drawn to scale. For example, the dimensions of some of the elements in the figures may be out of scale relative to other elements to help to improve understanding of methods and systems described herein in accordance with some embodiments.

The apparatus and method components have been represented where appropriate by conventional symbols in the drawings, showing only those specific details that are pertinent to understanding the of methods and systems described herein in accordance with some embodiments.

The entities, connections, arrangements, and the like that are depicted in—and described in connection with—the various figures are presented by way of example and not by way of limitation. As such, any and all statements or other indications as to what a particular figure "depicts," what a particular element or entity in a particular figure "is" or "has," and any and all similar statements—that may in isolation and out of context be read as absolute and therefore limiting—may only properly be read as being constructively preceded by a clause such as "In at least one embodiment, . . . ." For brevity and clarity of presentation, this implied leading clause is not repeated ad nauseum in the detailed description of the drawings.

DETAILED DESCRIPTION

A wireless transmit/receive unit (WTRU) may be used as a head-mounted display (HMD) and/or an augmented reality (AR)/virtual reality (VR)/mixed reality (MR) device, for example, in embodiments described herein.

FIG. 1A is a diagram illustrating an example communications system 100 in which one or more disclosed embodiments may be implemented. The communications system 100 may be a multiple access system that provides content, such as voice, data, video, messaging, broadcast, etc., to multiple wireless users. The communications system 100 may enable multiple wireless users to access such content through the sharing of system resources, including wireless bandwidth. For example, the communications systems 100 may employ one or more channel access methods, such as code division multiple access (CDMA), time division multiple access (TDMA), frequency division multiple access (FDMA), orthogonal FDMA (OFDMA), single-carrier FDMA (SC-FDMA), zero-tail unique-word DFT-Spread OFDM (ZT UW DTS-s OFDM), unique word OFDM (UW-OFDM), resource block-filtered OFDM, filter bank multicarrier (FBMC), and the like.

As shown in FIG. 1A, the communications system 100 may include wireless transmit/receive units (WTRUs) 102a, 102b, 102c, 102d, a RAN 104/113, a CN 106/115, a public switched telephone network (PSTN) 108, the Internet 110, and other networks 112, though it will be appreciated that the disclosed embodiments contemplate any number of WTRUs, base stations, networks, and/or network elements. Each of the WTRUs 102a, 102b, 102c, 102d may be any type of device configured to operate and/or communicate in a wireless environment. By way of example, the WTRUs 102a, 102b, 102c, 102d, any of which may be referred to as a "station" and/or a "STA", may be configured to transmit and/or receive wireless signals and may include a user equipment (UE), a mobile station, a fixed or mobile subscriber unit, a subscription-based unit, a pager, a cellular telephone, a personal digital assistant (PDA), a smartphone, a laptop, a netbook, a personal computer, a wireless sensor, a hotspot or Mi-Fi device, an Internet of Things (IoT) device, a watch or other wearable, a head-mounted display (HMD), a vehicle, a drone, a medical device and applications (e.g., remote surgery), an industrial device and applications (e.g., a robot and/or other wireless devices operating in an industrial and/or an automated processing chain contexts), a consumer electronics device, a device operating on commercial and/or industrial wireless networks, and the like. Any of the WTRUs 102a, 102b, 102c and 102d may be interchangeably referred to as a UE.

The communications systems 100 may also include a base station 114a and/or a base station 114b. Each of the base stations 114a, 114b may be any type of device configured to wirelessly interface with at least one of the WTRUs 102a, 102b, 102c, 102d to facilitate access to one or more communication networks, such as the CN 106/115, the Internet 110, and/or the other networks 112. By way of example, the base stations 114a, 114b may be a base transceiver station (BTS), a Node-B, an eNode B, a Home Node B, a Home eNode B, a gNB, a NR NodeB, a site controller, an access point (AP), a wireless router, and the like. While the base stations 114a, 114b are each depicted as a single element, it will be appreciated that the base stations 114a, 114b may include any number of interconnected base stations and/or network elements.

The base station 114a may be part of the RAN 104/113, which may also include other base stations and/or network elements (not shown), such as a base station controller (BSC), a radio network controller (RNC), relay nodes, etc. The base station 114a and/or the base station 114b may be configured to transmit and/or receive wireless signals on one or more carrier frequencies, which may be referred to as a cell (not shown). These frequencies may be in licensed spectrum, unlicensed spectrum, or a combination of licensed and unlicensed spectrum. A cell may provide coverage for a wireless service to a specific geographical area that may be relatively fixed or that may change over time. The cell may further be divided into cell sectors. For example, the cell associated with the base station 114a may be divided into three sectors. Thus, in one embodiment, the base station 114a may include three transceivers, i.e., one for each sector of the cell. In an embodiment, the base station 114a may employ multiple-input multiple output (MIMO) technology and may utilize multiple transceivers for each sector of the cell. For example, beamforming may be used to transmit and/or receive signals in desired spatial directions.

The base stations 114a, 114b may communicate with one or more of the WTRUs 102a, 102b, 102c, 102d over an air interface 116, which may be any suitable wireless communication link (e.g., radio frequency (RF), microwave, centimeter wave, micrometer wave, infrared (IR), ultraviolet (UV), visible light, etc.). The air interface 116 may be established using any suitable radio access technology (RAT).

More specifically, as noted above, the communications system 100 may be a multiple access system and may employ one or more channel access schemes, such as CDMA, TDMA, FDMA, OFDMA, SC-FDMA, and the like. For example, the base station 114a in the RAN 104/113 and the WTRUs 102a, 102b, 102c may implement a radio technology such as Universal Mobile Telecommunications System (UMTS) Terrestrial Radio Access (UTRA), which may establish the air interface 115/116/117 using wideband CDMA (WCDMA). WCDMA may include communication protocols such as High-Speed Packet Access (HSPA) and/or Evolved HSPA (HSPA+). HSPA may include High-Speed Downlink (DL) Packet Access (HSDPA) and/or High-Speed UL Packet Access (HSUPA).

In an embodiment, the base station 114a and the WTRUs 102a, 102b, 102c may implement a radio technology such as Evolved UMTS Terrestrial Radio Access (E-UTRA), which may establish the air interface 116 using Long Term Evolution (LTE) and/or LTE-Advanced (LTE-A) and/or LTE-Advanced Pro (LTE-A Pro).

In an embodiment, the base station 114a and the WTRUs 102a, 102b, 102c may implement a radio technology such as NR Radio Access, which may establish the air interface 116 using New Radio (NR).

In an embodiment, the base station 114a and the WTRUs 102a, 102b, 102c may implement multiple radio access technologies. For example, the base station 114a and the WTRUs 102a, 102b, 102c may implement LTE radio access and NR radio access together, for instance using dual connectivity (DC) principles. Thus, the air interface utilized by WTRUs 102a, 102b, 102c may be characterized by multiple types of radio access technologies and/or transmissions sent to/from multiple types of base stations (e.g., a eNB and a gNB).

In other embodiments, the base station 114a and the WTRUs 102a, 102b, 102c may implement radio technologies such as IEEE 802.11 (i.e., Wireless Fidelity (WiFi), IEEE 802.16 (i.e., Worldwide Interoperability for Microwave Access (WiMAX)), CDMA2000, CDMA2000 1X, CDMA2000 EV-DO, Interim Standard 2000 (IS-2000), Interim Standard 95 (IS-95), Interim Standard 856 (IS-856), Global System for Mobile communications (GSM), Enhanced Data rates for GSM Evolution (EDGE), GSM EDGE (GERAN), and the like.

The base station 114b in FIG. 1A may be a wireless router, Home Node B, Home eNode B, or access point, for example, and may utilize any suitable RAT for facilitating wireless connectivity in a localized area, such as a place of business, a home, a vehicle, a campus, an industrial facility, an air corridor (e.g., for use by drones), a roadway, and the like. In one embodiment, the base station 114b and the WTRUs 102c, 102d may implement a radio technology such as IEEE 802.11 to establish a wireless local area network (WLAN). In an embodiment, the base station 114b and the WTRUs 102c, 102d may implement a radio technology such as IEEE 802.15 to establish a wireless personal area network (WPAN). In yet another embodiment, the base station 114b and the WTRUs 102c, 102d may utilize a cellular-based RAT (e.g., WCDMA, CDMA2000, GSM, LTE, LTE-A, LTE-A Pro, NR etc.) to establish a picocell or femtocell. As shown in FIG. 1A, the base station 114b may have a direct connection to the Internet 110. Thus, the base station 114b may not be required to access the Internet 110 via the CN 106/115.

The RAN 104/113 may be in communication with the CN 106/115, which may be any type of network configured to provide voice, data, applications, and/or voice over internet protocol (VoIP) services to one or more of the WTRUs 102a, 102b, 102c, 102d. The data may have varying quality of service (QoS) requirements, such as differing throughput requirements, latency requirements, error tolerance requirements, reliability requirements, data throughput requirements, mobility requirements, and the like. The CN 106/115 may provide call control, billing services, mobile location-based services, pre-paid calling, Internet connectivity, video distribution, etc., and/or perform high-level security functions, such as user authentication. Although not shown in FIG. 1A, it will be appreciated that the RAN 104/113 and/or the CN 106/115 may be in direct or indirect communication with other RANs that employ the same RAT as the RAN 104/113 or a different RAT. For example, in addition to being connected to the RAN 104/113, which may be utilizing a NR radio technology, the CN 106/115 may also be in communication with another RAN (not shown) employing a GSM, UMTS, CDMA 2000, WiMAX, E-UTRA, or WiFi radio technology.

The CN 106/115 may also serve as a gateway for the WTRUs 102a, 102b, 102c, 102d to access the PSTN 108, the Internet 110, and/or the other networks 112. The PSTN 108 may include circuit-switched telephone networks that provide plain old telephone service (POTS). The Internet 110 may include a global system of interconnected computer networks and devices that use common communication protocols, such as the transmission control protocol (TCP), user datagram protocol (UDP) and/or the internet protocol (IP) in the TCP/IP internet protocol suite. The networks 112 may include wired and/or wireless communications networks owned and/or operated by other service providers. For example, the networks 112 may include another CN connected to one or more RANs, which may employ the same RAT as the RAN 104/113 or a different RAT.

Some or all of the WTRUs 102a, 102b, 102c, 102d in the communications system 100 may include multi-mode capabilities (e.g., the WTRUs 102a, 102b, 102c, 102d may include multiple transceivers for communicating with different wireless networks over different wireless links). For example, the WTRU 102c shown in FIG. 1A may be configured to communicate with the base station 114a, which may employ a cellular-based radio technology, and with the base station 114b, which may employ an IEEE 802 radio technology.

Figure 1B:
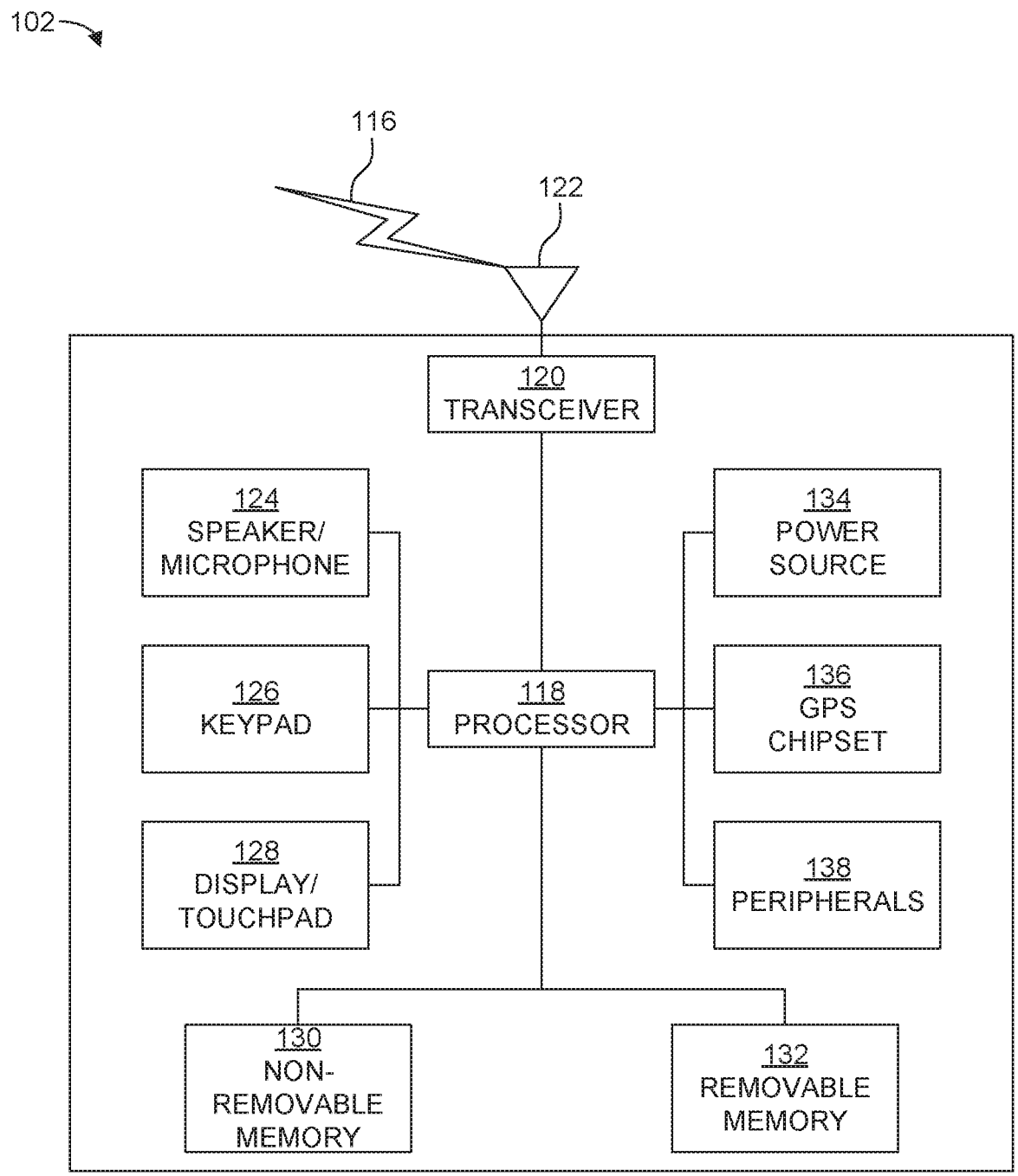
FIG. 1B is a system diagram of an example system illustrating an example wireless transmit/receive unit (WTRU) that may be used within the communications system illustrated in FIG. 1A according to some embodiments.

FIG. 1B is a system diagram illustrating an example WTRU 102. As shown in FIG. 1B, the WTRU 102 may include a processor 118, a transceiver 120, a transmit/receive element 122, a speaker/microphone 124, a keypad 126, a display/touchpad 128, non-removable memory 130, removable memory 132, a power source 134, a global positioning system (GPS) chipset 136, and/or other peripherals 138, among others. It will be appreciated that the WTRU 102 may include any sub-combination of the foregoing elements while remaining consistent with an embodiment.

The processor 118 may be a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), a state machine, and the like. The processor 118 may perform signal coding, data processing, power control, input/output processing, and/or any other functionality that enables the WTRU 102 to operate in a wireless environment. The processor 118 may be coupled to the transceiver 120, which may be coupled to the transmit/receive element 122. While FIG. 1B depicts the processor 118 and the transceiver 120 as separate components, it will be appreciated that the processor 118 and the transceiver 120 may be integrated together in an electronic package or chip.

The transmit/receive element 122 may be configured to transmit signals to, or receive signals from, a base station (e.g., the base station 114a) over the air interface 116. For example, in one embodiment, the transmit/receive element 122 may be an antenna configured to transmit and/or receive RF signals. In an embodiment, the transmit/receive element 122 may be an emitter/detector configured to transmit and/or receive IR, UV, or visible light signals, for example. In yet another embodiment, the transmit/receive element 122 may be configured to transmit and/or receive both RF and light signals. It will be appreciated that the transmit/receive element 122 may be configured to transmit and/or receive any combination of wireless signals.

Although the transmit/receive element 122 is depicted in FIG. 1B as a single element, the WTRU 102 may include any number of transmit/receive elements 122. More specifically, the WTRU 102 may employ MIMO technology. Thus, in one embodiment, the WTRU 102 may include two or more transmit/receive elements 122 (e.g., multiple antennas) for transmitting and receiving wireless signals over the air interface 116.

The transceiver 120 may be configured to modulate the signals that are to be transmitted by the transmit/receive element 122 and to demodulate the signals that are received by the transmit/receive element 122. As noted above, the WTRU 102 may have multi-mode capabilities. Thus, the transceiver 120 may include multiple transceivers for enabling the WTRU 102 to communicate via multiple RATs, such as NR and IEEE 802.11, for example.

The processor 118 of the WTRU 102 may be coupled to, and may receive user input data from, the speaker/microphone 124, the keypad 126, and/or the display/touchpad 128 (e.g., a liquid crystal display (LCD) display unit or organic light-emitting diode (OLED) display unit). The processor 118 may also output user data to the speaker/microphone 124, the keypad 126, and/or the display/touchpad 128. In addition, the processor 118 may access information from, and store data in, any type of suitable memory, such as the non-removable memory 130 and/or the removable memory 132. The non-removable memory 130 may include random-access memory (RAM), read-only memory (ROM), a hard disk, or any other type of memory storage device. The removable memory 132 may include a subscriber identity module (SIM) card, a memory stick, a secure digital (SD) memory card, and the like. In other embodiments, the processor 118 may access information from, and store data in, memory that is not physically located on the WTRU 102, such as on a server or a home computer (not shown).

The processor 118 may receive power from the power source 134, and may be configured to distribute and/or control the power to the other components in the WTRU 102. The power source 134 may be any suitable device for powering the WTRU 102. For example, the power source 134 may include one or more dry cell batteries (e.g., nickel-cadmium (NiCd), nickel-zinc (NiZn), nickel metal hydride (NiMH), lithium-ion (Li-ion), etc.), solar cells, fuel cells, and the like.

The processor 118 may also be coupled to the GPS chipset 136, which may be configured to provide location information (e.g., longitude and latitude) regarding the current location of the WTRU 102. In addition to, or in lieu of, the information from the GPS chipset 136, the WTRU 102 may receive location information over the air interface 116 from a base station (e.g., base stations 114a, 114b) and/or determine its location based on the timing of the signals being received from two or more nearby base stations. It will be appreciated that the WTRU 102 may acquire location information by way of any suitable location-determination method while remaining consistent with an embodiment.

The processor 118 may further be coupled to other peripherals 138, which may include one or more software and/or hardware modules that provide additional features, functionality and/or wired or wireless connectivity. For example, the peripherals 138 may include an accelerometer, an e-compass, a satellite transceiver, a digital camera (for photographs and/or video), a universal serial bus (USB) port, a vibration device, a television transceiver, a hands free headset, a Bluetooth® module, a frequency modulated (FM) radio unit, a digital music player, a media player, a video game player module, an Internet browser, a Virtual Reality and/or Augmented Reality (VR/AR) device, an activity tracker, and the like. The peripherals 138 may include one or more sensors, the sensors may be one or more of a gyroscope, an accelerometer, a hall effect sensor, a magnetometer, an orientation sensor, a proximity sensor, a temperature sensor, a time sensor; a geolocation sensor; an altimeter, a light sensor, a touch sensor, a magnetometer, a barometer, a gesture sensor, a biometric sensor, and/or a humidity sensor.

The WTRU 102 may include a full duplex radio for which transmission and reception of some or all of the signals (e.g., associated with particular subframes for both the UL (e.g., for transmission) and downlink (e.g., for reception) may be concurrent and/or simultaneous. The full duplex radio may include an interference management unit to reduce and or substantially eliminate self-interference via either hardware (e.g., a choke) or signal processing via a processor (e.g., a separate processor (not shown) or via processor 118). In an embodiment, the WRTU 102 may include a half-duplex radio for which transmission and reception of some or all of the signals (e.g., associated with particular subframes for either the UL (e.g., for transmission) or the downlink (e.g., for reception)).

In view of FIGS. 1A-1B, and the corresponding description of FIGS. 1A-1B, one or more, or all, of the functions described herein with regard to one or more of: WTRU 102a-d, Base Station 114a-b, and/or any other device(s) described herein, may be performed by one or more emulation devices (not shown). The emulation devices may be one or more devices configured to emulate one or more, or all, of the functions described herein. For example, the emulation devices may be used to test other devices and/or to simulate network and/or WTRU functions.

Multi-view videos (for example, 360-degree videos), also known as immersive videos or spherical videos, are video recordings such that views in multiple directions are recorded at the same time, such as by using an omnidirectional camera or a collection of cameras. During playback, the viewer has control of the viewing direction, such as with a digital panorama photo.

360-degree (or multi-view) video typically is recorded using either a special rig of multiple cameras, or using a dedicated camera that contains multiple camera lenses embedded into the device, and may involve filming overlapping angles simultaneously. Through a method known as video stitching, this separate footage is merged together into one spherical video piece, and the color and contrast of each shot is calibrated to be consistent with the others. This process is done either by the camera itself, or using specialized video editing software that may analyze common visuals and audio to synchronize and link the different camera feeds together. Generally, the only area that cannot be viewed is the view toward the camera support.

Specialized omnidirectional cameras and rigs have been developed for the purpose of filming multi-view (e.g., 360-degree) video, including rigs such as GoPro's Omni and Odyssey, the Nokia OZO, the Facebook Surround 360, the Kodak Pixpro SP360 4K Dual Pack Pro and the Axon's AZilPix Studio.One (all of which consist of multiple cameras installed into a single rig), the Vuze camera, handheld dual-lens cameras such as the Ricoh Theta S and Samsung Gear 360, and the Kogeto Dot 360—a panoramic camera lens accessory developed for the iPhone 4, 4S, and Samsung Galaxy Nexus. In videoconferencing, 360° cameras are used so that multiple (e.g., all) participants at one location may be recorded with one camera.

360-degree (or multi-view) videos are typically viewed via personal computers, mobile devices such as smartphones, or dedicated head-mounted displays, for example. If viewed on PCs, the mouse is typically used to pan around the video by clicking and dragging. On smartphones, internal sensors, such as a gyroscope, are used to pan the video based on the orientation of the device. Devices such as Google Cardboard and Samsung Gear VR viewers provide stereoscope-style headset enclosures into which a smartphone may be inserted for viewing content in a virtual reality format. Such devices may emulate the operation of a dedicated head-mounted display but utilize the display of the phone and internal lenses, rather than containing dedicated screens.

Described herein are systems and methods in accordance with some embodiments for generating and displaying multi-view (e.g., 360-degree) video content based on eye tracking and measured physiological parameters of a videographer. Multi-view (e.g., 360-degree) video may be recorded along with various contextual data to help determine a focus of the videographer at the time of recording (or shooting). multi-view (e.g., 360-degree) video may be displayed along with supplemental contextual data to help a viewer recognize objects determined to be of interest (or, e.g., important) by the videographer. This contextual data may include eye tracker (or gaze tracker or point-of-view detector) data, motion sensor data, biometric data, and other data types.

Various sub processes and modules may help render a multi-view (e.g., 360-degree) video based a videographer's focus and physiological state at the time of video capture. Furthermore, a system may include providing various visual, haptic, and sonic effects to guide a viewing experience and relay emotional state data in a natural and immersive manner. At the time of video recording, context-wise important frames of the multi-view (e.g., 360-degree) video may be determined by tracking the eyes of the videographer and detecting for fixation. Frames of the multi-view (e.g., 360-degree) video may be rendered to emphasize context-wise important portions. If a viewer wearing a HMD adjusts focus towards the context-wise important frame (turns the viewer's head to align the viewer's virtual-world view with the context-wise important frame), the videographer's emotional state, which may be determined based on information measured at the time of recording, may be vividly indicated to the viewer.

Disclosed herein are systems and methods in accordance with some embodiments for generating and displaying multi-view (e.g., 360-degree) video content based on eye tracking and measured physiological parameters. A videographer's eyes may be tracked, and a videographer's biometric indicators may be measured during multi-view (e.g., 360-degree) content recording. The rendering and playback of the recorded multi-view (e.g., 360-degree) content may enhance items identified as important.

For some embodiments, recording of multi-view (e.g., 360-degree) video may include: capturing image data depicting a multi-view (e.g., 360-degree) field of view, tracking eye movements of a videographer, and measuring physiological indicators of the videographer. The process may further include identifying an object of interest in frames of the recorded multi-view (e.g., 360-degree) video based on tracked eye movements and measured physiological indicators. The process may include rendering the recorded multi-view (e.g., 360-degree) video to emphasize the identified object of interest and deemphasize unimportant frames. During playback of the rendered multi-view (e.g., 360-degree) video, the process may apply real-time visual effects to the rendered multi-view (e.g., 360-degree) video based on the tracked eye movements and the measured physiological indicators.

Users may appreciate video capturing and viewing systems that help a viewer recognize a videographer's focus, especially in the context of multi-view (e.g., 360-degree) content and other content formats. For multi-view (e.g., 360-degree) video, a viewer may explore a captured scene from any angle. Therefore, getting a sense of the videographer's emotional state at the time of the recording may be difficult. Disclosed herein in accordance with some embodiments is an example user interface (UI)/user experience (UX) method for multi-view (e.g., 360-degree) content which may be used to identify information important to the videographer and to communicate this information to a viewer (e.g., by highlighting objects important to the videographer).

Users may appreciate smart capture and viewing systems for multi-view (e.g., 360-degree) content, which may contain vast amounts of data. With the release of multi-view (e.g., 360-degree) cameras, multi-view (e.g., 360-degree) content is being generated at a greater pace and in larger volumes. Various social platforms and services allow this content to be shared with friends. As markets are expanded for sharing multi-view (e.g., 360-degree) videos with friends, users may appreciate clear and intuitive indications of the object(s)/frame(s) in a multi-view (e.g., 360-degree) video that a videographer is most interested in.

For some embodiments, the multi-view (e.g., 360-degree) content may contain more image data than may be visible in any single moment from a viewer's point-of-view; a technique that may identify and indicate important recorded events of the videographer. During playback, in some embodiments, point-of-view data and a biometric sensor data collected during the multi-view (e.g., 360-degree) content recording process may be used to help a viewer quickly understand the viewpoint of the videographer.

Some embodiments may determine which content depicted in the multi-view (e.g., 360-degree) video data may be identified as important (or, e.g., interesting) content from the point-of-view of the videographer. Even if various examples of multi-view (e.g., 360-degree) content are shot in the same location, a particular event/object that each videographer focuses on may be different, and visual focus and emotional responses of a videographer may change continually.

For some embodiments, real-time point-of-view of a videographer may be determined using eye tracking information. Object recognition may be used to identify objects within the videographer's point-of-view. By coupling this data stream with contemporaneously sensed biometric information, objects and frames may be determined to be important and the emotional response of the videographer felt while recording may be determined. Additionally, the biometric information and sensed motion information may be stored with the videographer's important point-of-view. This stored information may be used to indicate the videographer's emotional state during playback of the recorded multi-view (e.g., 360-degree) content.

In particular, if 360-degree content recorded by a videographer is presented to a viewer, the viewer may want to be made aware of an object or a viewpoint that the videographer was focused on during the recording session. Additionally, the viewer may want to receive an indication of the videographer's feelings (emotional state as determined by measured physiological indicators) in relation to the objects or area of focus at the time of recording.

If rendering the recorded multi-view (e.g., 360-degree) video, the videographer's measured eye tracking information and the biometric sensing information may be used.

Based on the eye tracking information and biometric sensor information, frames in the 360-degree video that the videographer thinks are important (or, e.g., interesting—as, e.g., inferred from the eye tracking and biometric sensing information) may be determined. In some embodiments, frames identified as unimportant may be shrunk and merged as part of rendering the multi-view (e.g., 360-degree) video from an enhanced viewpoint of the videographer. If a rendered multi-view (e.g., 360-degree) video is played back, various effects may be triggered based on the relative distance between the calculated videographer's point-of-view at time of recording and the viewer's point-of-view.

If rendering the recorded multi-view (e.g., 360-degree) video, the videographer's measured eye tracking information and the biometric sensing information may be used in tagging an identified (or recognized) object. The system and process may determine context-wise important frames and context-wise unimportant frames using the identified (or recognized) object of interest. The context-wise unimportant frames may be shrunk to render multi-view (e.g., 360-degree) videos in a way that effectively emphasizes context-wise important frames. For some embodiments, the rendered content may be stored on a server.

For some embodiments, the above outlined example process may be applied in response to the videographer scanning the environment with a 2D camera to generate a 3D rendering or in response to a native multi-view (e.g., 360-degree) camera feed. Furthermore, in some embodiments, an object that is important from the perspective of the videographer may be determined differently depending on the characteristics of the object or the context at the time of photographing (or recording a video). For example, object recognition and classification may be used to help predict an emotional state of the videographer and to determine important and unimportant frames.

Figure 2:
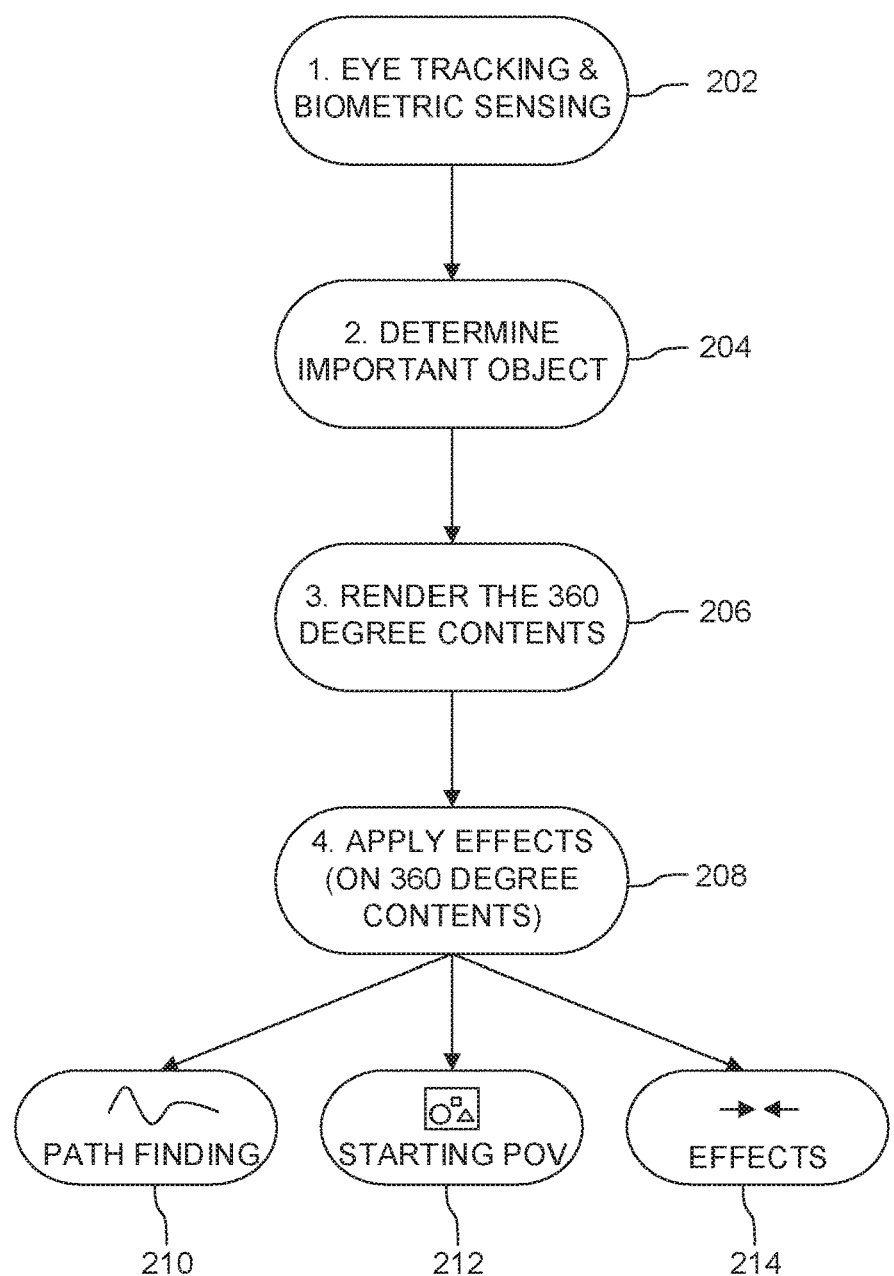
FIG. 2 is a system diagram illustrating an example process overview on generating and displaying multiview (e.g., 360-degree) video based on view direction (e.g., eye movements) and physiological indicators according to some embodiments.

FIG. 2 is a system diagram illustrating an example process overview on generating and displaying multi-view (e.g., 360-degree) video based on view direction (e.g., eye movements) and physiological indicators according to some embodiments. For some embodiments, the example process overview divides the process 200 into three stages: a recording stage, a rendering stage, and a playback stage.

For some embodiments of the recording stage, an eye tracking and biometric sensing process 202 may include, e.g., (i) capturing image data depicting a multi-view (e.g., 360-degree) field of view, (ii) tracking eye movements of a videographer (e.g., a camera operator), and (iii) measuring physiological (or biometric) indicators of the videographer. The recording stage is discussed further in, for example, the descriptions of FIGS. 5-8.

For some embodiments of the rendering stage, a process may include, e.g., identifying an object of interest (or, e.g., determine an important object) 204 in frames of the recorded multi-view (e.g., 360-degree) video based on the tracked eye movements and the measured physiological (or biometric) indicators in a point of view (POV) that may be calculated using eye tracking data and rendering the recorded multi-view (e.g., 360-degree) video contents 206 that may emphasize those frames including the identified object of interest (or important object). The rendering stage may include shrinking and merging frames of the recorded multi-view (e.g., 360-degree) content and is described further in, e.g., the descriptions of FIGS. 9-15.

For some embodiments of the playback stage, a process may include, e.g., applying real-time visual effects 208 to the rendered multi-view (e.g., 360-degree) video based on, e.g., (i) a relative distance between the videographers recorded point-of-view and a viewer's point-of-view and (ii) the measured physiological indicators associated with the important frame (or object of interest), which may highlight important objects (or objects of interest). For some embodiments, applying effects 208 may include path finding 210, determining a starting POV 212, performing an effect 214 (such as audio, brightness, friction, haptic (touch), icon impulses, magnetism, snapping, textual notifications, and zooming, for example). More information regarding the playback stage may be found in, e.g., the descriptions of FIGS. 16-29. For some embodiments, a camera operator may physically operate a camera. For example, a 360-degree camera may be mounted on a camera operator's headgear. For some embodiments, a camera operator may operate a camera remotely. For example, a camera operator may wear a 360-degree VR headset, and the camera may be controlled based on movements of the headset. For some embodiments, a camera operator may not control movements of the camera but may view multi-view (e.g., 360-degree) video as the video is captured (such as a 360-degree VR HMD worn by the camera operator). The camera operators gaze point and physiological readings may be captured while the camera operator is viewing the content. For some embodiments, a camera operator may control or view the content (for capturing gaze points and physiological measurements) at the time the content is captured. For some embodiments, content may be a multi-view (e.g., 360-degree) video. For some embodiments, a camera operator may control or view the content (for capturing gaze points and physiological measurements) at a later time based on previously captured and/or recorded content. For some embodiments, a camera operator may control or view the content (for capturing gaze points and physiological measurements) at the same time the content is live streamed to an end user and/or viewer. For some embodiments, a camera operator may control or view the content (for capturing gaze points and physiological measurements) at a first time when gaze points and physiological measurements are recorded, and the content may be streamed to an end user and/or viewer at a second later time.

Figure 3:
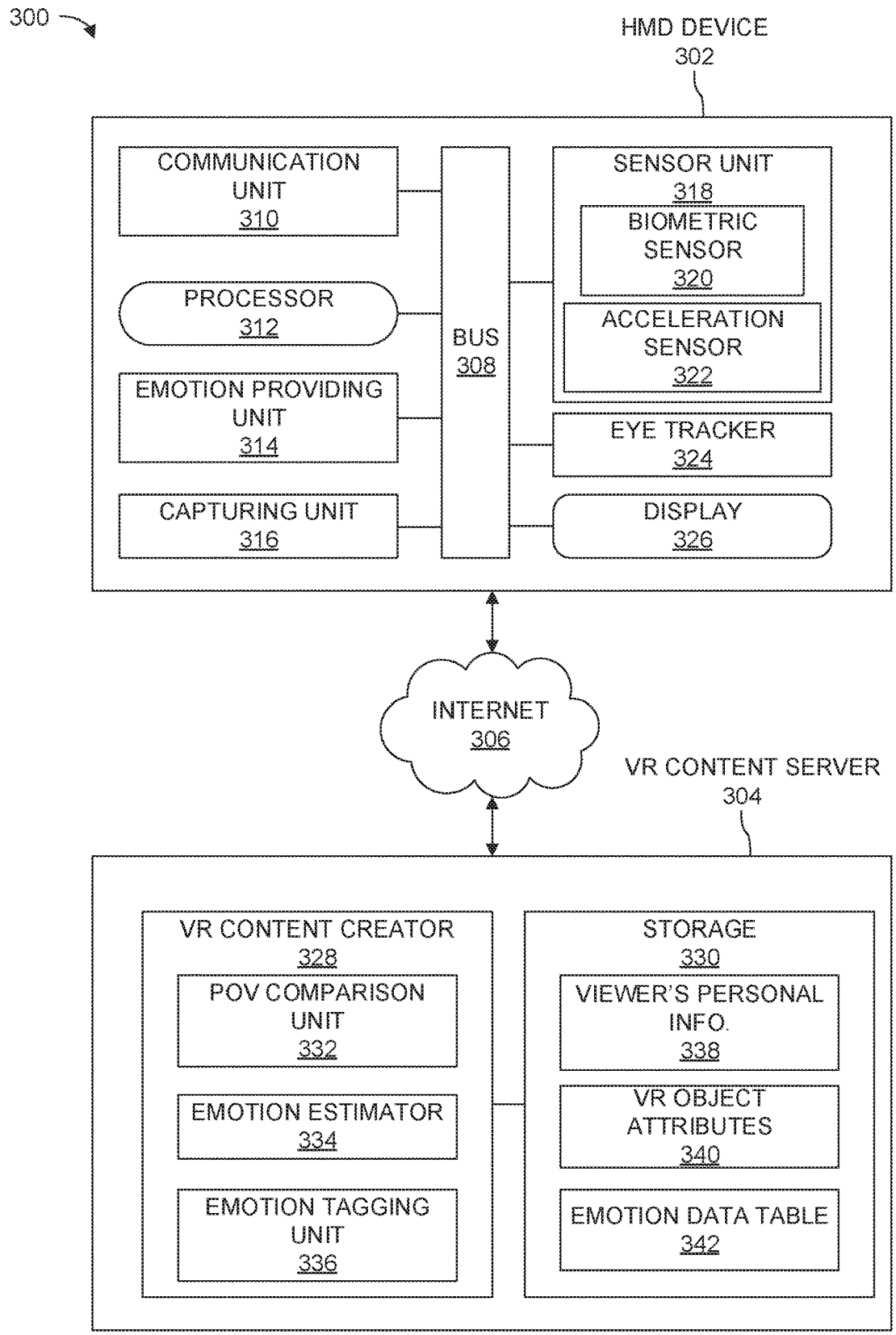
FIG. 3 is a system diagram illustrating an example set of interfaces for generating and displaying multi-view (e.g., 360-degree) video based on eye movements and physiological indicators according to some embodiments.

FIG. 3 is a system diagram illustrating an example set of interfaces for generating and displaying multi-view (e.g., 360-degree) video based on eye movements and physiological indicators according to some embodiments. FIG. 3 depicts a system 300 with an HMD device 302 and a VR content server 304 connected via the Internet 306, however a local network connection may be used as well for some embodiments. The HMD device 302 may include a bus 308 that connects a communications unit 310, a processor 312, an emotion providing unit 314, a capturing unit 316, a sensor unit 318 (that may include a biometric sensor 320 and an acceleration sensor 322), an eye tracker 324, and a display 326. The VR content server 304 may include (i) a VR content creator 328 having a point-of-view (POV) comparison unit 332, an emotion estimator 334, and an emotion tagging unit 336, and (ii) storage 330 having viewer's personal information 338, VR object attributes 340, and an emotional data table 324.

The communication unit 310 may be configured to execute all wired and wireless i/o data transfer to and from the HMD device. Connections such as WiFi, Bluetooth, USB, Ethernet, light fidelity (LiFi), or a Lightning connector, for example, may be used.

The processor 312 may be configured to control each sensor unit, display unit and emotion providing unit. The processor 312 may be configured to receive rendered VR content from the VR content server. The processor 312 may be configured to provide indications of tagged emotions to the viewer if the viewers point-of-view matches the videographers contemporaneous point-of-view.

The emotion providing unit 314 may be configured to provide indications of a videographer's emotional state to a viewer. These indications may be implemented via a variety of methods described later.

The capturing unit 316 may be configured to capture a multi-view (e.g., 360-degree) surrounding view of the environment. The multi-view (e.g., 360-degree) contents are eventually rendered and then displayed by the display unit. Capturing multi-view (e.g., 360-degree) content may be accomplished via a scanning/2D stitching process or using a native multi-view (e.g., 360-degree) recording device.

The biometric sensor 320 may be configured to detect the biological data of the HMD's user. The biometric sensor may include, e.g., ECG, EEG, PPG, GSR, and an EMG (electromyography), for example. EMG electrodes may be affixed to the user's skin surface if and/or when the user wears the HMD device. The biometric sensor 320 may be mounted in a position such that there is contact with the user's skin. In addition to biometric information collected by the HMD, biometric sensor information of a smart watch or other wearable device may be received as well. The accuracy of the biometric information may be increased for some embodiments by combining measured information from two or more devices of the HMD user. In some embodiments, if multi-view (e.g., 360-degree) video capture is initialized using the HMD, a control signal may be sent to activate the biometric sensor(s) of the wearable device(s).

The acceleration sensor 322 may be configured to detect the motion data of the HMD's user. The motion data may include, e.g., orientation data (e.g., compass data) and movement data (e.g., multi-axis g-force data). The acceleration sensor 322 may be configured to detect the head movement data of the HMD's user. The head movement data of the HMD's user may be used to compare the videographers point-of-view with the viewer's point-of-view.

The eye tracker 324 may be configured to detect at least one of a point of gaze (such as where a videographer is looking) and a motion of an eye relative to the head. The eye tracker 324 may use iris tracking, retina tracking, and/or glint tracking. The data generated by the eye tracker may be used to identify an object which holds the focus of the videographer.

The display unit 326 may be configured to display the rendered multi-view (e.g., 360-degree) contents to a viewer and may use estimated emotion information of the videographer to apply corresponding effects.

The VR content creator 328 may be configured to render VR content based on the videographer's point-of-view and tagged emotion information. The rendered VR content may be transferred to the processor 312 of the HMD. The videographer's emotion at the point-of-view may be estimated based on the biometric sensor data, the acceleration sensor data, VR object attributes data and a viewer's personal data, which may be performed by the emotion estimator 334. The estimated emotion information may be tagged to an eye-tracked virtual object depicted within the videographer's multi-view (e.g., 360-degree) video by the emotion tagging unit 336. During playback, the viewer's point-of-view may be tracked relative to the videographer's point-of-view using image analysis and acceleration sensor data. The tracked distance between the two point-of-views may be determined from triggering effects detected by the emotion tagging unit 336.

VR object attributes may include metadata surrounding identified objects of interest (or, e.g., important objects) detected within the recorded multi-view (e.g., 360-degree) content. Object attributes may include an object category, action, and intensity that may be mapped to a determined emotional state. The emotional data table may be determined from a look-up table to convert measured biometric data, acceleration data, and object attributes to a likely emotional state. Table 1 (discussed below prior to and with reference to the discussion of FIG. 19) shows an example of a look-up table.

Figure 4A:
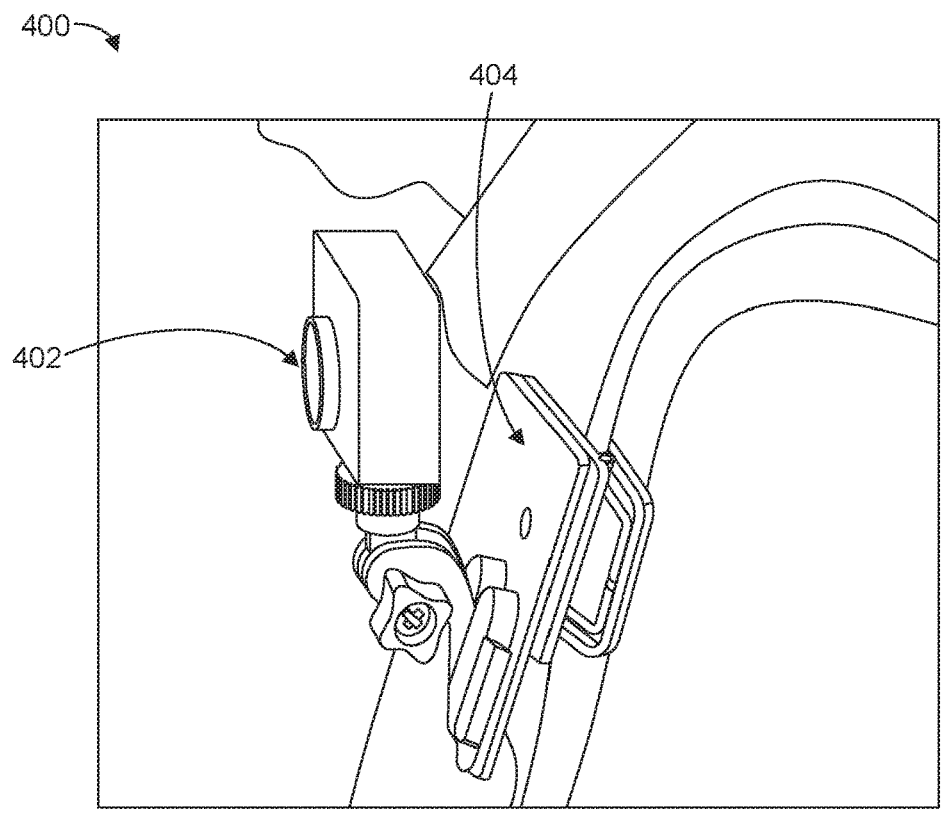
FIGS. 4A and 4B are illustrations showing example apparatuses for generating and displaying multi-view (e.g., 360-degree) video based on eye movements and physiological indicators according to some embodiments.
Figure 4B:
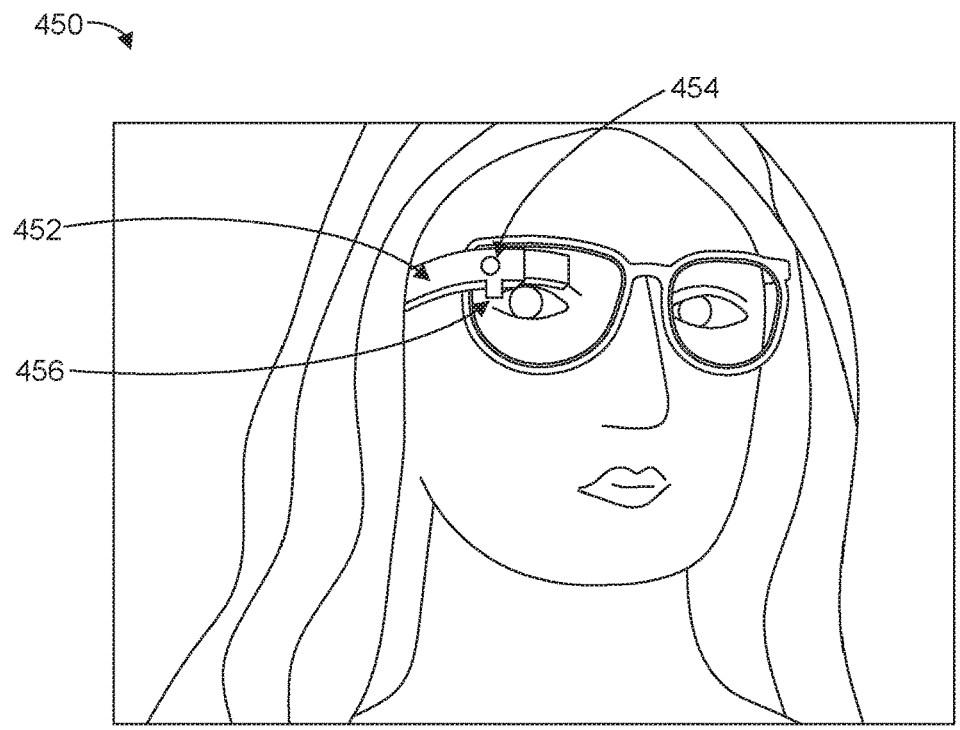

FIGS. 4A and 4B are illustrations showing example apparatuses for generating and displaying multi-view (e.g., 360-degree) video based on eye movements and physiological indicators according to some embodiments. In the example of FIG. 4A, a user wears a shoulder-mounted multi-view (e.g., 360-degree) camera system 402 having biometric sensors and a rotatable eye-tracking camera 402. The system 400 of FIG. 4A may be used to generate the multi-view (e.g., 360-degree) video and supplemental data.

In the example of FIG. 4B, a head-mounted device (HMD) including a biometric sensor and a motion sensor 452 may be used. The HMD has an outward-facing camera 454 for recording the multi-view (e.g., 360-degree) video and an inward-facing eye tracking camera 456 for some embodiments. The system 450 of FIG. 4B may be used to generate multi-view (e.g., 360-degree) video and supplemental data.

For some embodiments, a user may view the recorded and rendered 360-degree (or multi-view) video through a head mounted display. The contents of the video data may be explored via movement of the head. Biometric measurement data (which may be used to determine thoughts and emotions of a videographer (e.g., a camera operator)) may be used to determine the videographer's assessment of a level of importance for objects present within the multi-view (e.g., 360-degree) video. Such determinations may be used to, e.g., reduce a viewer's head movements and seek time and to display content efficiently.

Figure 5:
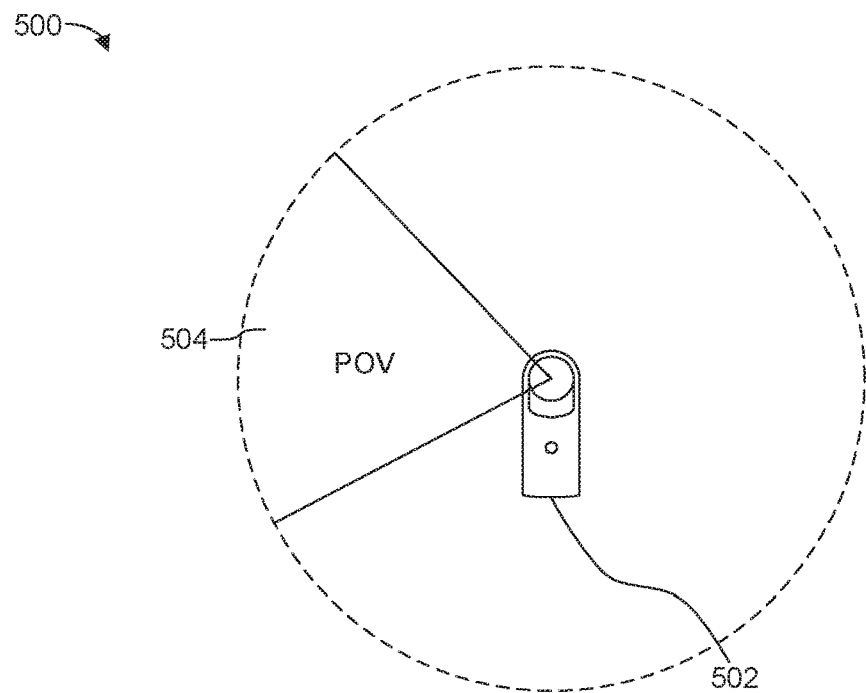
FIG. 5 is a schematic front view illustrating an example apparatus used in a recording stage including recording multi-view (e.g., 360-degree) video, biometric sensor data, and accelerometer data, and calculating a point-of-view according to some embodiments.

FIG. 5 is a schematic front view illustrating an example apparatus used in a recording stage including recording multi-view (e.g., 360-degree) video, biometric sensor data, and accelerometer data, and calculating a point-of-view according to some embodiments. An example system 500 used for a recording stage may include a multi-view (e.g., 360-degree) camera 502 capturing video information while biometric sensors record physiological (biometric) data and an eye tracking system records a gaze of the videographer and determines a videographer's point-of-view (POV) 504, which may include a focal area of a videographer's eyes. An emotion of the videographer may be determined from physiological data and in some embodiments from a characteristic on an identified object of interest. The object or frame of interest may be tagged with the determined emotion.

In some embodiments, initializing a recording with multi-view (e.g., 360-degree) camera device may trigger activation of an eye tracker and biometric sensor. The biometric sensor(s) measures a videographer's response to the physical environment and may include a photoplethysmogram (PPG) sensor, an electroencephalogram (EEG) sensor, an electrocardiogram (ECG) sensor, a peripheral capillary oxygen saturation (402) sensor, a pupil dilation sensor, and other physiological sensors, for example.

For some embodiments, the videographer's point-of-view may be determined from an eye-tracker that is coupled to an HMD. The eye-tracker may include one or more inward facing cameras for tracking movements of at least one eye of the videographer. The tracking of eye movements may be based on pupil, iris, object model, and glint tracking. The tracked movements of one or both eyes may be used to determine a time-series of gaze directions relative to the eye-tracker on the HMD. The gaze directions at each time sample may be used to calculate the videographer's point-of-view.

Figure 6:
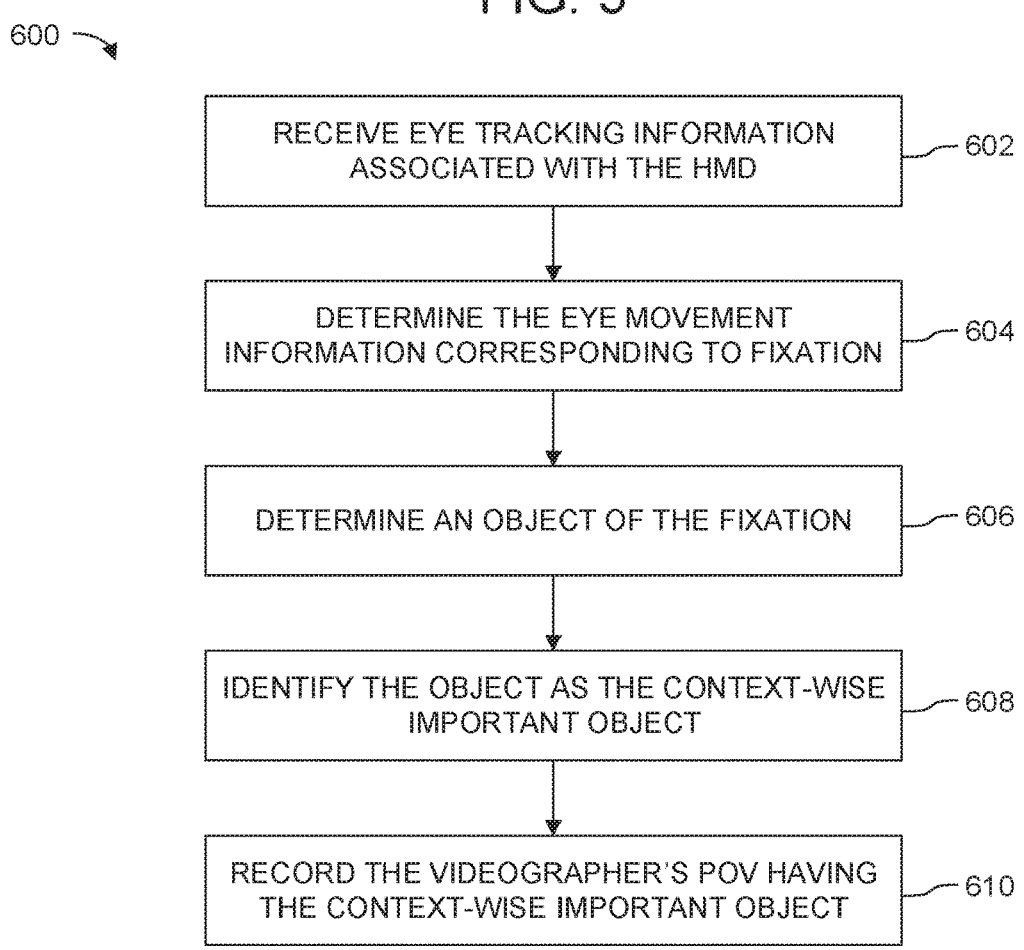
FIG. 6 is a flowchart illustrating an example process for determining a videographer's point-of-view based on eye tracking data according to some embodiments.

FIG. 6 is a flowchart illustrating an example process for determining a videographer's point-of-view based on eye tracking data according to some embodiments. An example process 600 may include receiving eye tracing information associated with the HMD 602. The process also may include determining eye movement patterns corresponding to visual fixation 604. The process also may include determining an object of the fixation 606, which may be based on time and frequency, for example. The process also may include identifying the object as a context-wise important object 608. The process also may include recording the videographer's point-of-view depicting the important object 610.

Level of interest of objects in a videographer's point of view may be identified based on eye tracking data. Eq. 1 indicates an example calculation that may be used to determine a level of interest of objects for some embodiments:

$$\text{Level of Interest}(Obj) = \text{Sustaining}(Obj) + \text{Frequency}(Obj) \qquad \text{Eq. 1}$$

Sustaining (Obj) is a starting time substantially within one object and Frequency (Obj) is a cumulative number of times a viewer turns to watch the same object. Eq. 1 is an example formulation and, e.g., other determinations or relationships may be used as suitable to estimate a level of interest in an object or objects. Of course, in some embodiments, a level of interest in an object may be indicated or otherwise inferred without using (exclusively or otherwise) a determination.

For some embodiments, a sustained gaze may be determined if consecutive gaze points in a series of gaze points are substantially within one area. As such, the sustained gaze may be determined if the videographer is staring at an object of interest such that eye movements of the videographer indicate that the videographer may be looking intently towards an object of interest, resulting in consecutive gaze points in the series of gaze points being substantially within an area (which may be in proximity to the object of interest).

For some embodiments, a context-wise important object in the videographer's point-of-view is determined by referencing the biometric sensor information. The biometric sensor information is detected as the videographer's point-of-view is detected. Other example factors which may be used for determining the context-wise important objects include: whether the pupil size of the videographer increases suddenly (within a threshold period of time) when the videographer is looking the object within the point-of-view; whether the pulse rate increases suddenly (e.g., above an average pulse rate threshold) when the videographer is looking at the object within the point-of-view; and whether the motion information increases suddenly (e.g., if the videographer falls in amazement) when looking at the object within the point-of-view. The videographer's point-of-view (which may be determined based on eye-tracking information) may be stored with respect to the recording's time-sequence. The videographer's point-of-view may include context-wise important objects upon which the videographer is looking at intently.

Figure 7:
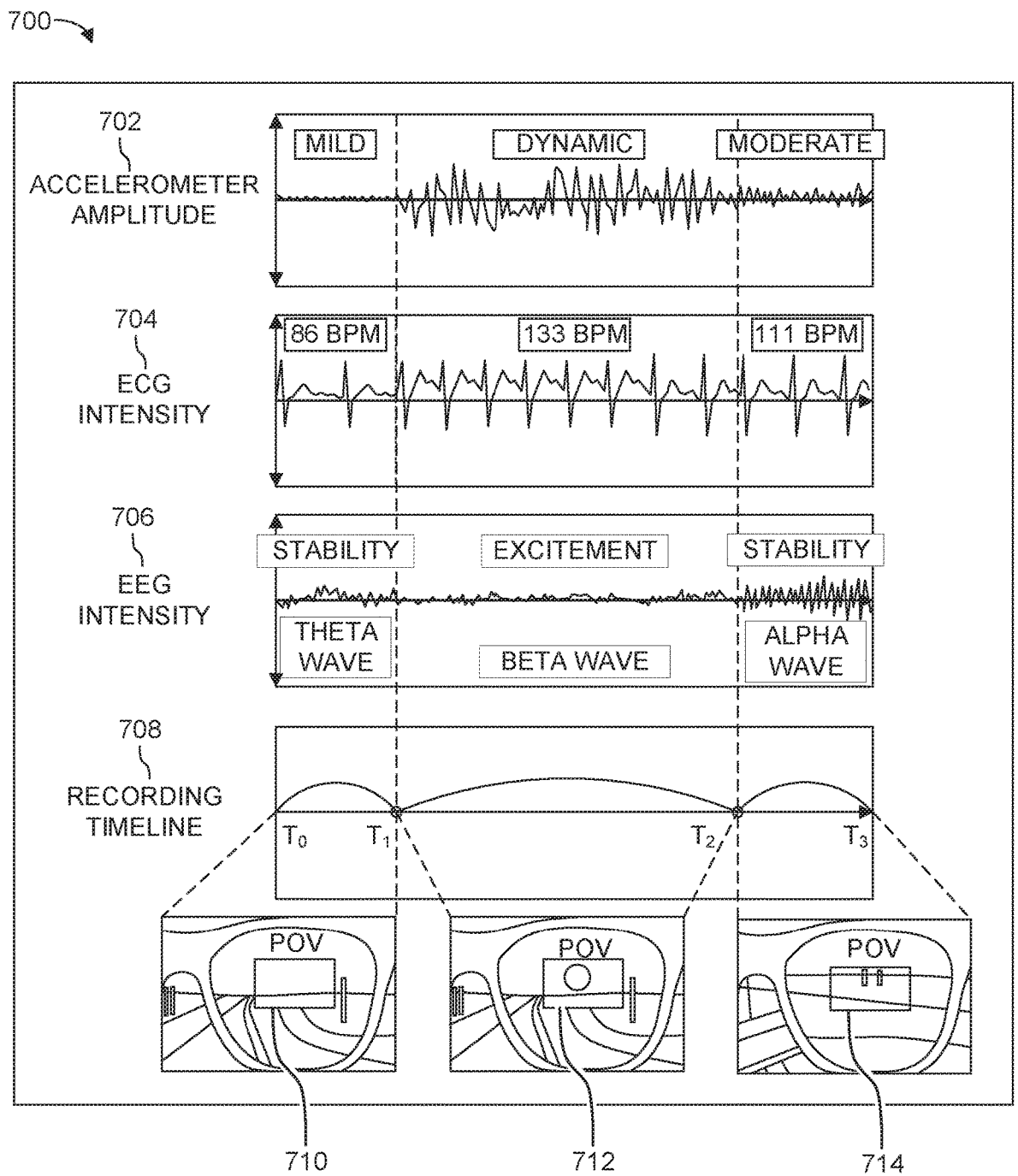
FIG. 7 is a timing diagram illustrating an example set of measurements of biometric sensor data and accelerometer data aligned with respect to a videographer's contemporaneous point-of-view according to some embodiments.

FIG. 7 is a timing diagram 700 illustrating an example set of measurements of biometric sensor data and accelerometer data aligned with respect to a videographer's contemporaneous point-of-view according to some embodiments. For some embodiments, recorded biometric sensing information and motion sensing information may be used in estimating the videographer's emotional state.

In some embodiments, when a video recording device (such as an HMD device with a camera) records an image of the user's (or wearer's) surroundings, a sensor (e.g., accelerometer, electrocardiography (ECG) sensor, or electroencephalography (EEG) sensor) included in the device (or coupled to the device or a shared resource) may measure data. This data may be sent to the VR content server such that a VR content creator may analyze the patterns of the data and group time-sequences into sections. According to the example, the grouped interval information is matched with the time interval coinciding with the recorded video. An emotional state may be estimated based on, e.g., the relationship between data values of each sensor, inferences made using the video data, and/or other contextual indicators. For some embodiments, a series of estimated emotional states may be condensed into one emotional state by referring to the object at which the wearer is looking during the recording of the corresponding section.

Acceleration sensor readings 702 may be used in emotional state estimation, providing the estimation function with a reading of the videographer's movements. If the intensity of acceleration sensor data is less than a threshold A, the intensity may be identified as a mild movement. If the intensity of acceleration sensor data is between thresholds A and B, the intensity may be identified as a moderate movement. If the intensity of acceleration sensor data is greater than a threshold B, the intensity may be identified as a dynamic movement if the intensity is more than preset B value. FIG. 7 shows example acceleration sensor readings 702 indicating a mild movement occurring between t0 and t1, a dynamic movement occurring between t1 and t2, and a moderate movement occurring between t2 and t3.

ECG sensor readings 704 may be used in emotional state estimation, providing the estimation function with a reading of the videographer's average heart rate. FIG. 7 shows example ECG sensor readings 704 of 86 beats per minute (BPM) occurring between t0 and t1, 133 BPM occurring between t1 and t2, and 111 BPM occurring between t2 and t3.

EEG sensor readings 706 may be used in emotional state estimation, providing the estimation function with a reading of the videographer's brain-wave activity. FIG. 7 shows example EEG sensor readings 706 with a theta wave indicating stability occurring between t0 and t1, a beta wave indicating excitement occurring between t1 and t2, and an alpha wave indicating stability occurring between t2 and t3. EEG sensor readings may be divided into beta wave (excitation), alpha wave (stable), theta (sleep), spindle wave (sleep), and delta wave (sleep) depending on measured activity level.

EMG sensor readings (not shown) may be used in emotional state estimation, providing the estimation function with a reading of the muscle movements. Sensing information (e.g., biometric sensing information and acceleration sensing information) received from the HMD sensors may be prepared if the videographer's point-of-view is determined. The sensing information may be tagged to a context-wise important object or frame within the videographer's point-of-view. The tagged sensing information (e.g., emotional state) may be used to provide various visual effects that are triggered when the viewers point-of-view nears or matches the videographer's point-of-view. This tagged information may be communicated to the viewer so that the viewer may experience the emotion or reaction the videographer felt about the context-wise important object. Thus, the emotional state of the videographer in relation to the important object may be communicated to the viewer.

For the example recording timeline 708 of FIG. 7, an emotional state may be estimated to be "calm" between time t0 and t1, "excited" between t1 and t2, and "happy" between t2 and t3. These emotional states may be tagged to the corresponding objects (e.g., fireworks explosion) within the contemporaneous point-of-views 710, 712, 714. At the rendering stage, the biometric information and the acceleration information may be converted into emotion-indicator information by the VR content creator. The emotion-indicator information may be used to deliver the feeling and experience of the videographer at the time of recording.

For some embodiments, determining a portion of the multi-view (e.g., 360-degree) video containing an object of interest may include matching an identified object of interest with a camera angle and a time period of a multi-view video that contains video of the identified object of interest. For some embodiments, such a matching process may occur at the time the video is captured. For some embodiments, such a matching process may occur at the time the video is displayed to an end user and/or viewer. For some embodiments, the time the video is captured is the same as the time the video is displayed and viewed by an end user and/or viewer. For some embodiments, a portion of physiological data (e.g., accelerometer amplitude data 702, ECG intensity data 704, or EEG intensity data 706) may be selected based on an object of interest identified in the multi-view (e.g., 360-degree) video. For some embodiments, the object of interest may be identified at the time of capturing the video. For some embodiments, the object of interest may be identified at the time of viewing.

Figure 8:
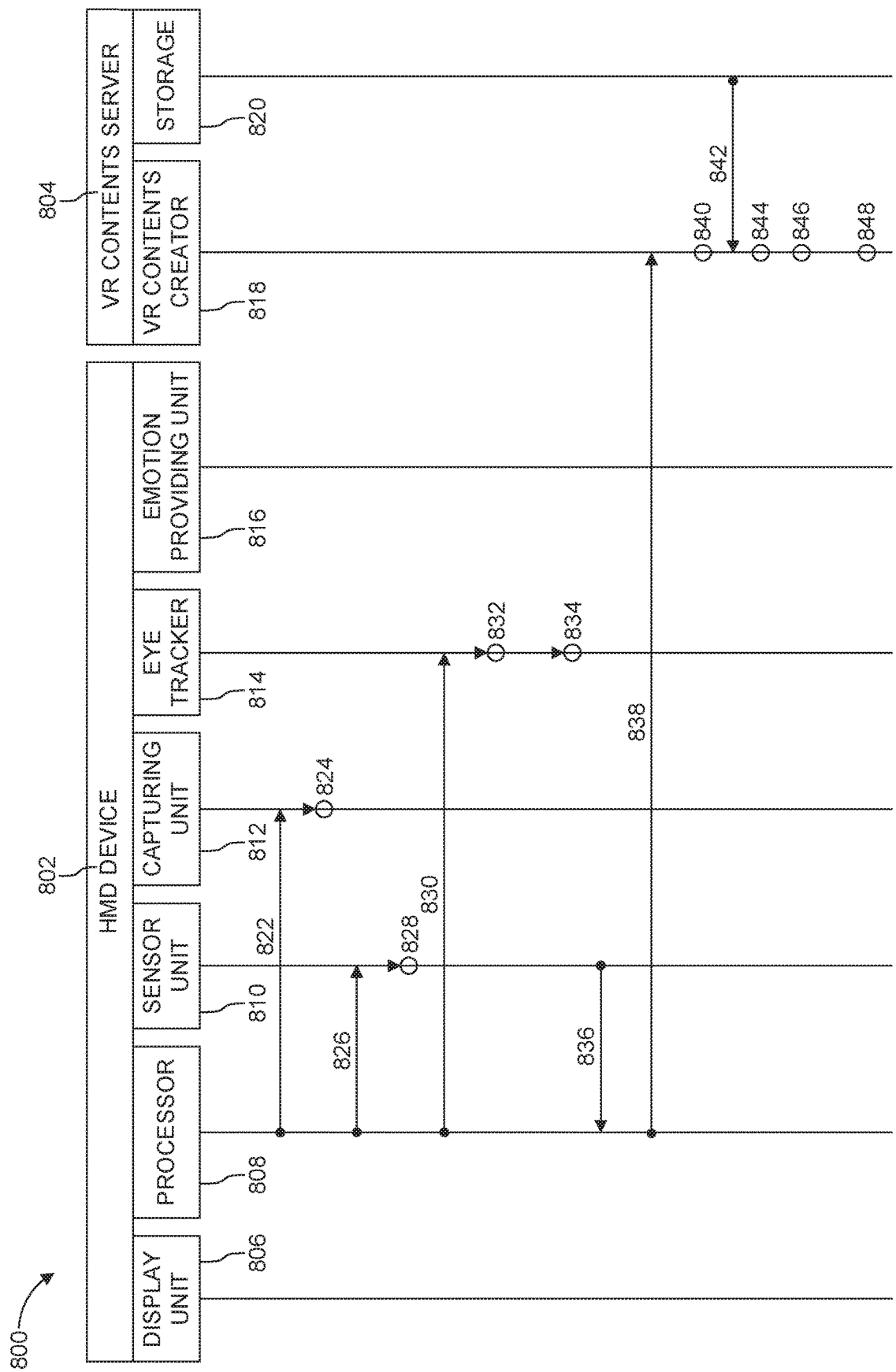
FIG. 8 is a message sequencing diagram illustrating an example process for recording and rendering multi-view (e.g., 360-degree) content according to some embodiments.

FIG. 8 is a message sequencing diagram illustrating an example process for recording and rendering multi-view (e.g., 360-degree) content according to some embodiments. The message sequence diagram 800 of FIG. 8 shows an HMD device 802 and a VR contents server 804. For some embodiments, the HMD device 802 includes, e.g., a display unit 806, a processor 808, a sensor unit 810, a capturing unit 812, an eye tracker 814, and an emotion providing unit 816. For some embodiments, the VR contents server 804 includes, e.g., a VR contents creator 818 and storage 820.

The processor 808 may be configured 822 to capture a multi-view (e.g., 360-degree) video recorded by a videographer (e.g., a camera operator). The multi-view (e.g., 360-degree) video may be captured 824 by the capturing unit 812. The processor 808 may be configured 826 to activate the sensor unit 810 (e.g., a biometric sensor and an acceleration sensor). Biometric sensor data and acceleration sensor data may be detected 828 by sensor(s) 810 and may be communicated to the processor 808. The processor 808 may be configured 830 to determine a point-of-view of the videographer by using eye tracking with the eye tracker 814. The videographer's point-of-view may be detected 832 based on the eye tracking information. An important virtual object may be detected 834 within the detected point-of-view. The sensed data within the point-of-view may be transferred 836 to the processor 808. The processor 808 may be configured to transfer 838 the sensed data to a VR contents server 804 (which may include a VR contents creator 818).

The recorded video may be segmented 840 into timesequences (e.g., the captured section of the recorded video is determined as the emotion tagging section) as the sensed data corresponds to predetermined conditions indicating various emotional states. VR attribute data and the videographer's personal data may be transferred 842 to the VR contents creator 818 from storage 820. The videographer's emotion at the point-of-view may be estimated 844 by the emotion estimator of the VR contents creator 818. The estimated emotion may be tagged 846 at the point-of-view within the emotion tagging section. After recording, the VR content may be rendered 848 based on the tagged emotion at the videographer's point-of-view. For some embodiments, an HMD device 802 includes a display unit 806 and an emotion providing unit 816.

Figure 9:
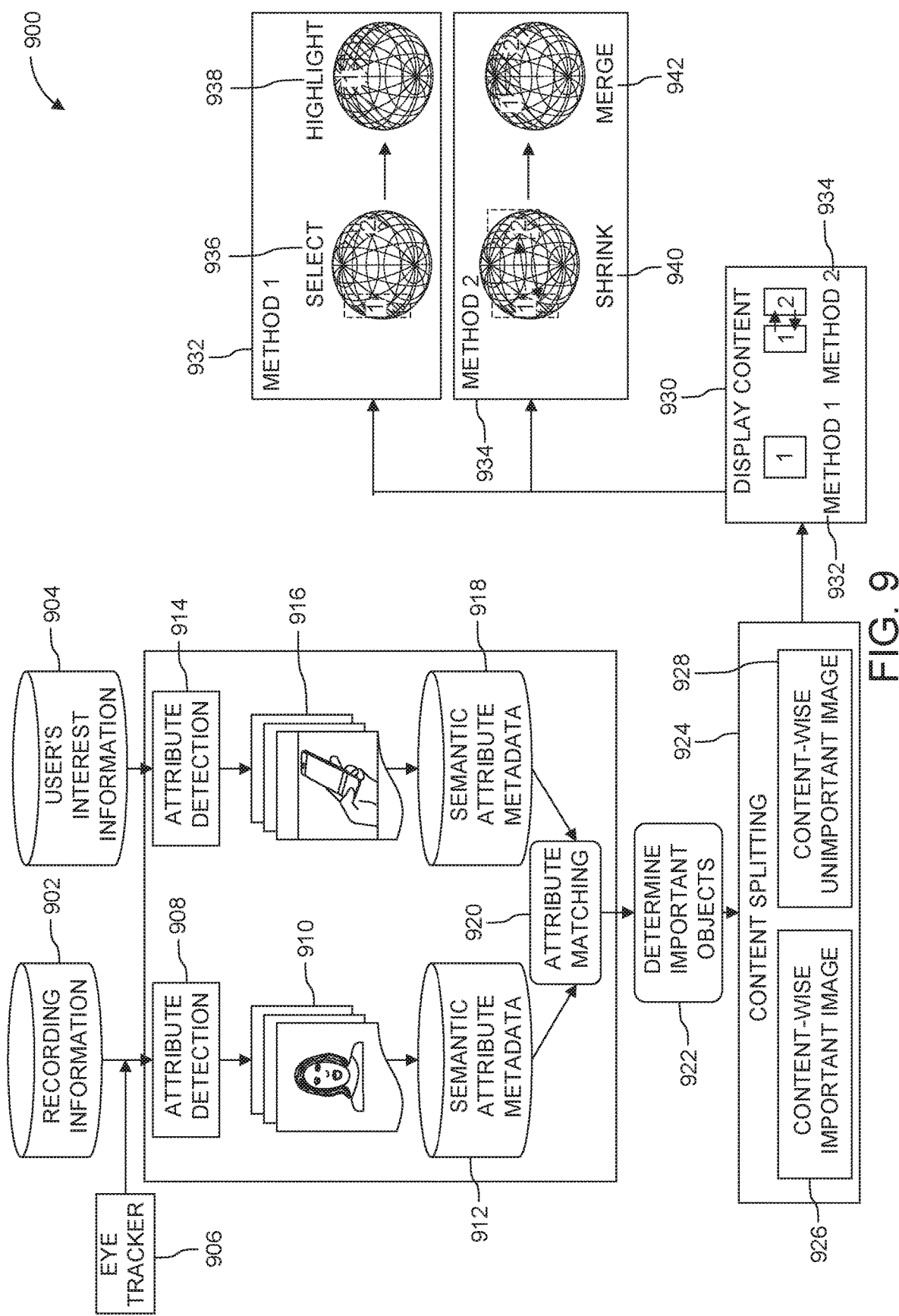
FIG. 9 is a process diagram illustrating an example two-way-rendering process according to some embodiments.

FIG. 9 is a process diagram illustrating an example two-way-rendering process according to some embodiments. For an example process 900, recording information 9may be retrieved 902 from memory and sent to a first attribute detection process 908 for some embodiments. Eye tracker data may be received 906 and sent to the first attribute detection process 908. User's interest information may be retrieved 904 from memory and sent to a second attribute detection process 914. Each process 908, 914 may use video data 910, 916 to generate 912, 918 semantic attribute metadata, which may be inputted to an attribute matching process 920. The output of the attribute matching process 920 may be used by a process 922 that determines important objects in the point-of-view. A content splitting process 924 may divide the video data into context-wise important images 926 and context-wise unimportant images 928. A content displaying process 930 may determine whether to use a first rendering method 932 or a second rendering method 934. The first method 932 may select 936 an important object and highlight 938 the important object. The second method 934 may shrink 940 unimportant frames and merge 942 the shrunk frames.

For rendering the multi-view (e.g., 360-degree) content, the recorded videographer's point-of-view may be identified as the context-wise important frame. The server system may render the multi-view (e.g., 360-degree) content by selecting 936 and highlighting 938 (rendering method 1 (932)) or shrinking 940 and merging 942 (rendering method 2 (934)) the captured multi-view (e.g., 360-degree) video based on the context-wise important frame. For some embodiments, if only one context-wise important frame is present, the first rendering method 932 may be applied to adjust the brightness, size, and position of the important object in order to highlight the context-wise important frame. For some embodiments, if at least two context-wise important frames are present, the second rendering method may be applied to shrink context-wise unimportant frames between context-wise important frames thereby providing important information of the videographers perspective to the viewer. The first rendering method 932 may emphasize a videographer's viewpoint of the multi-view (e.g., 360-degree) content and enable a viewer to skim the multimedia data.

Figure 10:
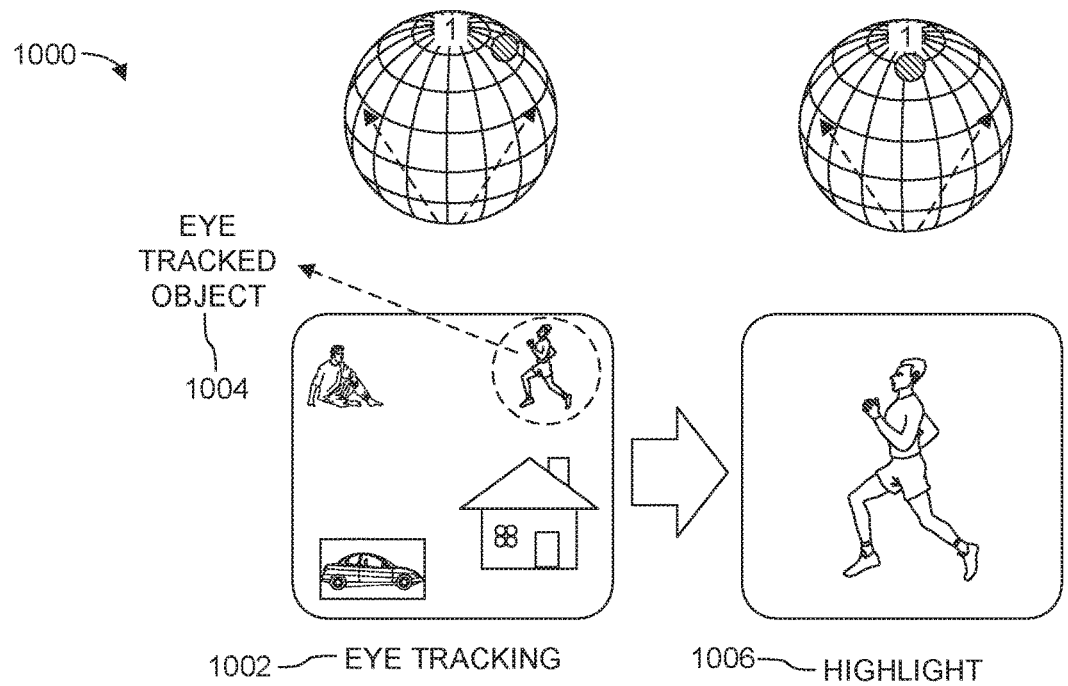
FIG. 10 is a process diagram illustrating an example of a first rendering method according to some embodiments.

FIG. 10 is a process diagram illustrating an example of a first rendering method according to some embodiments. The illustration 1000 shows an example of a running woman being detected as an important object (based on eye tracking 1002) and responsively being enlarged to highlight 1006. Because there is one context-wise important object determined by eye recognition information, the first rendering method of FIG. 9 may be applied. The highlighted or selected frame containing the eye tracked object 1004 (the running woman) may be highlighted (or displayed) 1006 in a manner that is distinctive from other displayed frames, for example by being presented in a larger size, vivid color, possibly overlapping other frames. The eye-tracked object (e.g., a running woman) may be enlarged with respect to other objects to indicate a highlighted state. For example, a highlighted object may be shown in color while others are black and white, and/or its appearance may be enhanced, brightened, or otherwise adjusted, and/or its frame may be shown in a different color or other visually-distinctive way.

Figure 11:
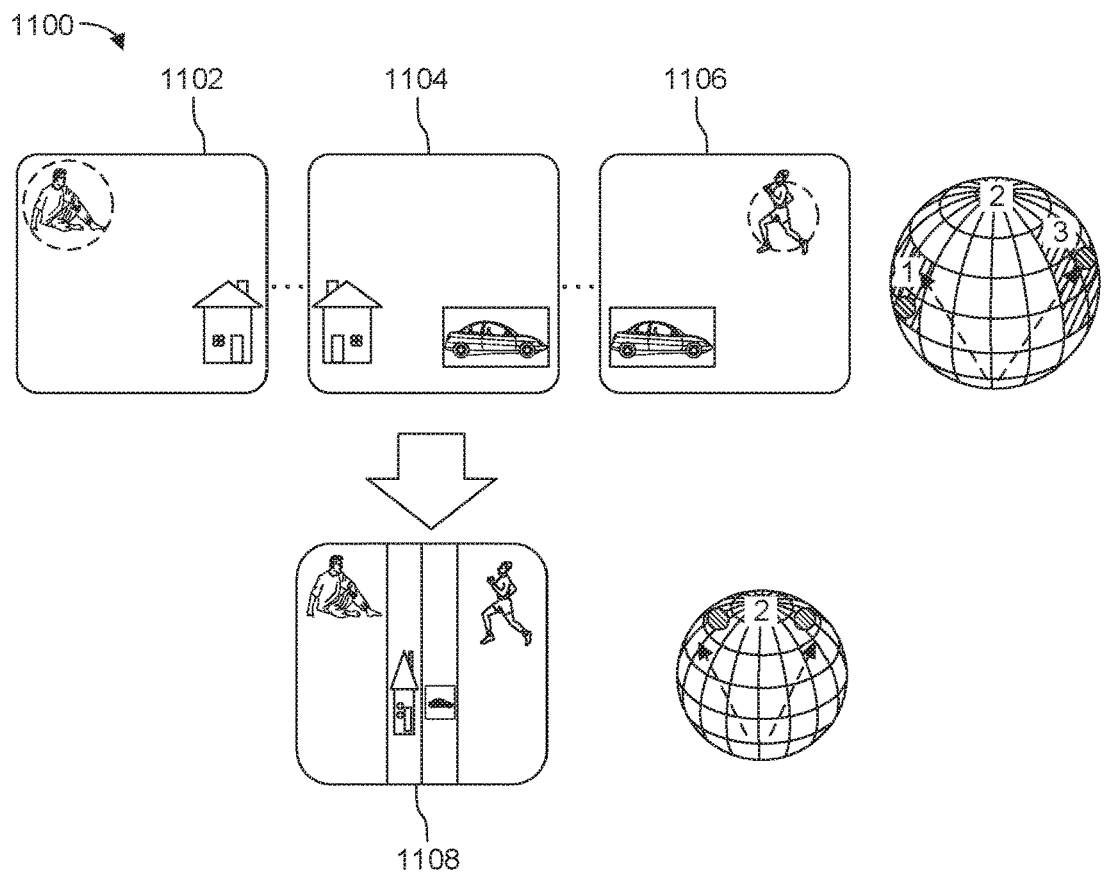
FIG. 11 is a process diagram illustrating an example of a second rendering method according to some embodiments.

FIG. 11 is a process diagram illustrating an example of a second rendering method according to some embodiments. The illustration 1100 shows an example of a running woman and a sitting man being detected as important objects. Because two context-wise important objects are detected based on eye recognition information, the second rendering method of FIG. 9 is applied. In the second rendering method of FIG. 9, the multi-view (e.g., 360-degree) video may be divided into context-wise (or content-wise) important frames having context-wise important objects and context-wise unimportant frames not having context-wise important objects. For the example of FIG. 11, context-wise important objects are detected within two viewpoints 1102, 1106. The second rendering method of FIG. 9 shrinks context-wise unimportant frames (which are within the viewpoint 1104 for the example of FIG. 11) and enables a viewer to avoid large angle head rotations to switch focus from one important object to another important object. Although the at least one context-wise unimportant frame 1104 is shrunk in the viewer's viewpoint 1108, the user is able to recognize the environmental context in the multi-view (e.g., 360-degree) content without rotating his or her head.

Figure 12:
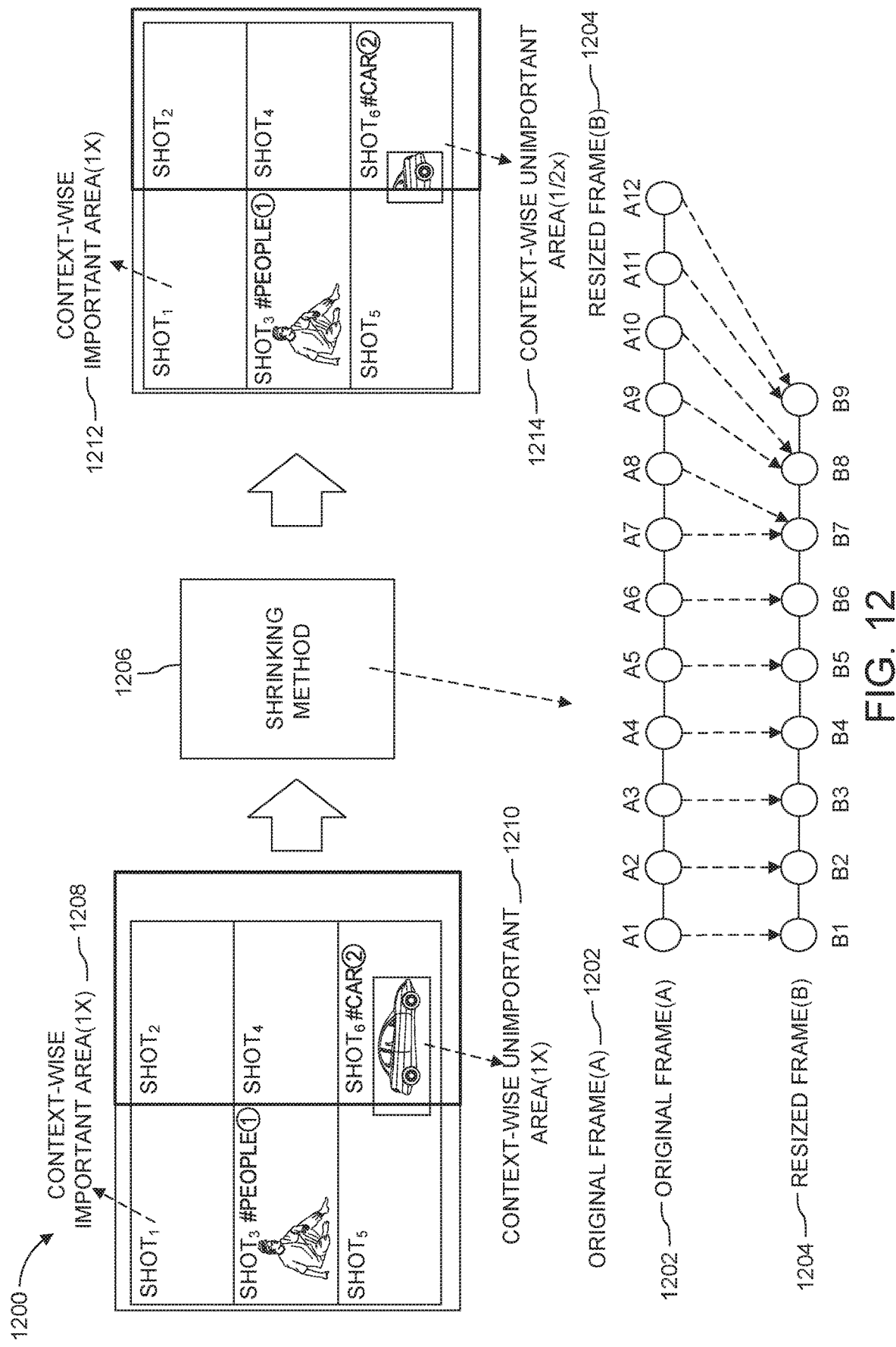
FIG. 12 is a process diagram illustrating an example method for shrinking frames according to some embodiments.

FIG. 12 is a process diagram illustrating an example method for shrinking frames according to some embodiments. The methodology 1200 of FIG. 12 shows an example pixel-mapping technique (or shrinking method 1206). In the example shown in FIG. 12, the original frame (A) 1202 has a horizontal line of 12 pixels. The left six pixels A1-A6 are determined to be important objects, as determined by users interest information, and the right six pixels A7-A12 are determined to be low importance (or unimportant) objects, as determined by user's interest information.

If the original frame (A) 1202 is resized to a resized frame (B) 1204 with a width of nine pixels, a pixel mapping method for some embodiments maps the left six pixels A1-A6 to the same position, shown by pixels B1-B6 in the resized frame (B) 1204. Pixels A1-A6 are determined to be part of a context-wise important area 1208. The right six pixels A7-A12 are merged to generate three pixels B7-B9 for the resized frame (B) 1204. Pixels A7-A12 are determined to be part of a context-wise unimportant area 1210. Within the resized frame (B) 1204, pixels B1-B6 correspond to a context-wise important area 1212, and pixels B7-B9 correspond to a context-wise unimportant area 1214. For the example of FIG. 12, the original frame (A) 1202 uses a 1× compression ratio for the context-wise unimportant area 1208 and the context-wise unimportant area 1210, and the resized frame (B) 1204 uses a 1× compression ratio for the context-wise unimportant area 1212 and a 0.5× compression ratio for the context-wise unimportant area 1214. For some embodiments, these compression ratios may be changed.

Figure 13:
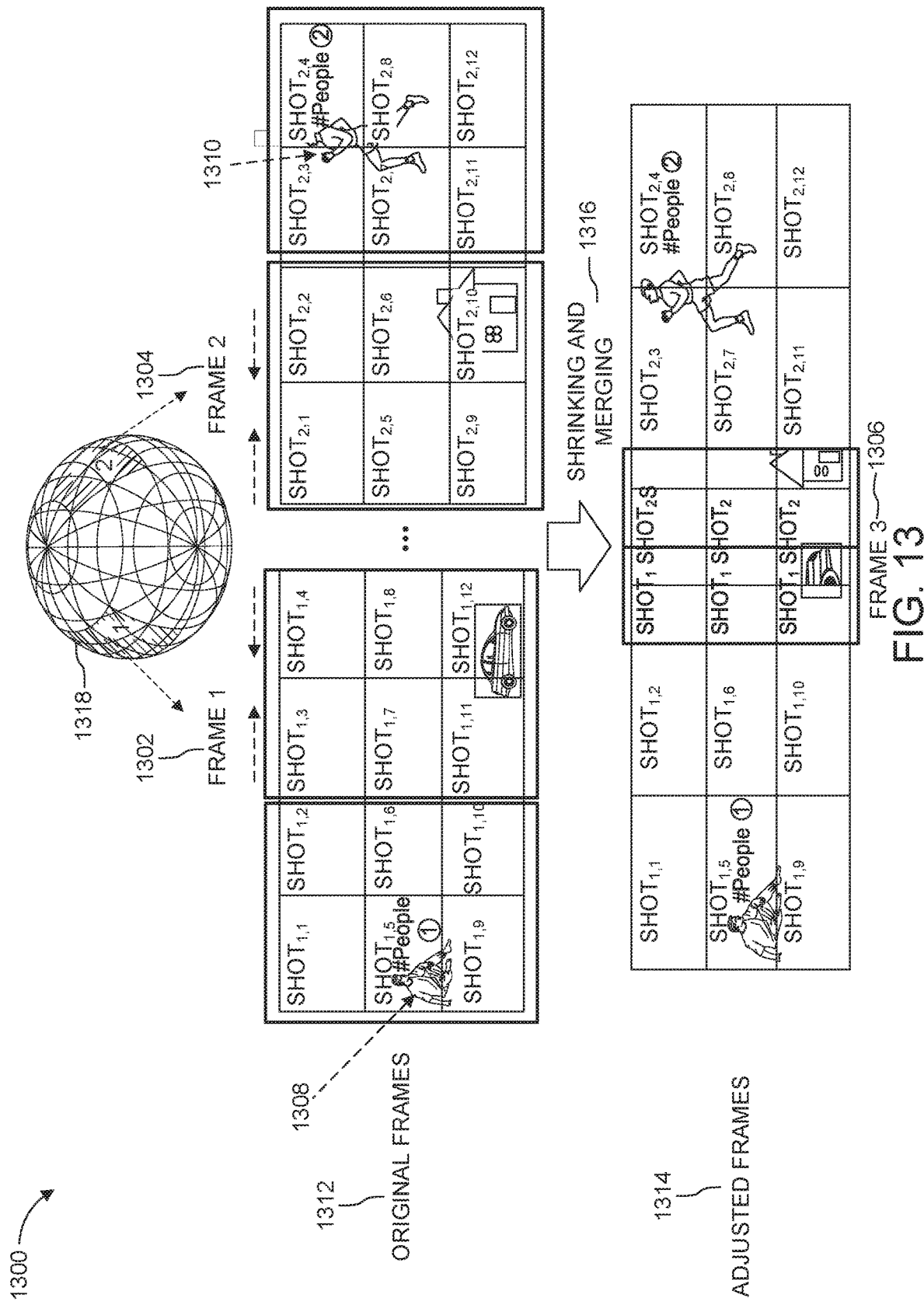
FIG. 13 is a process diagram illustrating an example method for merging shrunk frames according to some embodiments.

FIG. 13 is a process diagram illustrating an example method for merging shrunk frames according to some embodiments. FIG. 13 shows a methodology 1300 for a merging technique for some embodiments. In FIG. 13, the size of at least two frames in the multi-view (e.g., 360-degree) content may be resized in the x direction based on the importance value of the detected objects (having at least one pixel). For the example of FIG. 13, frame 1 (1302) and frame 2 (1304) do not contain objects of interest 1308, 1310 and frame 1 (1302) and frame 2 (1304) are shrunk and merged 1316 to form frame 3 (1306). Also, for this example, frame 1 (1302) and frame 2 (1304) are far apart from each other in the multi-view (e.g., 360-degree) environment 1318.

Some embodiments resize the frames (or images) by mapping pixels in the original frames (or images) 1312 to different positions in the adjusted frames (or resized images) 1314. For some embodiments of shrinking the image, those pixels of the original frames 1312 with high importance (which may be pixels that are part of an object of interest) may be mapped one-to-one to separate pixels in the adjusted frames (or resized images) 1314, and unimportant pixels of the original frames 1312 may be shrunk and merged 1316 in the adjusted frames (or resized images) 1314.

For some embodiments, the multi-view (e.g., 360-degree) image also may be resized by removing a target number of seams from each of a set of respective seam groups. Removing a seam may cause the image to shrink horizontally or vertically by the width of the deleted seam. Removal of a vertical seam shrinks the image in the horizontal direction by the width of the seam removed. Likewise, removal of a horizontal seam shrinks the image in the vertical direction by the width of the seam removed.

Figure 14:
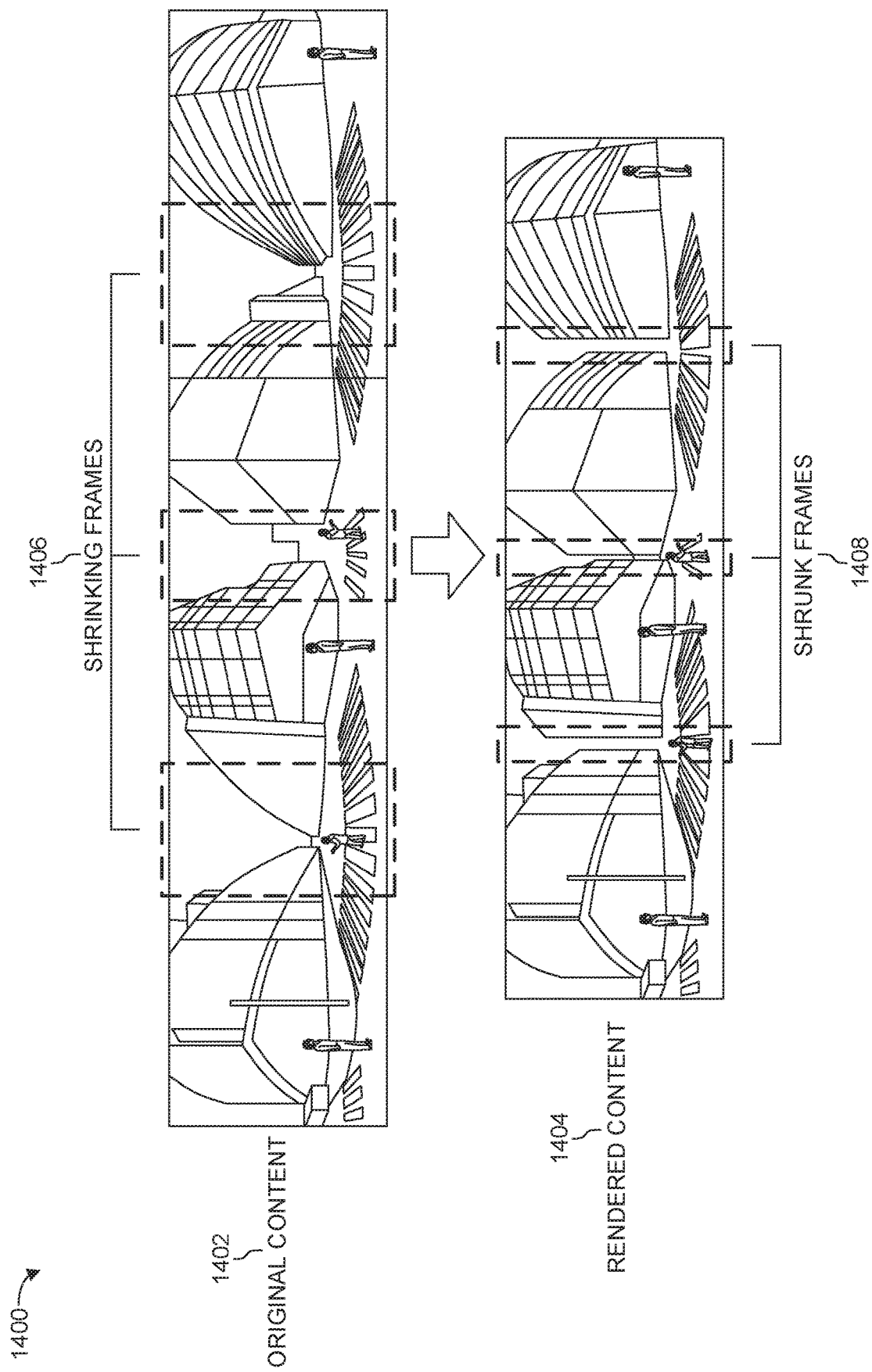
FIG. 14 is a process diagram illustrating an example for shrinking and merging frames according to some embodiments.

FIG. 14 is a process diagram illustrating an example for shrinking and merging frames according to some embodiments. FIG. 14 shows for some embodiments the effects of shrinking and merging by comparing original content 1402 to rendered content 1404. FIG. 14 shows an example for some embodiments of shrinking frames 1406, which include open spaces between buildings for this example, that become shrunk frames 1408 in the rendered content 1404.

Figure 15:
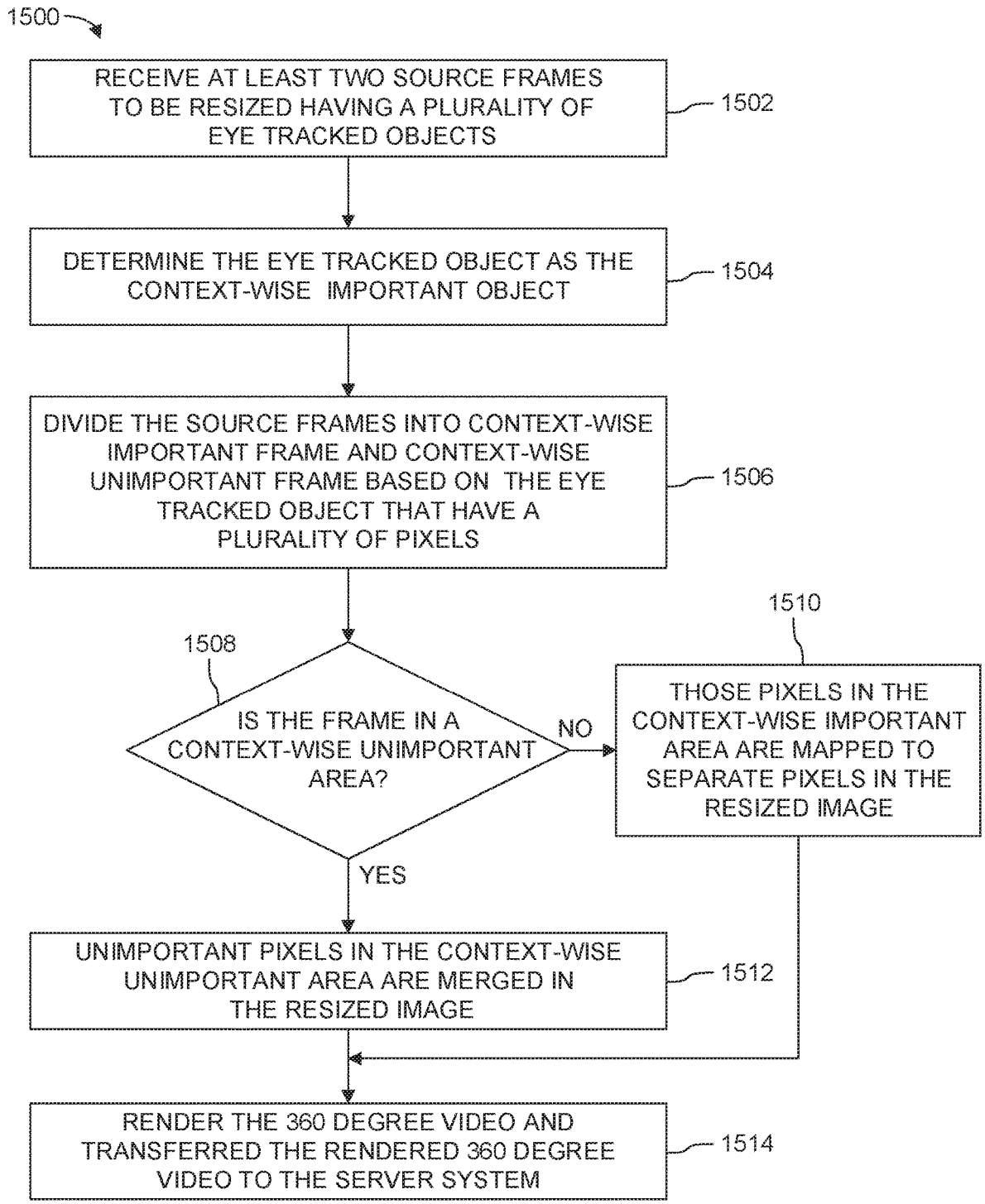
FIG. 15 is a flowchart illustrating an example process for shrinking and merging frames based on eye tracking data according to some embodiments.

FIG. 15 is a flowchart illustrating an example process for shrinking and merging frames based on eye tracking data according to some embodiments. Some embodiments of an example process 1500 described below may be used to shrink and merge frames lacking eye tracked objects of interest. The process 1500 may include receiving 1502 at least two source frames (to be resized) depicting a plurality of eye-tracked objects. The process 1500 may include determining 1504 (or, e.g., identifying) an eye-tracked object as a context-wise important object. The process 1500 also may include dividing 1506 the source frames into context-wise important frames and context-wise unimportant frames. The dividing 1506 may be based on the eye tracked object that have a plurality of pixels. The process 1500 may determine 1508 whether a frame is in a context-wise unimportant area. If the frame is in a context-wise unimportant area, then (unimportant) pixels belonging to a context-wise unimportant frame may be merged 1512 in the resized image. If the frame is not in a context-wise unimportant area, then those pixels belonging to the context-wise important frame may be mapped 1510 to separate pixels in the resized image. In both events 1512 and 1510, the example process 1500 may also include rendering 1514 the multi-view (e.g., 360-degree) video using the resized frames and transferring the rendered multi-view (e.g., 360-degree) video to, e.g., a server system for content distribution.

Figure 16:
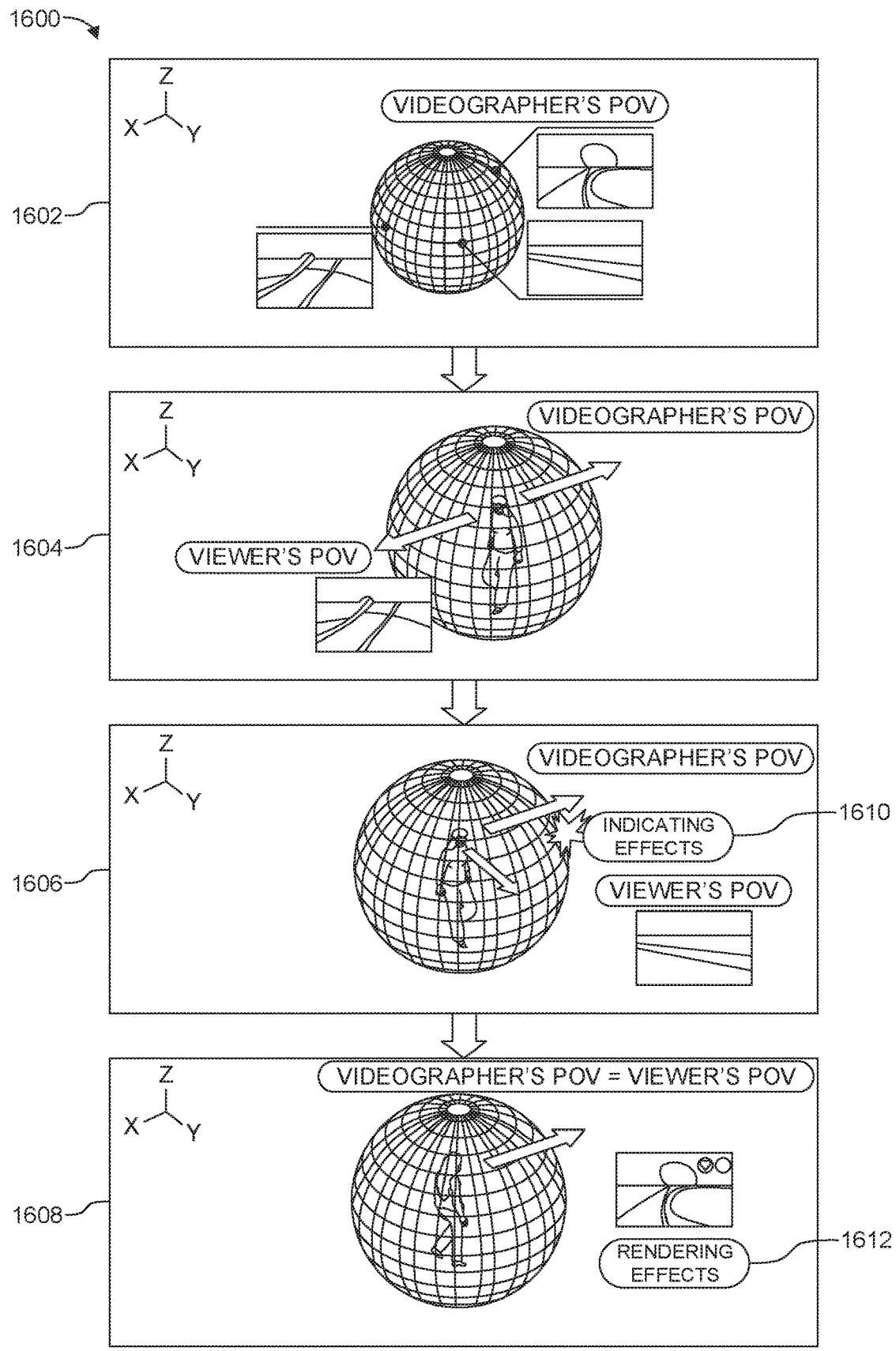
FIG. 16 is a process diagram illustrating an example for displaying indicating and emotional effects based on a viewer's point of view (POV) according to some embodiments.

FIG. 16 is a process diagram illustrating an example for displaying indicating and emotional effects based on a viewers point of view (POV) according to some embodiments. The display process 1600 shows an example start of a scene in the first image 1602. The display process 1600 shows that no effects are provided when a user is facing away (opposite) from the videographer's point-of-view (POV) in the second image 1604. In the third image 1606, the viewer turns towards the videographer's point of view (POV) and indicating effects 1610 guide the viewer towards the videographer's point-of-view (POV). In the fourth image 1608, the viewer's point-of-view (POV) matches the videographer's POV, and emotional effects 1612 communicate the videographer's emotional state (which may be tagged to the frame) to the viewer.

The display process 1600 may commence after rendering the multi-view (e.g., 360-degree) contents based on the videographer's point-of-view. The multi-view (e.g., 360-degree) contents may be recorded with an HMD with multi-view (e.g., 360-degree) camera, eye tracker, biometric sensor and motion sensor for some embodiments. Point-of-view may be determined based on eye tracking information captured during recording for some embodiments. The motion information and the biometric information of the videographer may be recorded while a specific point-of-view focus is maintained, and the sensed motion information and the biometric information may be tagged to a corresponding point-of-view time-sequence. Heart rate data in a time-sequence may be measured (or received) by a biometric sensor of the HMD device. The HMD device may determine whether an input heart rate is high compared to a threshold, such as a moving average. If the input heart rate exceeds the heart rate threshold (such as a moving average) by a threshold amount more than the input heart rate, the time of the increased input heart rate may be tagged to the videographer's point-of-view frame.

The display process 1600 may include providing indicating effects based on the viewer's head direction relative to the videographer's point-of-view. If the viewer's point-of-view is opposite to the videographer's point-of-view, there is no effect on the viewer's point-of-view. If the viewer's head moves towards the videographer's point-of-view, an indicating effect on the viewer's point-of-view is provided to help the viewer see the videographer's point-of-view.

The display process 1600 may include providing emotional effects if the viewer's point-of-view matches the videographer's point-of-view. The biometric information (e.g., heart rate) of the videographer at the time of photographing (or recording a video), which may be tagged in the videographer's point-of-view, is converted into an emotional effect and stored. The HMD device indicates to the viewer biometric information in the form of an emotional effect when the viewer's point-of-view matches the videographer's point-of-view. For example, various outputs (e.g., visual, haptic, or sonic) of the HMD and connected wearable devices worn by the viewer may be used so that the viewer may realize the heartbeat information of the videographer tagged in the videographer's point-of-view (e.g., by flashing a heartrate indicator on the display, pulsing a haptic module, pulsing a sonic sample, and mapping a heart rate to a sonic frequency) for some embodiments. With a haptic module, the time-sequence heart rate data (such as 79, 75, 88, 72, 77, 70, 69, 73, 71, 75, . . . ) may be transformed into a vibrating beat. The vibrating beat may be output via a haptic feedback module that couples with the viewer to indicate the videographer's heart rate.

In FIG. 16, the emotion of the videographer may be communicated by adjusting the brightness and size of the visual information representing the fireworks. In some embodiments, when the fireworks burst, the tagged heart rate is converted and played back as a sound provided to the viewer.

Figure 17:
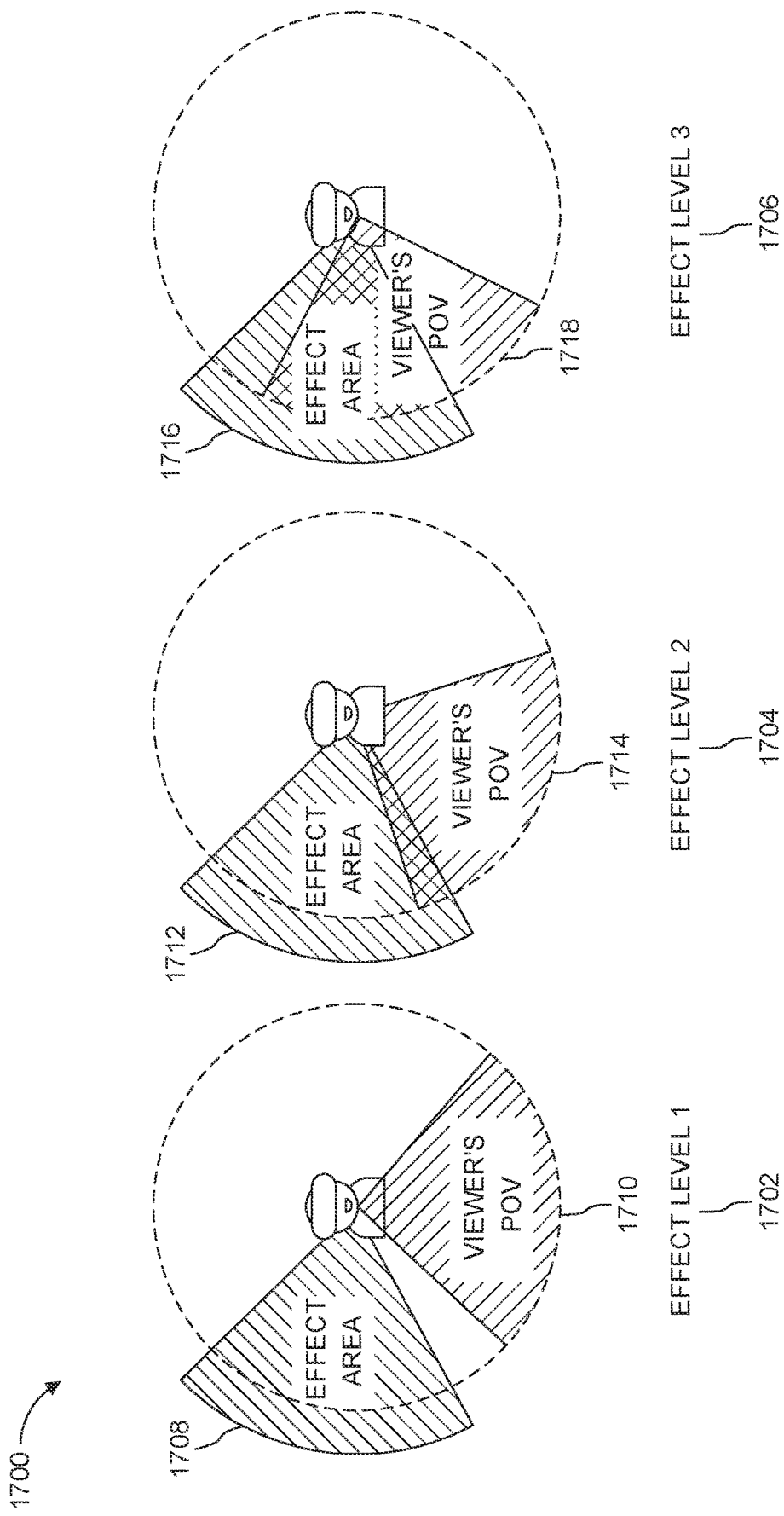
FIG. 17 is a schematic plan view illustrating an example of a gradual effect level based on a viewers point of view relative to an area with an indicating effect according to some embodiments.

FIG. 17 is a schematic plan view illustrating an example of a gradual effect level based on a viewers point of view relative to an area with an indicating effect according to some embodiments. The three depictions show that different point-of-view overlap amounts may be assigned to different effect levels 1702, 1704, 1706. Even if the point-of-view of the videographer and the point-of-view of the viewer do not match exactly, if the user's motion changes toward the point-of-view of the videographer, a biometric-indicating effect may begin subtly or gradually. As the point-of-view of the viewer gets closer to the point-of-view of the videographer, which is shown in the progression of effect levels 1, 2, and 3 (1702, 1704, 1706), the intensity level of the effect may be increased gradually. For example, if the videographer's point-of-view corresponds to the emotion felt by the videographer, which may be communicated to the viewer as a vibration effect, the closer the viewer's point-of-view is to the videographer's point-of-view, the higher the intensity of the vibration for some embodiments.

Figure 18:
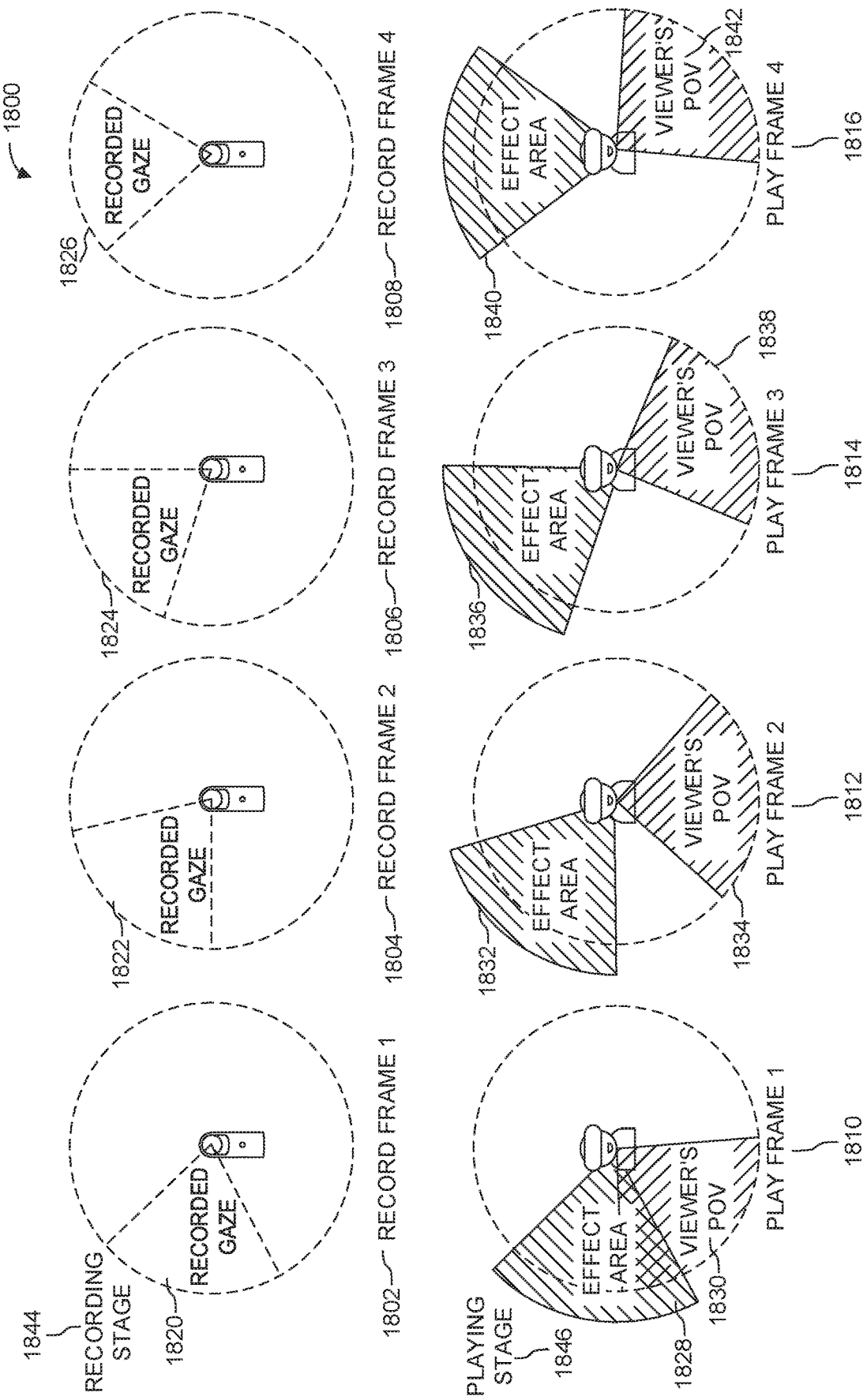
FIG. 18 is a schematic plan view illustrating an example of a gradual effect level based on a viewers point-of-view relative to an area with an indicating effect with recording stage reference images according to some embodiments.

FIG. 18 is a schematic plan view illustrating an example of a gradual effect level based on a viewers point-of-view relative to an area with an indicating effect with recording stage reference images according to some embodiments. For some embodiments of the gradual effect process described in relation to FIG. 17, the system and process herein may determine if the viewer's point-of-view matches the videographer's point-of-view and how close the match is.

FIG. 18 shows for some embodiments a scenario 1800 wherein a user records a multi-view (e.g., 360-degree) video with a camera equipped with an eye tracker. The eye tracker may determine the videographer's point-of-view in the multi-view (e.g., 360-degree) environment, and the frame containing the point-of-view may be rendered to provide an appropriate effect. The videographer's point-of-view information is depicted in the recording stage row 1844. The videographer's eye tracking information with respect to the recording time may be tagged together with the video sequence and stored in the server. The object targeted by the gaze of the videographer may be determined to be an important object in the 360-degree (or multi-view) image. The multi-view (e.g., 360-degree) image may be edited to emphasize the context-wise important frame containing the important object. In other words, context-wise unimportant frames may be diminished visually.

The multi-view (e.g., 360-degree) image from the videographer's viewpoint may be rendered (which may be on a server), and if the videographer or other user subsequently plays the rendered multi-view (e.g., 360-degree) content, the multi-view (e.g., 360-degree) image of the videographer's viewpoint may be effectively provided by providing various effects to context-wise important frames. For example, if a viewer's point-of-view is not a point-of-view that is eye-tracked by the videographer at the time of recording, no significant post-rendering effect is performed for some embodiments. If the point-of-view of the viewer becomes the same as the point-of-view (POV) of the videographer, effects may be provided to the viewer to effectively indicate the important object of the point-of-view. Effect parameters may be modulated at various rates to control the kinds of effects provided and their respective intensities based on the head movement of the user and the distance between point-of-views. A viewer's motion change information includes the viewer's head movement, gaze movement, distance walking (or walking) during multi-view (e.g., 360-degree) viewing. While point-of-views are overlapping, reaction information of the videographer tagged in the viewpoint (point-of-view) specified according to the motion change information of the viewer is outputted through the HMD of the viewer. The playing stage row 1846 of FIG. 18 depicts time-sequence alignments of the viewers POVs 1830, 1834, 1838, 1842.

For the example of FIG. 18, the recording stage row 1844 shows a time sequence of record frames 1-4 (1802, 1804, 1806, 1808) that show the changes to the recorded gaze

1820, 1822, 1824, 1826. The playing stage row 1846 shows a time sequence of play frames 1-4 (1810, 1812, 1814, 1816) that show an effect area 1828, 1832, 1836, 1840 and a viewers POV 1830, 1834, 1838, 1842. The effect areas 1828, 1832, 1835, 1840 of each play frame 1-4 (1810, 1812, 1814, 1816) match the recorded gazes 1820, 1822, 1824, 1826 of record frames 1-4 (1802, 1804, 1806, 1808) for the example shown in FIG. 18.

Table 1 depicts an exemplary table mapping accelerometer data and biometric data to potential emotional states, in accordance with at least one embodiment. The system and process described herein includes providing the videographer's emotion status if the viewer's point-of-view matches the videographer's point-of-view. Table 1 shows an example look-up table that matches sensor data (e.g., ECG and EEG data) to a videographer's emotional state.

TABLE 1

Sensor Data Matched to Emotional States

| Case | Accelerometer | ECG | EEG | Emotional States |
|---|---|---|---|---|
| 1 | Dynamic Movement | 111 bpm | Beta Wave | Happy, Fun, Satisfaction, Achievement |
| 2 | Mild Movement | 86 bpm | Alpha Wave | Calm, Stability, Apathy, Aloofness |
| 3 | Moderate Movement | 133 bpm | Beta Wave | Irritation, Fear, Anger, Fright |

The biometric sensing data and acceleration sensing data tagged in the point-of-view at the time of recording may be determined by the emotion estimation unit of the VR content creator. For some embodiments, the VR content creator may classify the sensed information into at least one emotional state based on an emotion table. The emotion table may be stored in the VR content server. A single emotional state may be selected, for some embodiments, based on the attribute information of the eye-tracked object in the point-of-view. Two or more emotional states may be narrowed into one emotion state by using eye-recognized object information. That is, if biometric and motion sensor data are mapped to more than one emotional state, attribute information of the virtual object that the videographer watches at the time of recording may be used to determine a single emotional state.

The determined emotion may be tagged in the point-of-view, and the tagged emotion information may be provided as an effect (such as a 3D effect) that is a function of the head motion of the viewer. The relative point-of-view difference in the head direction of the viewer and the time-sequence gaze of the videographer may be tracked continually, for some embodiments. If the viewer's point-of-view matches the videographers point-of-view, the videographers emotion tagged in the point-of-view may be provided to the viewer. For some embodiments, a difference between a compass angle associated with a point-of-view (POV) of a viewer and a compass angle associated with a POV of a videographer (or camera operator for some embodiments) may be determined. An effect (such as a visual effect) may be presented to the viewer based on the difference between the viewer's and the videographer's compass angles (or POVs for some embodiments).

For example, for case 1 of Table 1, acceleration sensor (or accelerometer) data is classified as dynamic movement, ECG sensor data is measured as 111 bpm, and EEG sensor data is measured and stored as a beta wave. For case 1, the emotional states are classified a happy, fun, satisfaction, and achievement. These emotions may be condensed into one emotion state based on the attribute information of the context-wise important object recognized by the videographer. Even if similar sensor data is measured, the selected emotional state may be different because of the attributes of the object viewed by the videographer. Cases 2 and 3 may be condensed similarly.

Figure 19:
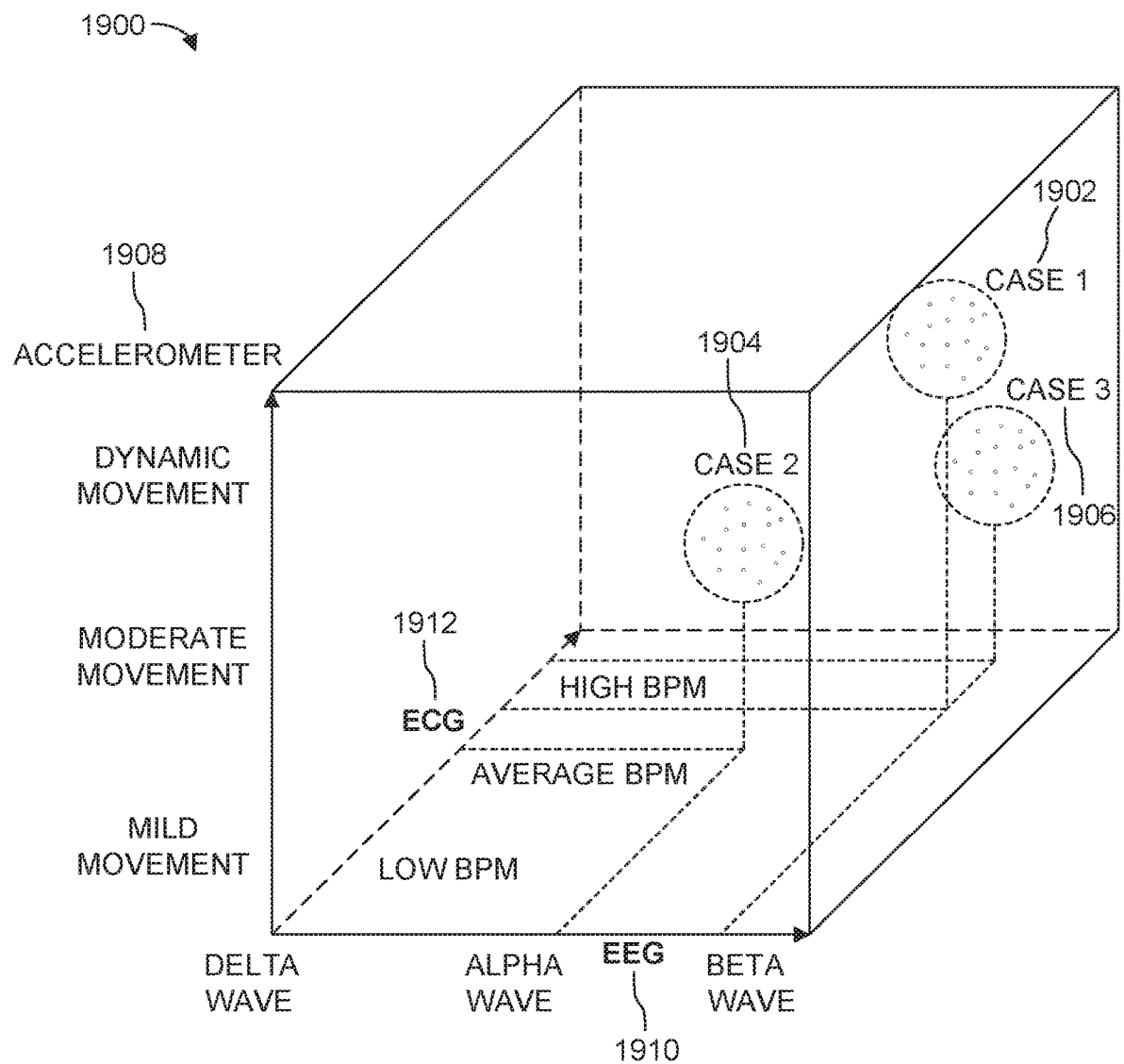
FIG. 19 is a state diagram illustrating an example for identifying a videographers potential emotional state according to some embodiments.

FIG. 19 is a state diagram illustrating an example for identifying a videographers potential emotional state according to some embodiments. As seen in FIG. 19, various ranges of multi-dimensional biometric and acceleration data may be associated with certain emotional states when sensor data results are plotted on linearly independent axes (e.g., three axes are shown in FIG. 19). Each of three sensor data streams (e.g., accelerometer 1908, EEG 1910, and ECG 1912) may be plotted on separate axes to form a state diagram (e.g., a VR emotion cube) (or, a higher order emotional state diagram in the case of more sensor streams). The emotion state of the videographer may be distinguished using a combination of sensor data. The example cases 1, 2, and 3 of Table 1 are plotted on FIG. 19 as cases 1, 2, and 3 (1902, 1904, 1906). The VR content creator may tag the emotional state of the videographer using an emotion table similar to Table 1 and an emotion state diagram similar to FIG. 19. The emotion status information tagged in the point-of-view may be provided to the viewer in the future.

Figure 20:
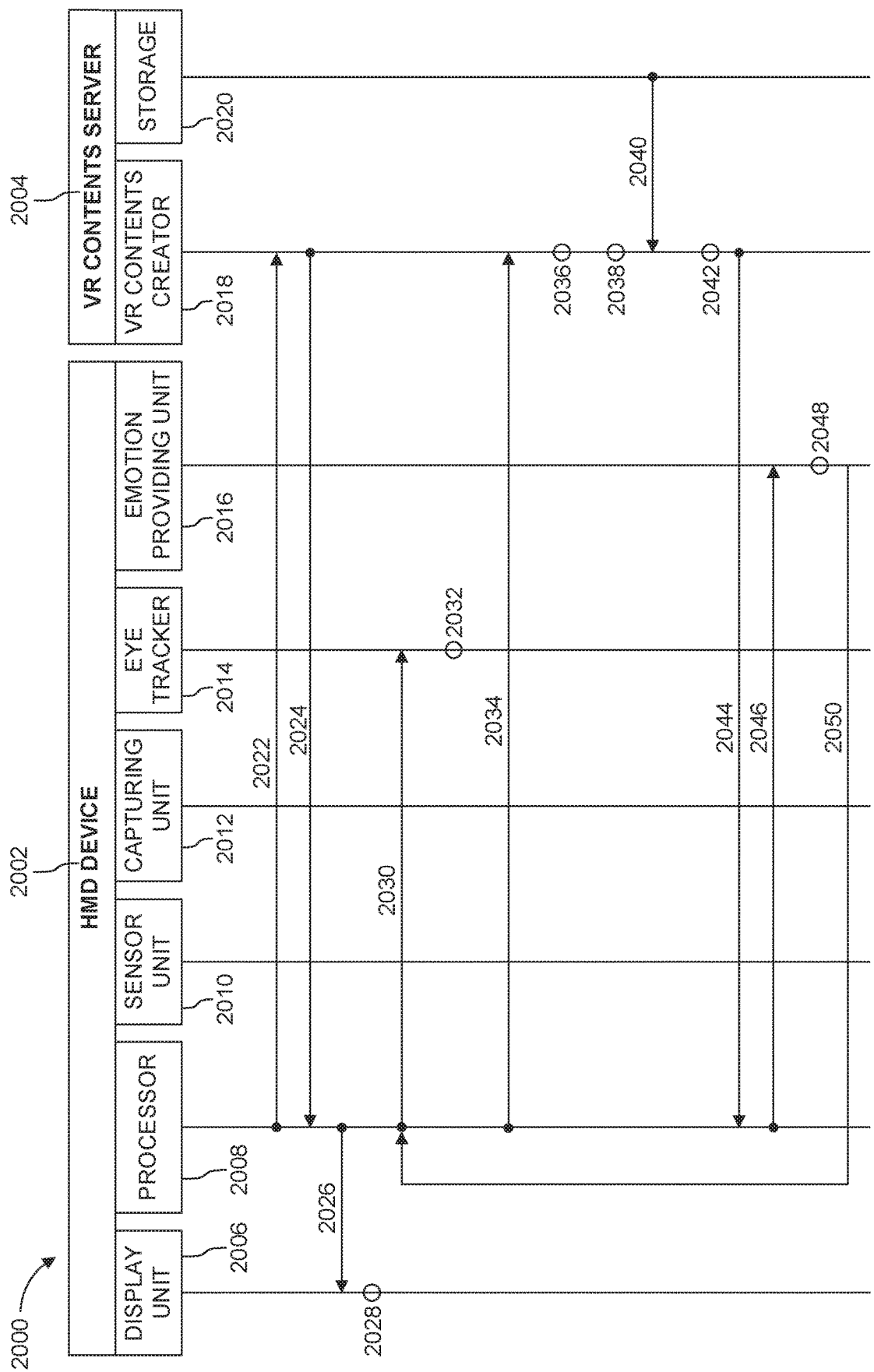
FIG. 20 is a message sequencing diagram illustrating an example process for indicating a videographer's emotional state to a multi-view (360-degree) content viewer according to some embodiments.

FIG. 20 is a message sequencing diagram illustrating an example process for indicating a videographers (e.g., a camera operators) emotional state to a multi-view (360-degree) content viewer according to some embodiments. The message sequence diagram 2000 of FIG. 20 shows an HMD device 2002 that includes, e.g., a display unit 2006, a processor 2008, a sensor unit 2010, a capturing unit 2012, an eye tracker 2014, and an emotion providing unit 2016, as well as a VR contents server 2004 that includes a VR contents creator 2018 and storage 2020 for some embodiments.

The processor 2008 may send 2022 a message to the VR contents creator 2010 requesting the rendered VR content. The processor 2008 may receive 2024 rendered VR content from the VR contents creator 2010. The processor 2008 may send 2026 a message (which may include VR content) to the display unit 2026 to display the rendered VR content, and the rendered VR content may be displayed 2028. The processor 2020 may send 2030 a message to the eye tracker 2014 to measure (or detect for some embodiments) the eye tracking data of the VR content viewer. The viewer's point-of-view may be determined 2032 (or detected for some embodiments) based on the eye tracking data. The viewer's point-of-view data may be transferred 2034 to the VR contents creator 2018. The viewer's point-of-view may be compared 2036 to the videographer's point-of-view by the VR content creator 2010 (or by a point-of-view comparison unit that is connected to (or, e.g., part of) the VR contents creator 2018). If the viewer's point-of-view is determined 2038 to be the same as the videographer's point-of-view, the viewer's personal data may be transferred 2040 to the VR contents creator 2018 from storage 2020. The tagged videographer's emotion data at the point-of-view may be transformed 2042 into emotion output information based on the viewer's personal data. The transformed emotion output data may be transferred 2044 to the HMD's processor 2008. The processor 2008 may send 2046 a message to the emotion providing unit 2016 to provide the transformed emotion output data to the viewer. The emotion output data may be provided 2048 if the viewers point-of-view matches videographer's point-of-view. For some embodiments, the emotion providing unit 2016 may send a message or content to the display unit 2006 based on the transformed emotion output data as one way of providing the emotion output data to the viewer. Steps of this process may be repeated 2050 for some embodiments to provide real-time functionality.

Figure 21:
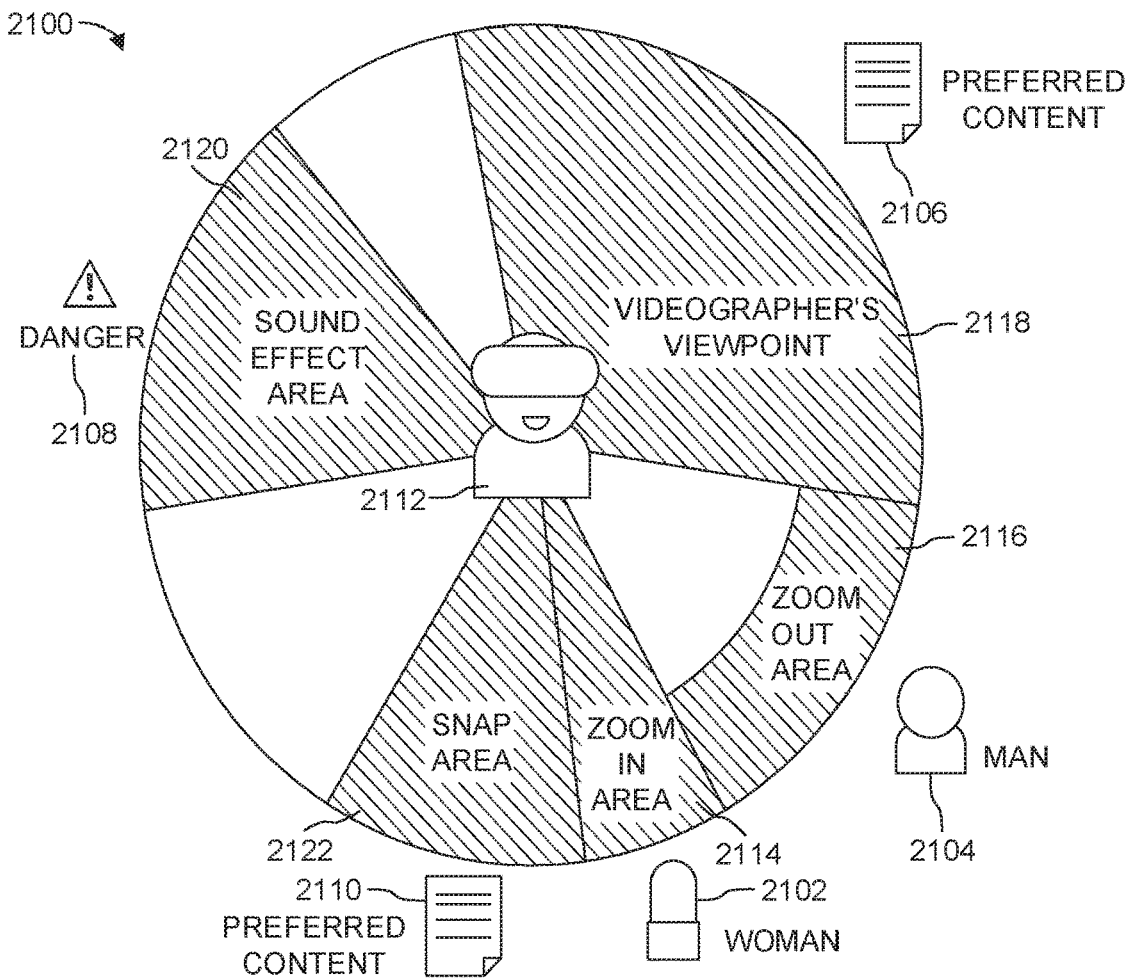
FIG. 21 is a schematic plan view illustrating an example for displaying visual effects based on a viewers point of view (POV) according to some embodiments.

FIG. 21 is a schematic plan view illustrating an example for displaying visual effects based on a viewers point of view (POV) according to some embodiments. FIG. 21 shows an example scene 2100 for a set of effects that may be used to emphasize a context-wise important object or to deliver a videographer's emotion if the viewer's POV matches the videographer's POV. The viewer may recognize the object that the videographer thought important at the time of recording and feel the emotional state as well.

For the example shown in FIG. 21, a user, who may be wearing and viewing video content with an HMD for some embodiments, may experience various effects based on his or her gaze direction. The rendered multi-view (e.g., 360-degree) video may provide various effects according to characteristics of a context-wise important object during playback. The example scene 2100 includes a videographer's viewpoint 2118 having preferred content 2106, a man 2104 within a zoom out effect area 2116, a woman 2102 within a zoom in effect area 2114, preferred content 2110 in a snap effect area 2122, and a dangerous situation 2108 in a sound effect area 2120.

For some embodiments, a first set of preferred content 2106 may be presented to the viewer if the viewers POV overlaps and/or aligns with the videographer's POV 2118. A man 2104 may be displayed with a zoom out effect if the viewers POV overlaps and/or aligns with the zoom out area 2116. A woman 2102 may be displayed with a zoom in effect if the viewer's POV overlaps and/or aligns with the zoom in area 2114. A second set of preferred content 2110 may be presented with a snap effect if the viewer's POV overlaps and/or aligns with the snap area 2122. A sound may be made if the viewer's POV overlaps and/or aligns with a sound effect area 2120 that warns of a dangerous situation 2108.

A viewer wearing the HMD may freely change the viewpoint by moving his or her head, and various effects may be communicated if a context-wise important object exists within the viewpoint (or point-of-view). For example, if a videographer (e.g., a camera operator) falls while viewing an eye-tracked object, the sensor value inputted through a motion sensor (e.g., acceleration sensor or geomagnetic sensor) may be tagged together with the eye-tracked object. The viewer's HMD may output various 3D effects so that the viewer may experience second-hand, e.g., at least some of the five senses of the videographer. A viewer's motion may include all the motions that may change the viewer's viewpoint in a 3D virtual environment, such as physical distance movement, head movement, and gaze movement detected during wearing the HMD.

For some embodiments, if the point-of-view of the viewer overlaps with the point-of-view of the videographer, the biometric information may be transformed into tactile information and provided through an HMD haptic source, and the acceleration information may be provided to the viewer, for example, by converting the acceleration information into visual information or auditory information. Communicating to the viewer the videographer's emotional state, which may be detected based on the videographer's point-of-view of important objects, enables a viewer to have a more immersive virtual reality experience through visual, tactile, and auditory output information. For some embodiments, the intensity of the output modality may be adjusted to an appropriate level so as not to disturb the emotional state of the viewer.

Figure 22:
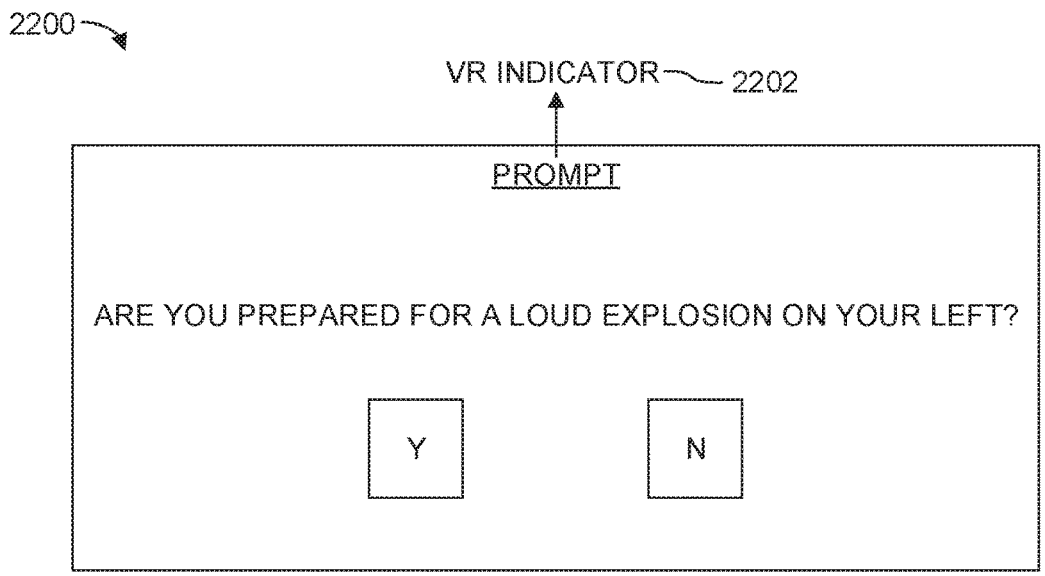
FIG. 22 is an illustration showing an example screenshot of an indicating effect according to some embodiments.

FIG. 22 is an illustration showing an example screenshot of an indicating effect according to some embodiments. For some embodiments, a VR indicator 2202 may be provided to avoid a sudden emotional change at a certain point-of-view. Based on an upcoming tagged videographer emotion, the VR contents server may predict which emotion may be generated by the viewer in a playback interval. Therefore, the HMD may provide a VR indicator 2202 to give an alert based on the viewer's personal information (e.g., profile data or biological data) so as to avoid a sudden emotional feeling or experience. Using motion prediction of the viewer's head and/or activation thresholds based on user data and a movement's speed, direction, or distance from alignment with a point-of-view, a VR indicator may be provided before the viewer's POV matches the tagged POV. The prompt 2200 in FIG. 22 may be overlaid on an HMD display to warm the viewer of a potentially sudden emotional change.

Figure 23:
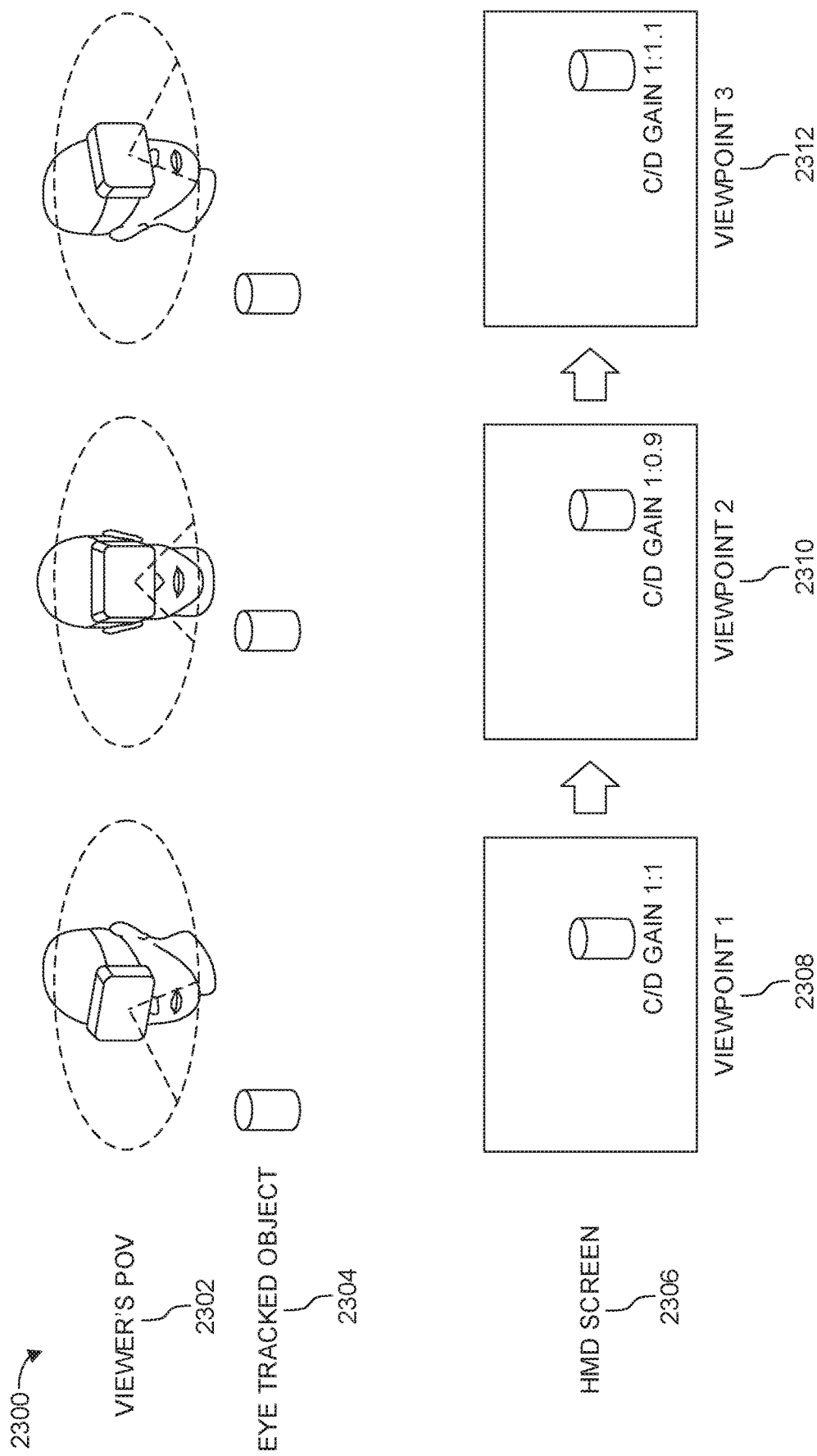
FIG. 23 is a process diagram illustrating an example first emotional effect (friction) according to some embodiments.

FIG. 23 is a process diagram illustrating an example first emotional effect (friction) according to some embodiments. FIG. 23 shows an scenario 2300 for a viewpoint-motion friction effect which adjusts a physical head rotation to virtual viewpoint rotation ratio based on context-wise important frames. For some embodiments, the control and display (C/D) gain of a context-wise important frame, which is classified as important from the eye recognition information of the videographer, may be set to a low ratio, and the C/D gain of a shrunk context-wise unimportant frames may be set to a high ratio. For some embodiments, the total traversable content may be mapped to 360 degrees of physical head rotation by balancing the use of large and small C/D gains.

FIG. 23 shows a series of POVs 2302 of a viewer, eye tracked objects 2304 shown relative to the viewer POV, and HMD screens 2306 seen from the perspective of the viewer. For example, at viewpoint 1 (2308) the viewer's point-of-view is the same as the videographers point-of-view, and the C/D gain may be set to 1:1 (unmodified). If the viewer's POV is changed to viewpoint 2 (2310) via the viewer's head motion, the object is still in the range of vision of the viewer although near to the right side of the HMD screen from the viewer's perspective. The C/D gain may be set to 1:0.9 to induce the viewer to view important objects. The C/D gain of viewpoint 2 (2310) may decrease (or "slow down") the rate of rotation in the virtual environment in comparison with the rate of rotation in the physical environment. In viewpoint 2 (2310), the friction effect causes the location of important objects (e.g., object(s) 2304) to be closer to a center gaze line as than the objects otherwise would be. If the viewer's POV (or head motion) is changed to viewpoint 3 (2312), the object 2304 is now out of the viewers POV. The C/D gain may be set to 1:1.1 to compensate for the low C/D gain in viewpoint 2 (2310), however, and the object 2304 is now rendered within the HMD screen despite being beyond the viewer's POV. Using these C/D gains enables a 360-degree head rotation in the physical environment to correspond to a 360-degree (or overall traversable range) viewpoint rotation in the virtual environment.

Figure 24:
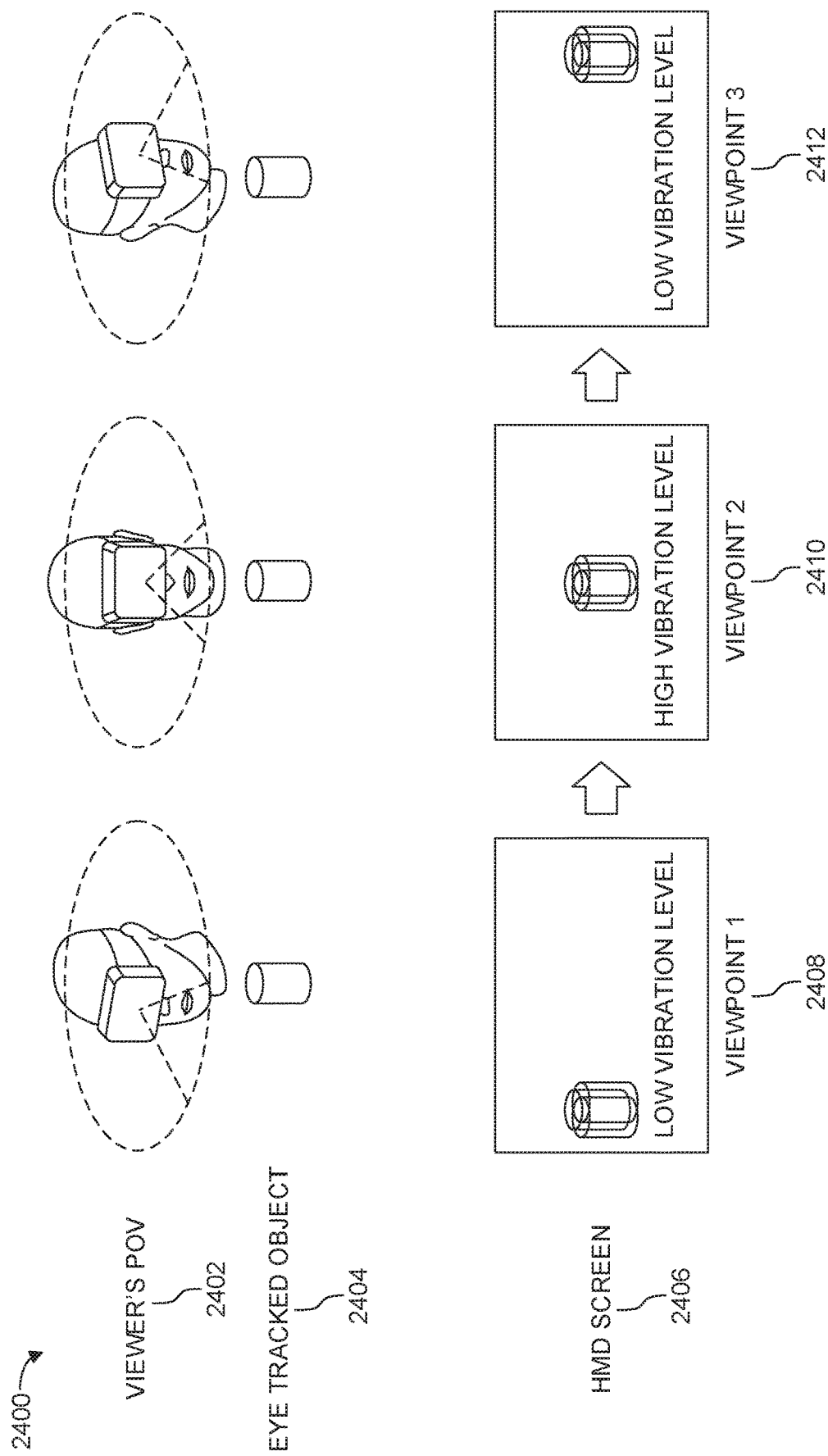
FIG. 24 is a process diagram illustrating an example second emotional effect (vibration) according to some embodiments.

FIG. 24 is a process diagram illustrating an example second emotional effect (vibration) according to some embodiments. FIG. 24 shows an scenario 2400 for a vibration effect for indication biometric sensor data. FIG. 24 shows a series of viewer's POV 2402, eye tracked objects 2404, and HMD screens 2406. Haptic feedback pulses may be used to indicate a measured pulse rate of the videographer by pulsing in-sync with the pulse rate. The vibration intensity is increased and decreased based on an alignment of point-of-views for viewpoints 1-3 (2408, 2410, 2412).

A biometric sensor may be used to measure the biometric information of the videographer (e.g., camera operator) at the time of recording. For some embodiments, the HMD, worn by the viewer, may output visual indications of the biometric reading through a motor to allow the viewer to physically experience the biological response to the eye tracked object. For example, if the videographer sensed excitement when viewing an object, which may be measured by a biometric sensor, and if the viewer's head is pointing at the viewpoint containing the object, an analog to the biometric sensor signal may be sent through a haptic motor. If the viewer point-of-view is the same as the videographer's point-of-view, the vibration effect may be set to a maximum intensity. As the viewer's point-of-view gets farther from the videographer s point-of-view, the intensity level of the vibration effect may be lowered gradually.

As applied to the example of FIG. 24, as the object(s) 2404 are further to the right or the left of the viewers POV, the level of vibration decreases, as opposed to when the object(s) are, e.g., centered within (or closer to the center of) the viewer's POV, the vibration level increases.

Figure 25:
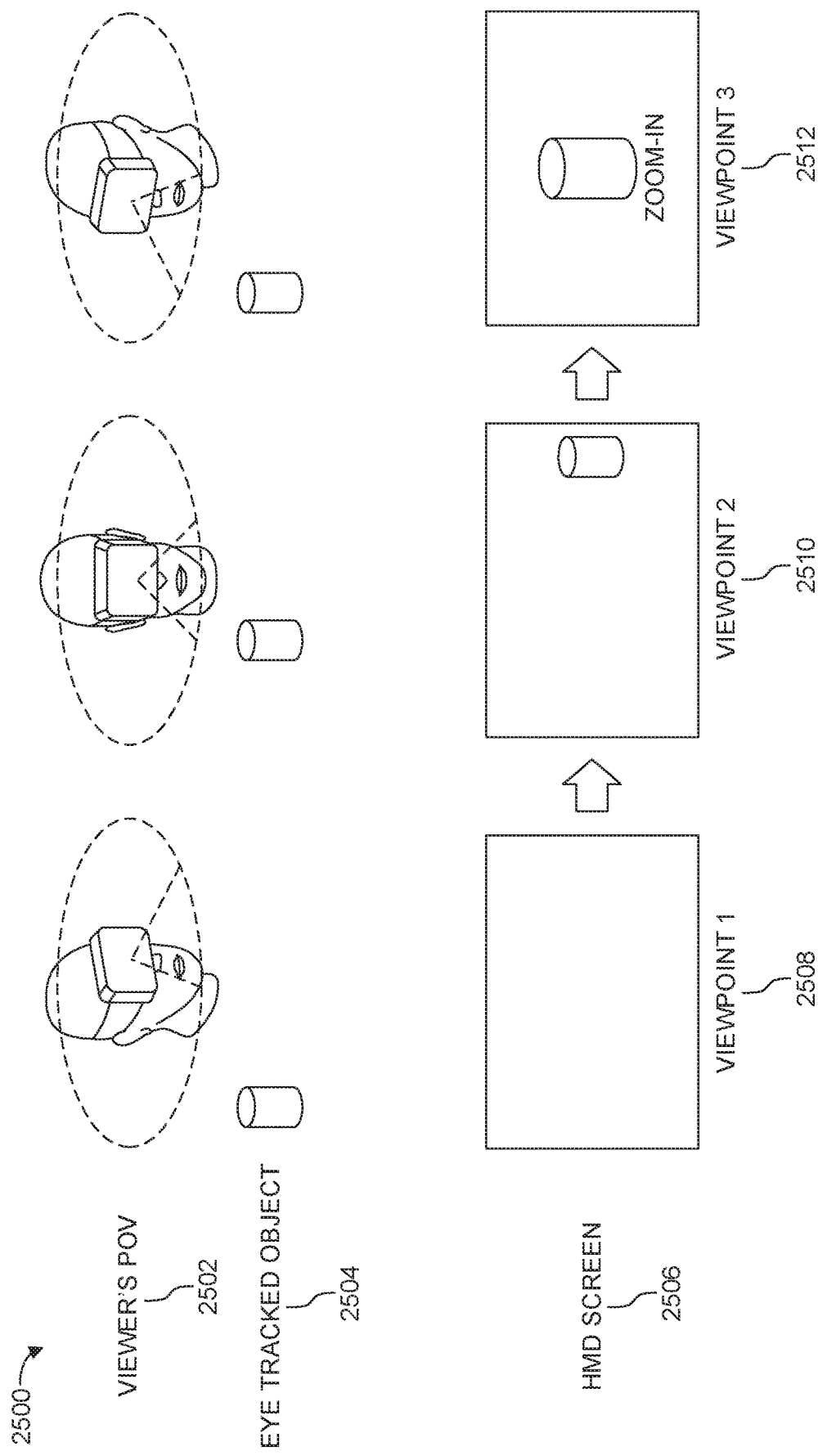
FIG. 25 is a process diagram illustrating an example third emotional effect (zooming) according to some embodiments.

FIG. 25 is a process diagram illustrating an example third emotional effect (zooming) according to some embodiments. FIG. 25 shows an scenario 2500 for a zoom effect. FIG. 25 shows a series of viewer's POV 2502, eye tracked objects 2504, and HMD screens 2506. As the viewer rotates his or her head in changing POV from viewpoint 1 to 2 (2508, 2510), an eye tracked object comes into view. If the viewer's point-of-view is the same as the videographer's point-of-view (viewpoint 3 (2512)), the display may zoom in on an object of importance (or eye tracked object). This effect may allow the viewer to extract greater detail from the object of interest. In some embodiments, the zoom effect may be controlled manually by the viewer via a user interface. For some embodiments, if the viewer is looking at a zoomed-in context-wise important object, other visual/auditory/tactile emotion effects may be presented by the HMD (such as outputting biometric information of the videographer measured at the time of recording).

Figure 26:
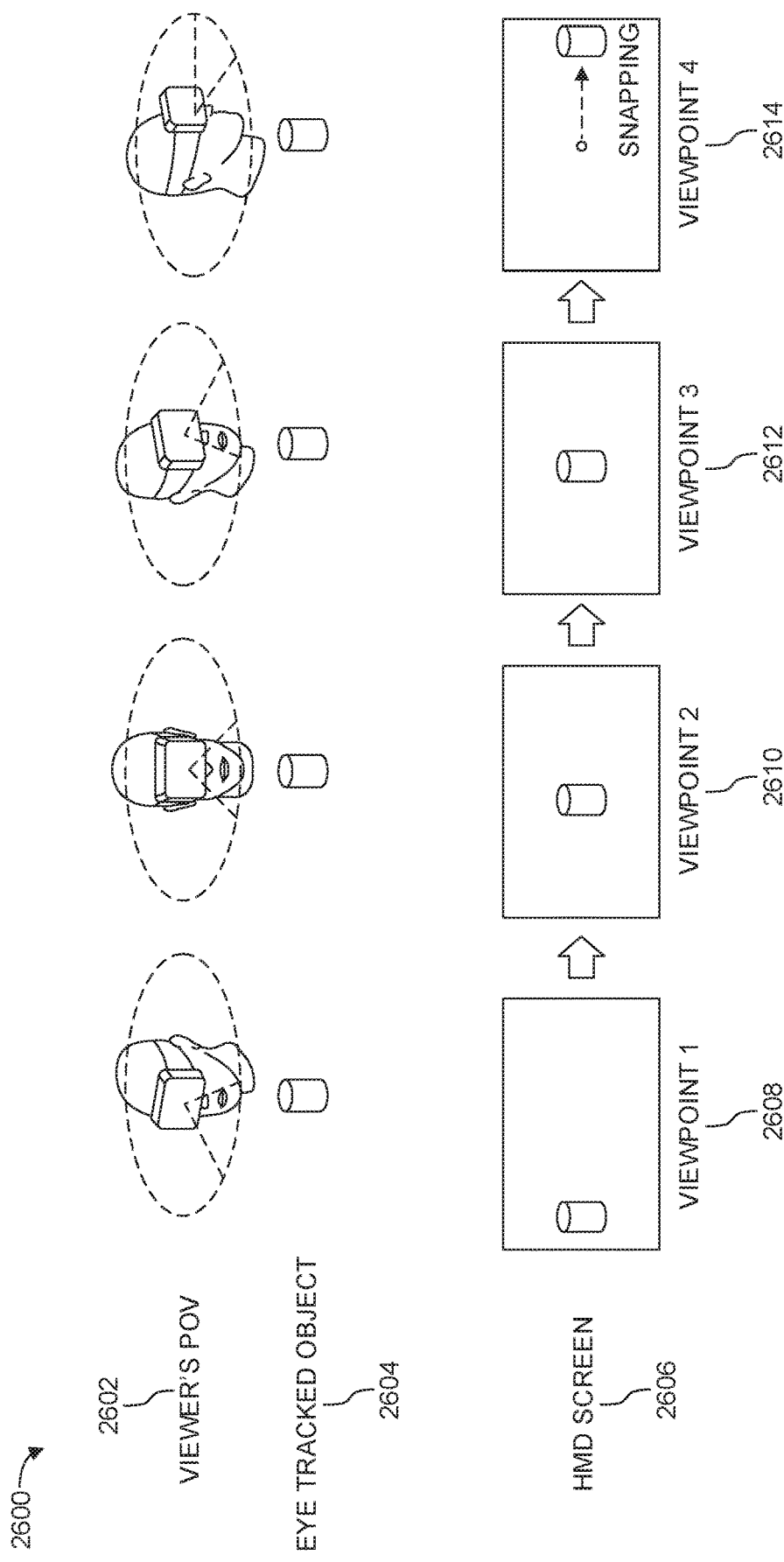
FIG. 26 is a process diagram illustrating an example fourth emotional effect (snapping) according to some embodiments.

FIG. 26 is a process diagram illustrating an example fourth emotional effect (snapping) according to some embodiments. FIG. 26 shows an scenario 2600 for a snap effect for holding a context-wise important object in the middle of the display. FIG. 26 shows a series of viewer's POV 2602, eye tracked objects 2604, and HMD screens 2606. In viewpoint 1 (2608), an object of interest appears on the left side of the screen. In viewpoint 2 (2610), the viewer's point-of-view is the same as the videographer's point-of-view. In viewpoint 3 (2612), the viewer's point-of-view has an overlap area with the videographer's point-of-view, and the eye-tracked object is displayed in the center of the screen. In viewpoint 4 (2614), the viewer's gaze direction is away from the eye-tracked object, and the object of interest snaps back to the center of the display. This snapping effect may cause the context-wise important object to be displayed for a longer time and enable a viewer to align more quickly with the videographer's perspective. Many variations may be used. In some embodiments, the object of interest retains a center position in the display even as the viewers POV changes. In some embodiments, the object of interest initially moves with or in response to a change in the viewer's POV and then "snaps" back to, e.g., a center position in the display. In some embodiments, the object of interest initially moves out of view consistent with the viewer's POV change but then "snaps" back to, e.g., a center or rightward position in the display.

Figure 27:
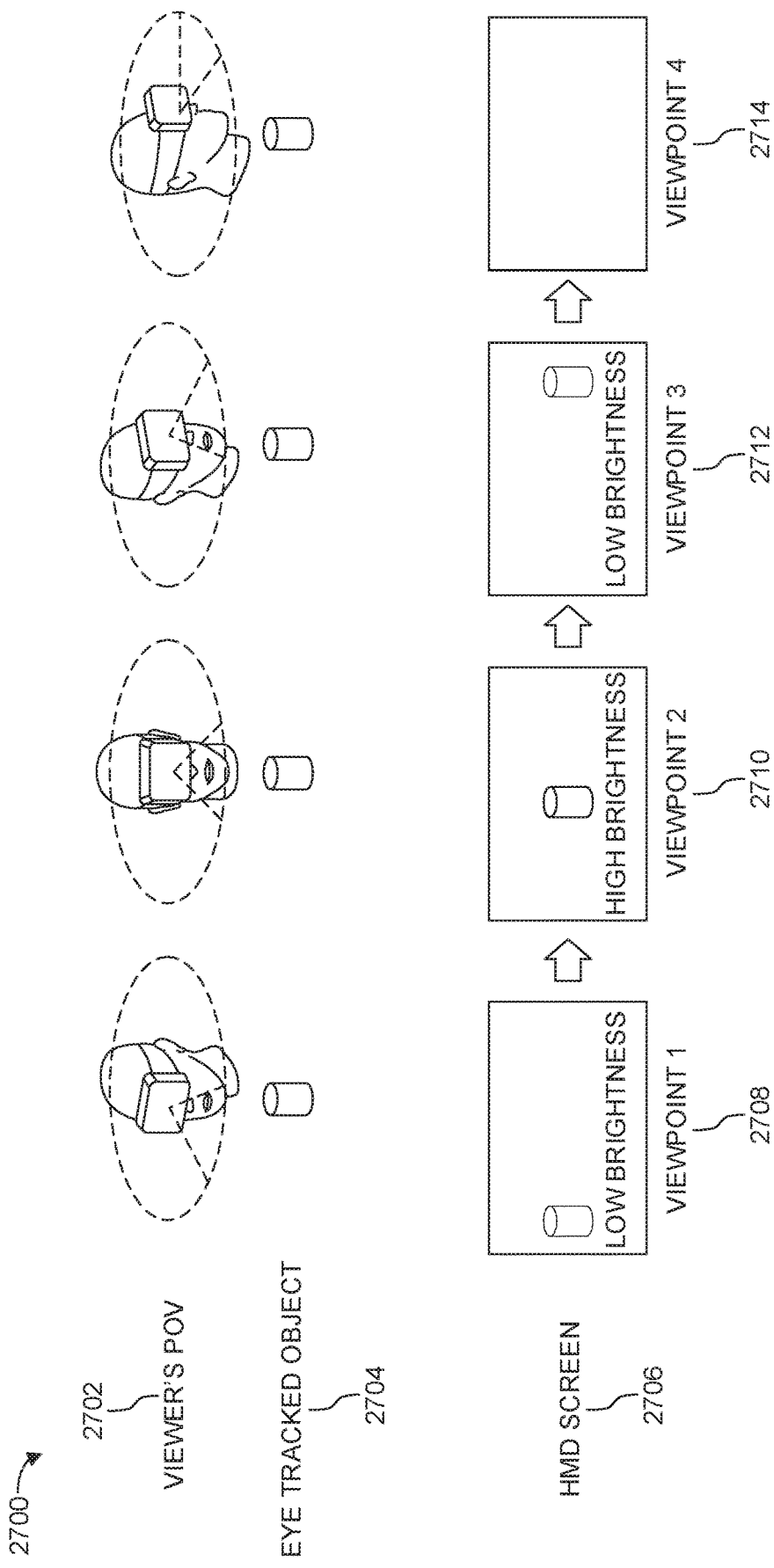
FIG. 27 is a process diagram illustrating an example fifth emotional effect (brightness) according to some embodiments.

FIG. 27 is a process diagram illustrating an example fifth emotional effect (brightness) according to some embodiments. FIG. 27 shows an scenario 2700 for a gradual brightness effect which intensely brightens an important object when point-of-views are closely aligned and softly brightens the important object when point-of-views are partially aligned. FIG. 27 shows a series of viewers POV 2702, eye tracked objects 2704, and HMD screens 2706. In viewpoint 1 (2708) and viewpoint 3 (2712), which are peripheral viewpoints of viewpoint 2 (2710), the intensity of the brightness may be set to a mid-level value. For viewpoint 2 (2710), the intensity of the brightness may be set to a high value. For viewpoint 4 (2714), the brightness may be set to a low value because the eye tracked object is no longer in view. By controlling the intensity of the brightness of the object, the viewer may change his or her POV to match the POV of the videographer. For some embodiments, the applied brightening effect intensity may be a function of the size of the area of overlap between the viewers point-of-view and the videographer's point of view.

Figure 28:
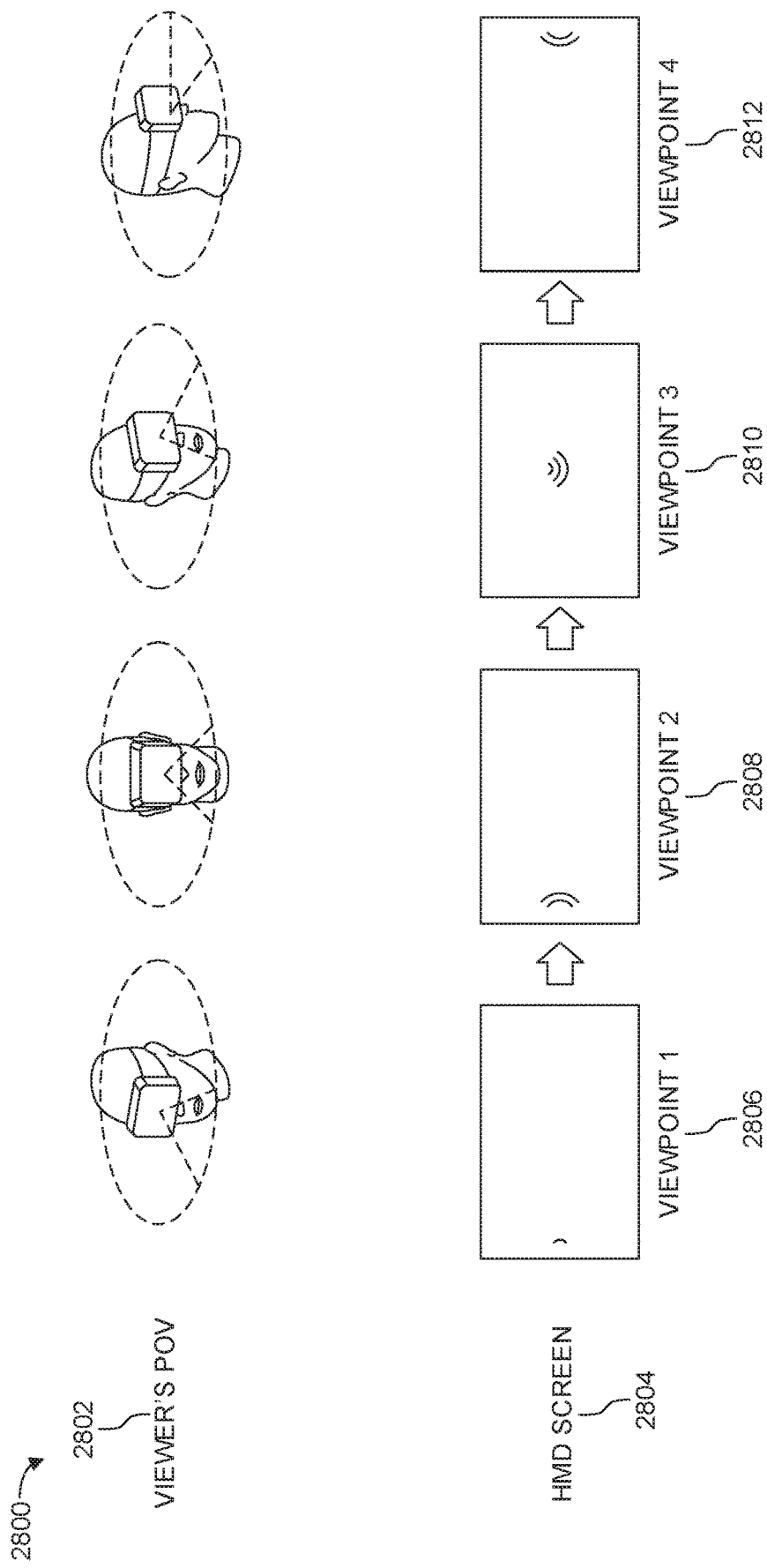
FIG. 28 is a process diagram illustrating an example sixth emotional effect (audio) according to some embodiments.

FIG. 28 is a process diagram illustrating an example sixth emotional effect (audio) according to some embodiments. FIG. 28 shows an scenario 2800 of a sonic effect that is output via an earpiece or speaker of, e.g., a viewers HMD. FIG. 28 shows a series of viewers POV 2802 and HMD screens 2804. During multi-view (e.g., 360-degree) video recording, ambient and directional sound information may be measured and tagged using a microphone and a tagging methodology. If viewing the multi-view (e.g., 360-degree) video, playback of the recorded sound may be activated as the viewer looks towards the eye-tracked object. For some embodiments, the recorded sound may be played in advance of complete viewpoint overlap to induce the viewer to focus towards an eye-tracked object. For some embodiments, as the viewer's point-of-view aligns with the videographers point-of-view, the HMD may increase the volume of the related sound. For the example of FIG. 28, the volume of the sound may be increased as the viewer's POV changes from viewpoint 1 (2806) to viewpoint 2 (2808) to viewpoint 3 (2810). For viewpoint 4 (2812), the viewer's POV moves away from the videographers POV, and the volume of the sound may be decreased. Some embodiments may convert biometric information (e.g., pulse rate data stream) captured at the time of recording into sound information. Pulse rates may be played through the HMD speaker as a synchronous rhythm of beeps. The recorded psychological state of the videographer may be synchronized to a physical sensation experienced by the viewer in real-time.

Figure 29:
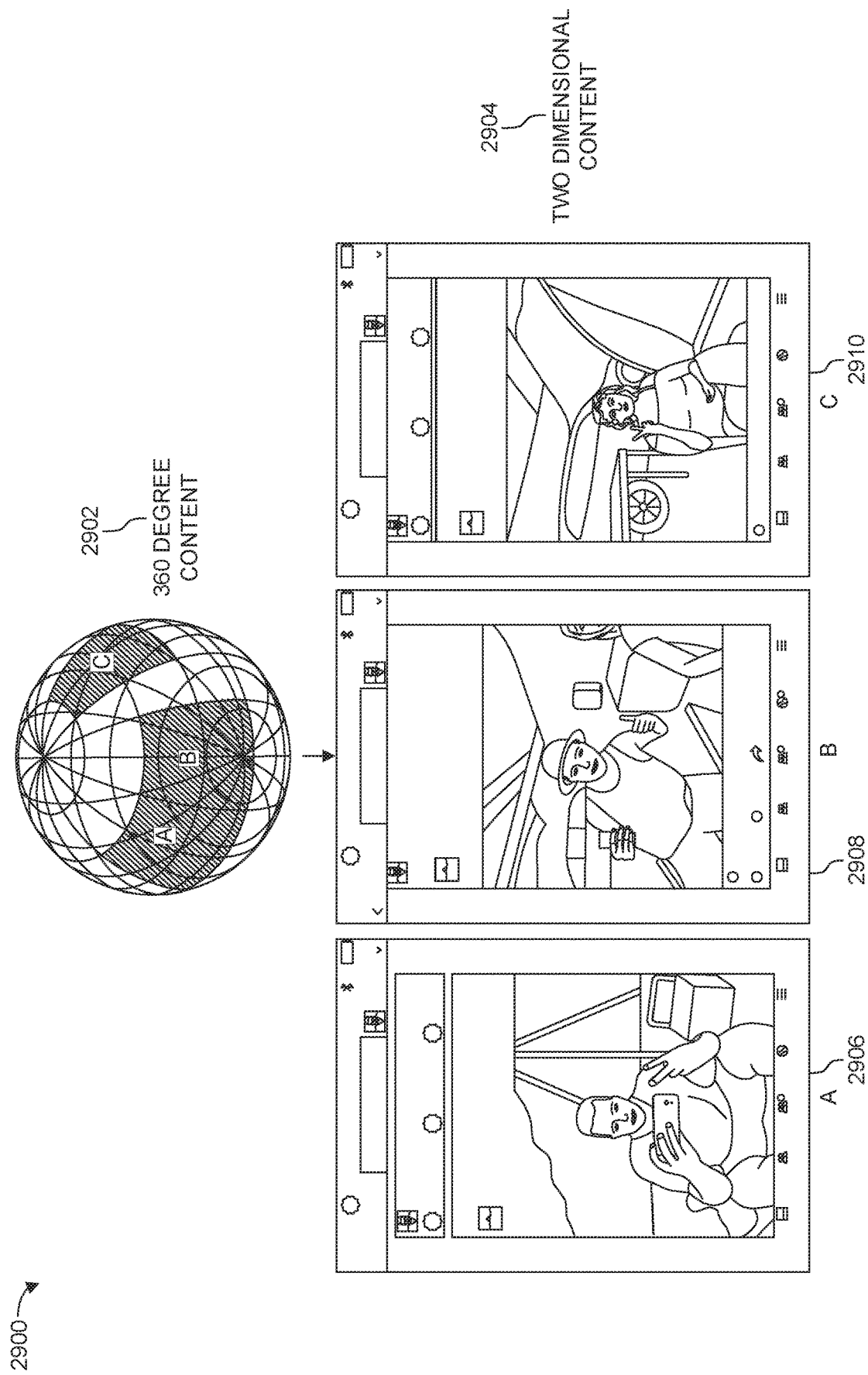
FIG. 29 is a process diagram illustrating an example for segmenting multi-view (e.g., 360-degree) video content into 2D images based on eye recognition according to some embodiments.

FIG. 29 is a process diagram illustrating an example for segmenting multi-view (e.g., 360-degree) video content into 2D images based on eye recognition according to some embodiments. For some embodiments, 2D frames 2906, 2908, 2910 of image and/or video data may be segmented and extracted from multi-view (e.g., 360-degree) content 2902. The various 2D data may be published to a social media service or cloud storage, for example. In FIG. 29, portions A, B, and C of multi-view (e.g., 360-degree) content 2902 may be extracted and respectively converted into 2D content 2904, such as images A (2906), B (2908), and C (2910). For some embodiments, a processor may tag the 2D content 2904 based on the eye tracking and other information captured when the videographer (e.g., a camera operator) recorded the multi-view (e.g., 360-degree) content.

Figure 30:
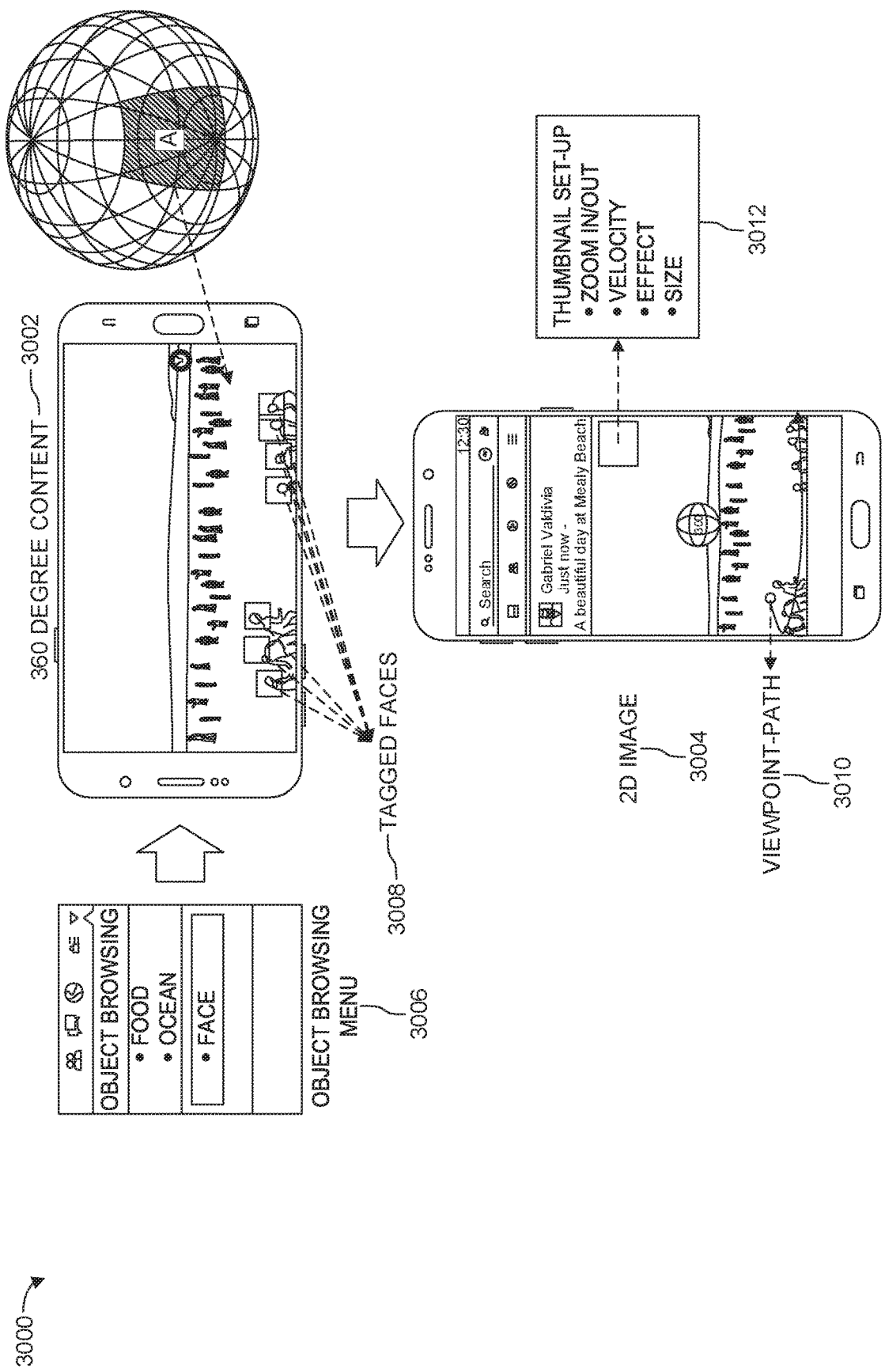
FIG. 30 is a process diagram illustrating an example for selecting 2D images from multi-view (e.g., 360-degree) video content based on detected eye-tracked objects for social media upload according to some embodiments.

FIG. 30 is a process diagram illustrating an example for selecting 2D images from multi-view (e.g., 360-degree) video content based on detected eye-tracked objects for social media upload according to some embodiments. For some embodiments of a process 3000, an object browsing menu 3006 may present a user with a listing of identified and tagged objects 3008 in multi-view (e.g., 360-degree) content 3002. A tagged object may be selected to derive a 2D content type, such as a 2D image 3004. The user may post the 2D static or dynamic thumbnail image on social media, superimposed onto a 2D view of the multi-view (e.g., 360-degree) content. Points of interest and other important objects may be tagged via an object browsing function. A thumbnail may be generated for a tagged object and various thumbnail properties may be set up by using a GUI 3012 (such as a menu) accessed via the thumbnail.

For some embodiments, the processor may perform an eye recognition algorithm on spherical image A to identify spatial locations of one or more objects displayed in the multi-view (e.g., 360-degree) content. The viewpoint of the thumbnail may be changed based on the tagged eye recognition to imitate the point-of-view of those individuals. The user also may adjust the properties of the viewpoint-path 3010 in the thumbnail, such as trace of movement, velocity of movement, depth of tagged object, or other motion effects. The output of thumbnail is adaptively provided corresponding to the adjusted properties of the viewpoint-path. The thumbnail is designed to enhance a users immersive experience.

Figure 31:
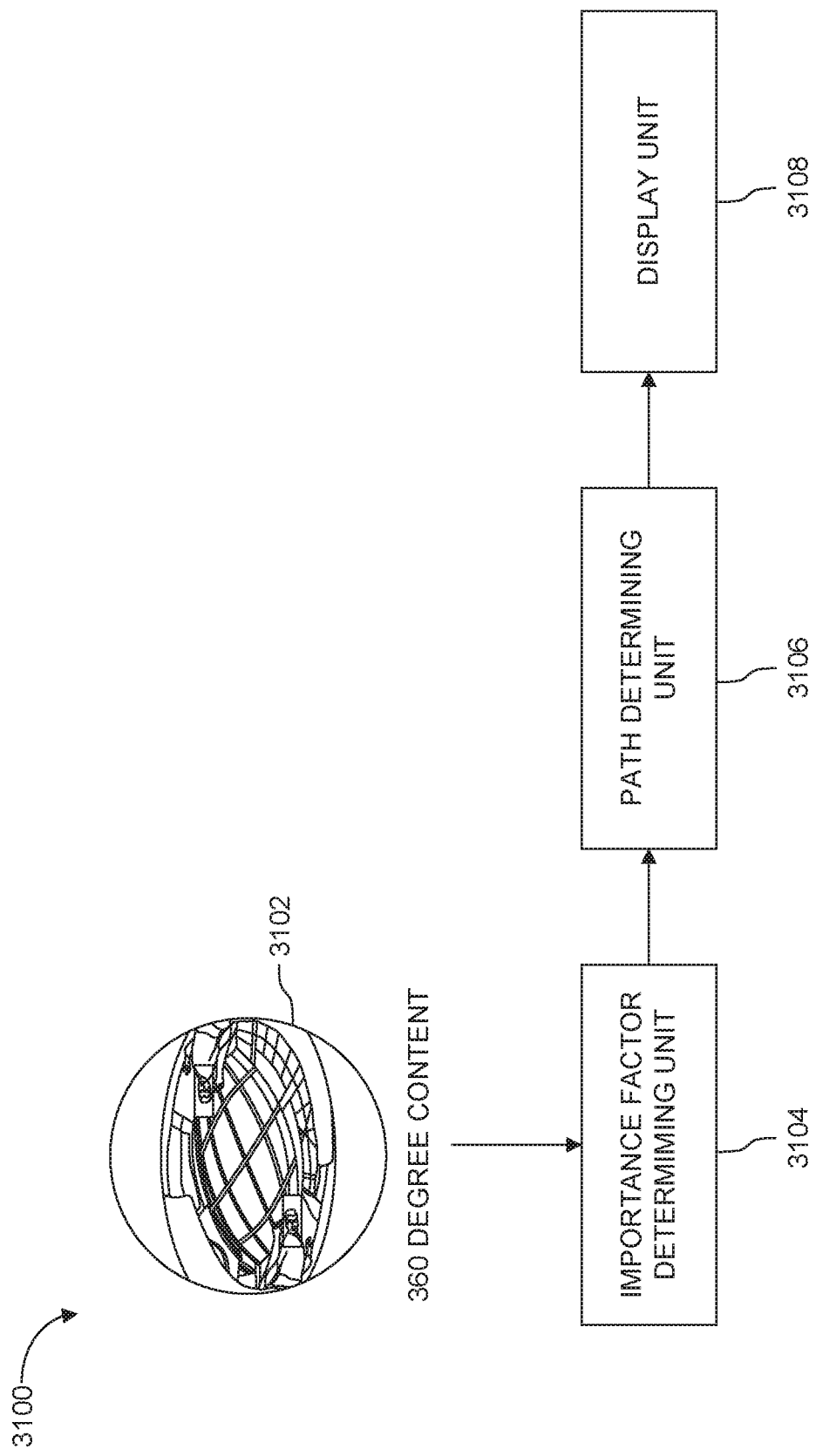
FIG. 31 is a process diagram illustrating an example for determining a viewpoint-path according to some embodiments.

FIG. 31 is a process diagram illustrating an example for determining a viewpoint-path according to some embodiments. For some embodiments, multi-view (e.g., 360-degree) content 3102 may be an input to an importance factor determining unit 3104 (or process). This unit 3104 may identify important and unimportant objects and frames using, e.g., methods disclosed herein in accordance with some embodiments. A path determining unit 3106 may select a starting viewpoint (and/or speed, acceleration, or zoom in/out scale) based on locations of important and unimportant objects. This information may be sent to a display unit 3108, which may present the data to the user accordingly.

Figure 32:
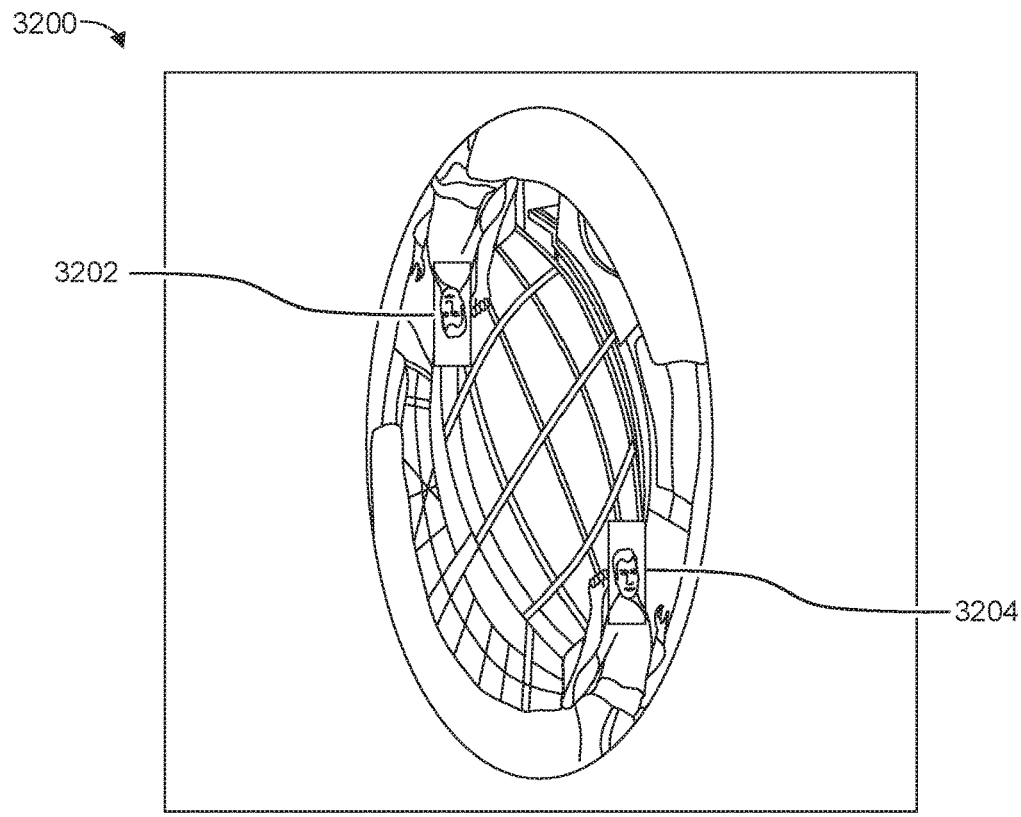
FIG. 32 is an illustration showing an example multi-view (e.g., 360-degree) scene with two objects identified as important according to some embodiments.

FIG. 32 is an illustration showing an example multi-view (e.g., 360-degree) scene with two objects identified as important according to some embodiments. For the example environment 3200 of FIG. 32, the identified important objects 3202, 3204 are the faces of two karate competitors. Each of the competitors' face may be tagged during the video recording session as the competitor's faces each were deemed important based on the videographers gaze and physiological reaction.

Figure 33:
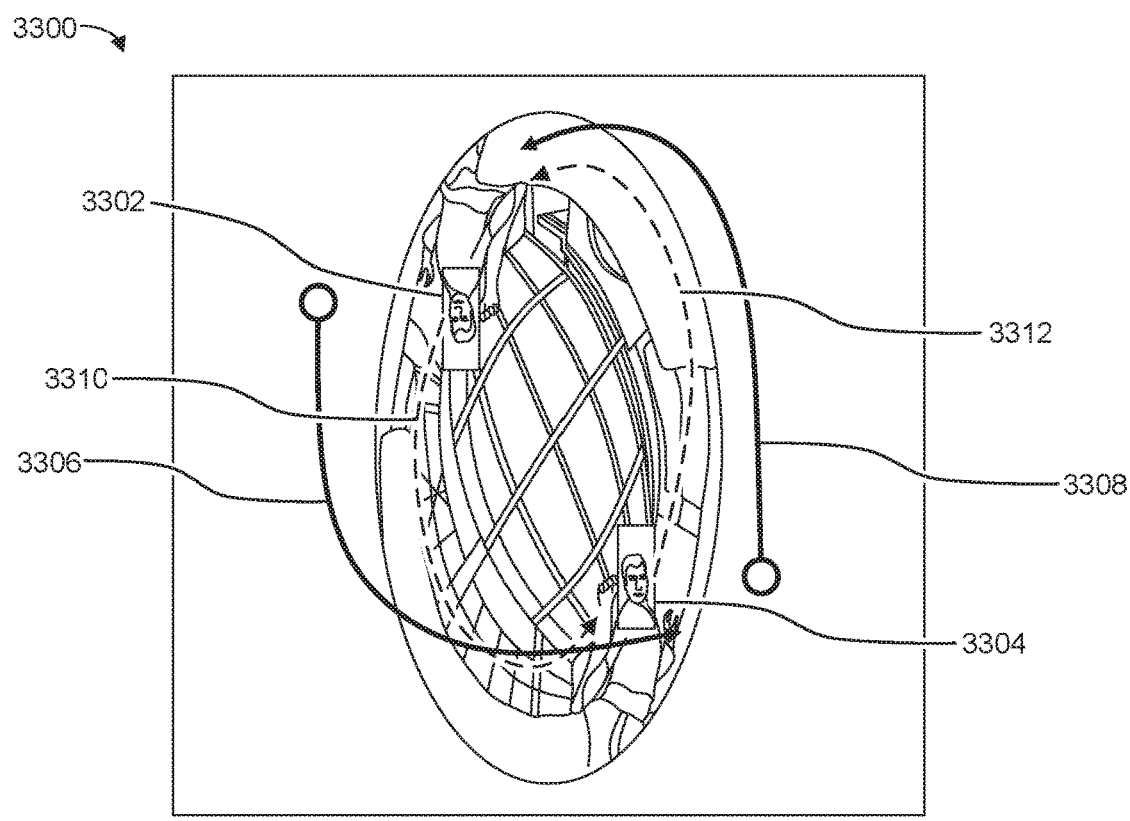
FIG. 33 is an illustration showing the example multi-view (e.g., 360-degree) scene of FIG. 32 and indicating the viewpoint paths of the two identified objects according to some embodiments.

FIG. 33 is an illustration showing the example multi-view (e.g., 360-degree) scene of FIG. 32 and indicating the viewpoint paths of the two identified objects 3302, 3304 according to some embodiments. In FIG. 33, a path finder process may set the viewpoint paths 3306, 3308 based on the eye tracking information (which may indicate the eye tracking paths 3310, 3312) of the videographer. The eye tracking paths 3310, 3312 show the path of the focal points of the videographer's eyes during recording. The viewpoint paths 3306, 3308 indicate the paths of the cameras used to record the multi-view (or 360-degree) video.

Figure 34:
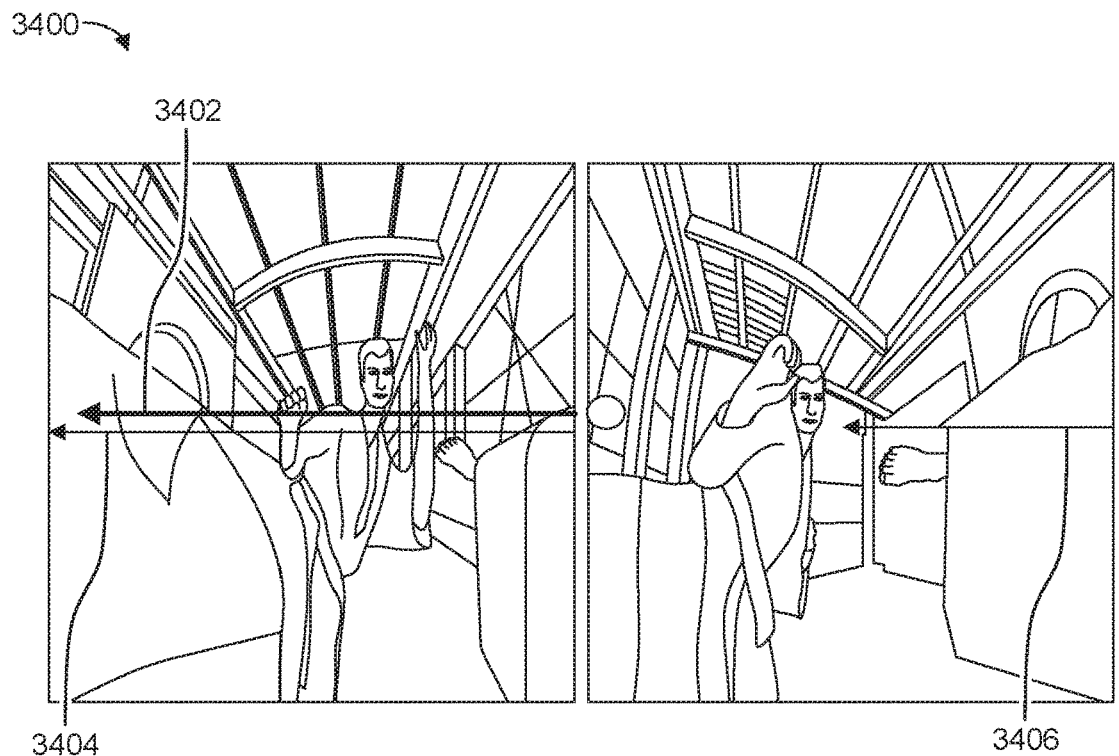
FIG. 34 is an illustration showing the example multi-view (e.g., 360-degree) scene of FIG. 32 as viewed from a starting point of the first viewpoint path according to some embodiments.

FIG. 34 is an illustration showing the example multi-view (e.g., 360-degree) scene of FIG. 32 as viewed from a starting point of the first viewpoint path according to some embodiments. The display unit may play the multi-view (e.g., 360-degree) contents 3400 from a determined starting point (indicated by a circle) of the first viewpoint 3402 and may change the perspective according to the first path 3404, 3406 generated by a path determining unit.

Figure 35:
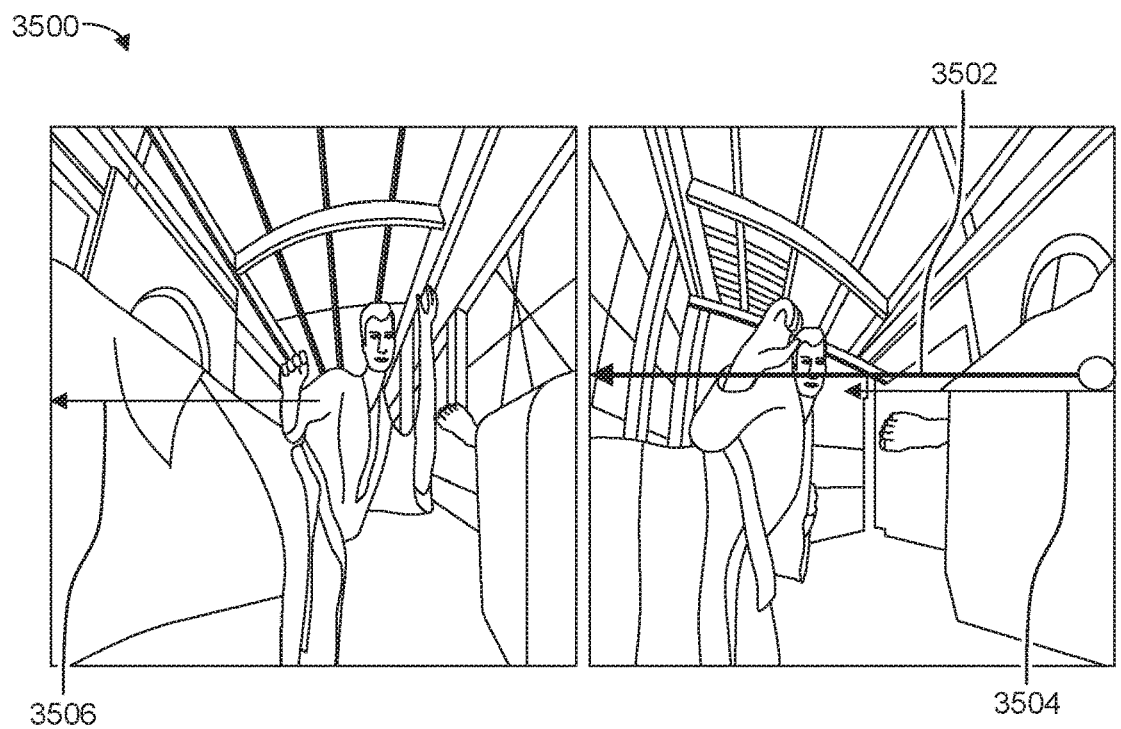
FIG. 35 is an illustration showing the example multi-view (e.g., 360-degree) scene of FIG. 32 as viewed from a starting point of the second viewpoint path according to some embodiments.

FIG. 35 is an illustration showing the example multi-view (e.g., 360-degree) scene of FIG. 32 as viewed from a starting point of the second viewpoint path according to some embodiments. The display unit may play the multi-view (e.g., 360-degree) contents 3500 from a determined starting point (indicated by a circle) of the second path 3502 and changes the perspective according to the second path generated by the path determining unit.

Figure 36:
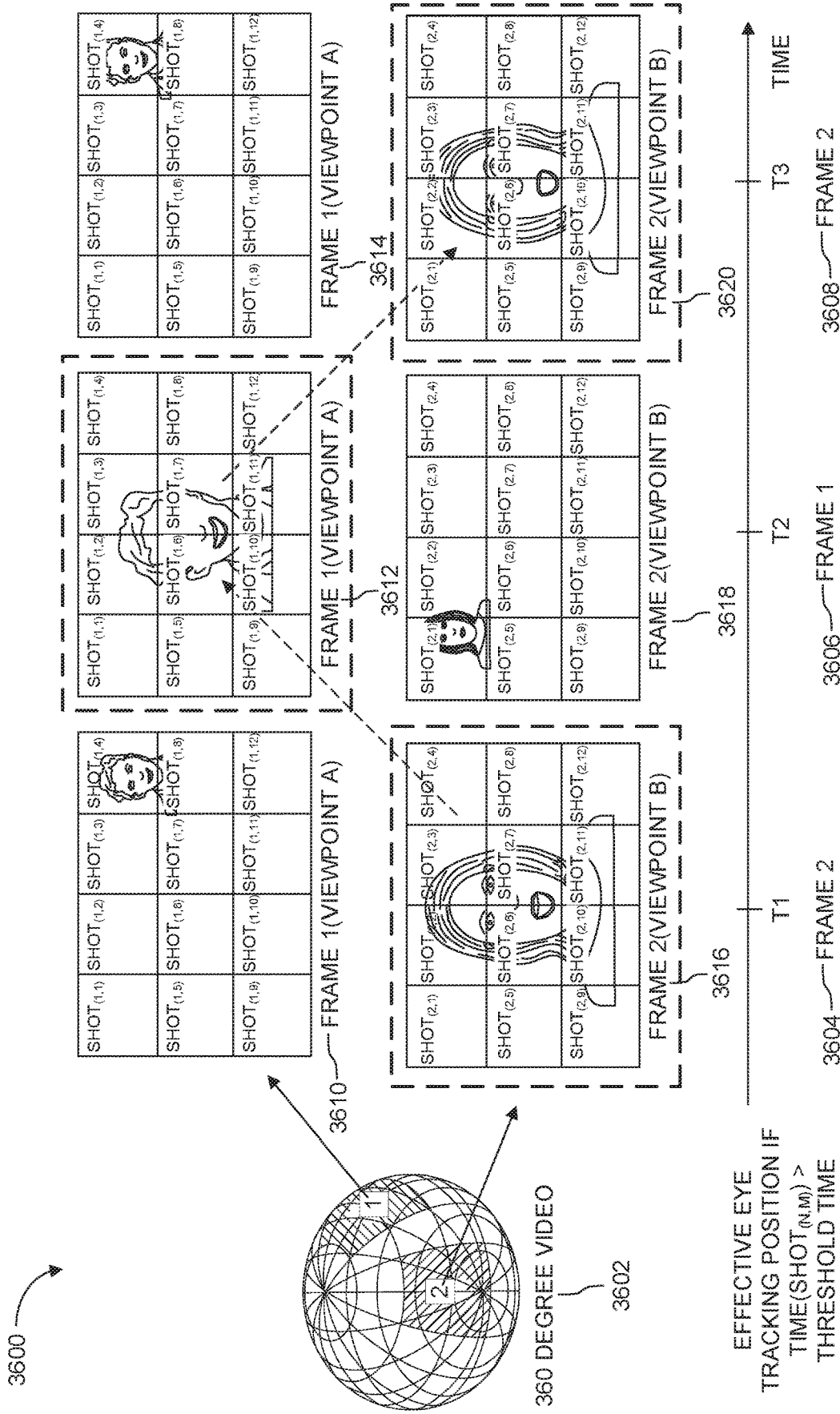
FIG. 36 is a process diagram illustrating an example of aligning a viewers point of view (POV) with an object of interest at the start of playback and other POVs during playback according to some embodiments.

FIG. 36 is a process diagram illustrating an example of aligning a viewers point of view (POV) with an object of interest at the start of playback and other POVs during playback according to some embodiments. In FIG. 36, a multi-view (e.g., 360-degree) video 3602 includes important portions 1 and 2 depicting a man and a woman, respectively. For the example of FIG. 36, each portion may be a series of frames 3610, 3612, 3614, 3616, 3618, 3620 recorded from a viewpoint at times T1, T2, and T3.

When a recorded multi-view (e.g., 360-degree) content presentation process 3600 begins at T1, the viewers point-of-view may be initialized to be frame (or portion) 2 (3604), an area depicting a tagged object of interest. Because multiple objects of interest are present, the viewer's point-of-view may switch between watching the woman (viewpoint B) and watching the man (viewpoint A) and back to watching the woman. The point-of-view switching results in a time-sequence of perspectives having important objects present. For some embodiments of the example presentation process 3600, if the time of the recording is greater than a threshold time, the effective eye tracking position of the videographer is frame 2 (3604) at time T1, frame 1 (3606) at time T2, and frame 2 (3608) at time T3.

Figure 37A:
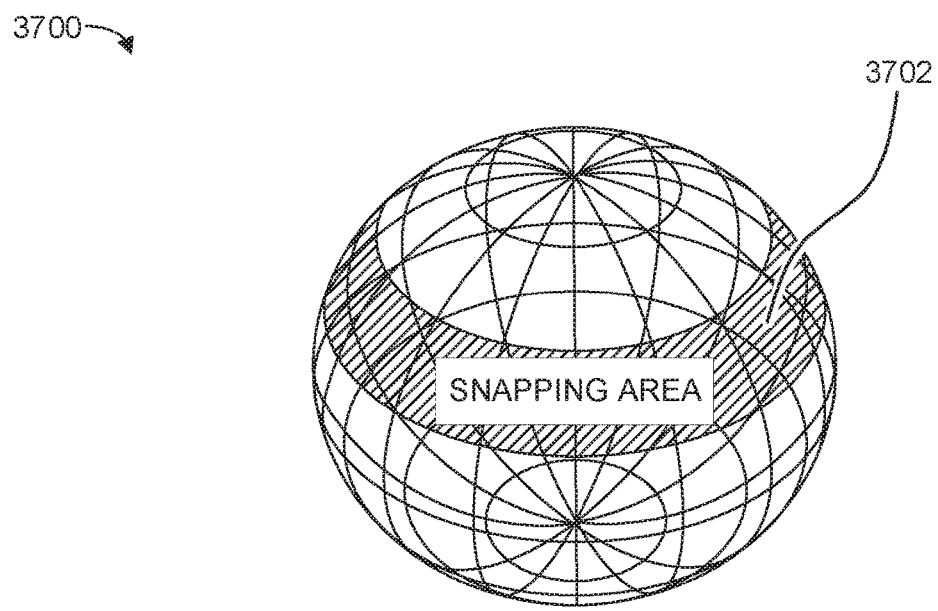
FIGS. 37A and 37B are illustration diagrams showing a first example snapping effect area according to some embodiments.
Figure 37B:
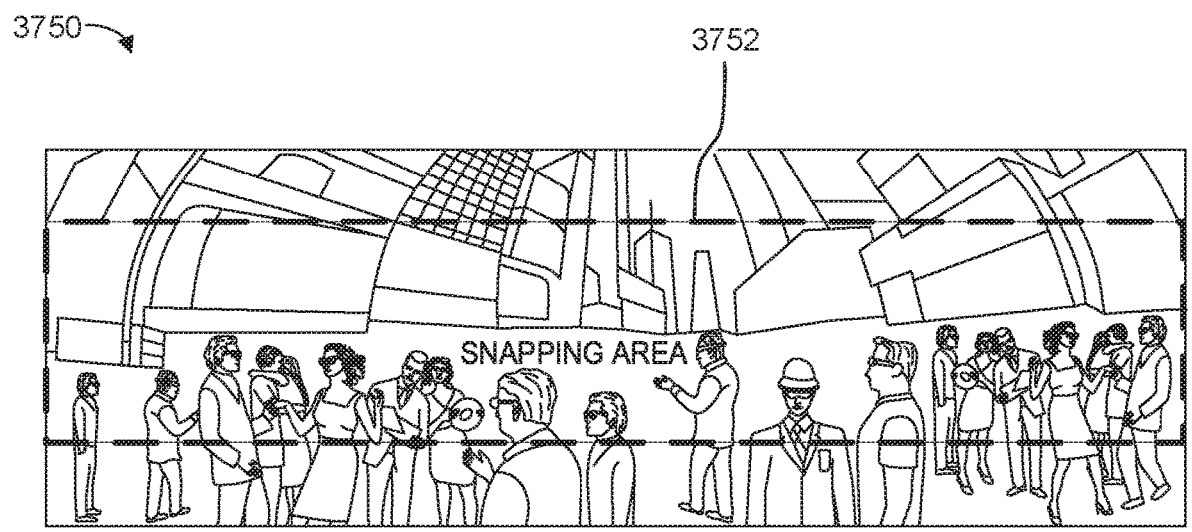

FIGS. 37A and 37B are illustration diagrams showing a first example snapping effect area according to some embodiments. A VR content sphere 3700 may include a snapping area 3702, 3752 and non-snapping (or regular) areas. The snapping area 3702, 3752 (in this example, a ring-like shape) may be determined based on the locations of important objects within the visual data. For some embodiments, a viewpoint-path may move along (or within) a snapping area. In some embodiments, as seen in FIG. 37B, visual guidance of the snapping area 3752 may be overlaid over VR content 3750. For some embodiments, if the user attempts to change the view to an area outside the snapping area (dashed line) 3752, the display may snap back to the view shown in FIG. 37B.

Figure 38A:
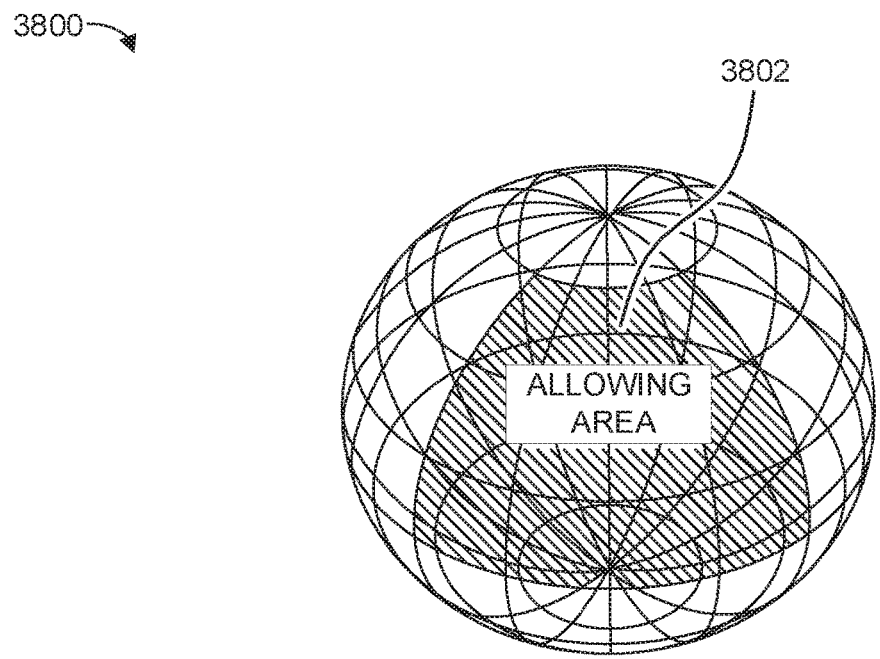
FIGS. 38A and 38B are illustration diagrams showing a second example snapping effect area according to some embodiments.
Figure 38B:

FIGS. 38A and 38B are illustration diagrams showing a second example snapping effect area according to some embodiments. A VR content sphere 3800 may include an allowing area 3802, which allows the snapping effect, and a non-snapping (or regular) area. The allowing area 3802 (in this example, a rectangle projected onto a sphere) may be determined based on the locations of important objects within the visual data. For some embodiments, properties (e.g., size, shape, depth, or resolution) of the allowing area 3802, 3852 may be determined based on factors such as a watching time, a viewer's profile (e.g. gender, age), a viewer's intent, or pay-per-view status. In some embodiments, as seen in FIG. 38B, visual guidance of the allowing area 3852 may be overlaid over VR content 3850. For some embodiments, if the user attempts to change the view to an area outside the allowing area 3852, the display may change back to the view shown in FIG. 38B.

Figure 39:
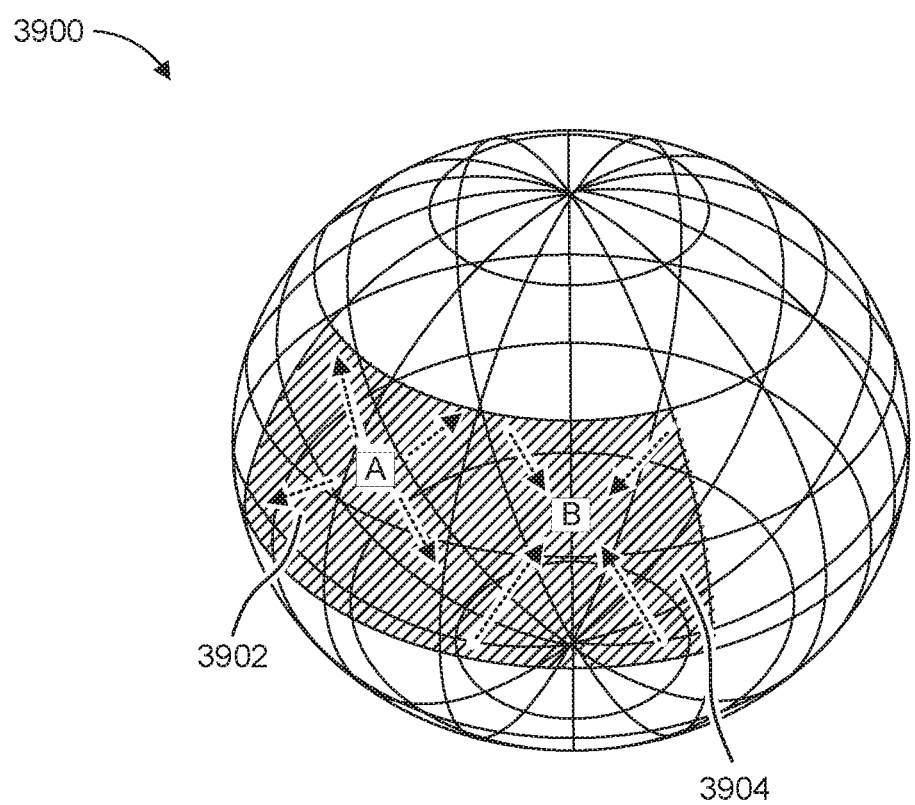
FIG. 39 is a schematic perspective view illustrating an example of magnetic effect areas according to some embodiments.

FIG. 39 is a schematic perspective view illustrating an example of magnetic effect areas according to some embodiments. A magnetic effect may include zooming into a first area 3902 and zooming out of a second area 3904. In FIG. 39, area A is a zoom-in area 3902 and area B is a zoom-out area 3904. Zoom-in and zoom-out areas may be determined based on the locations of important objects. For some embodiments, after a threshold (or predetermined) time period has expired, the effects applied to the multi-view (e.g., 360-degree) content may return to their original levels (or non-magnetic effects, for example). To emphasize a certain portion of the multi-view (e.g., 360-degree) content, for some embodiments, properties of the magnetic effect may be adjusted (e.g., properties such as zoom strength, zoom area, zoom-in ratio, or zoom-out ratio).

Figure 40A:
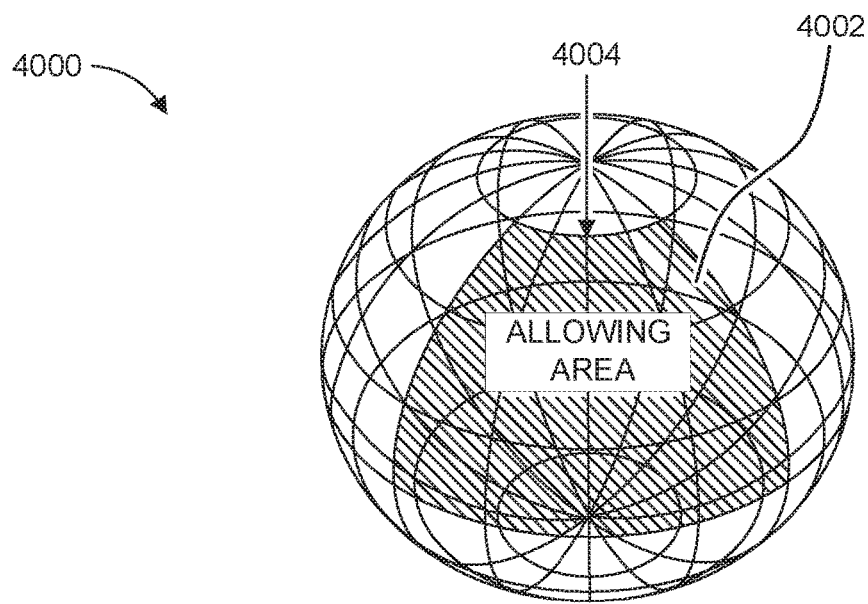
FIGS. 40A and 40B are illustration diagrams showing an example bouncing effect according to some embodiments.
Figure 40B:
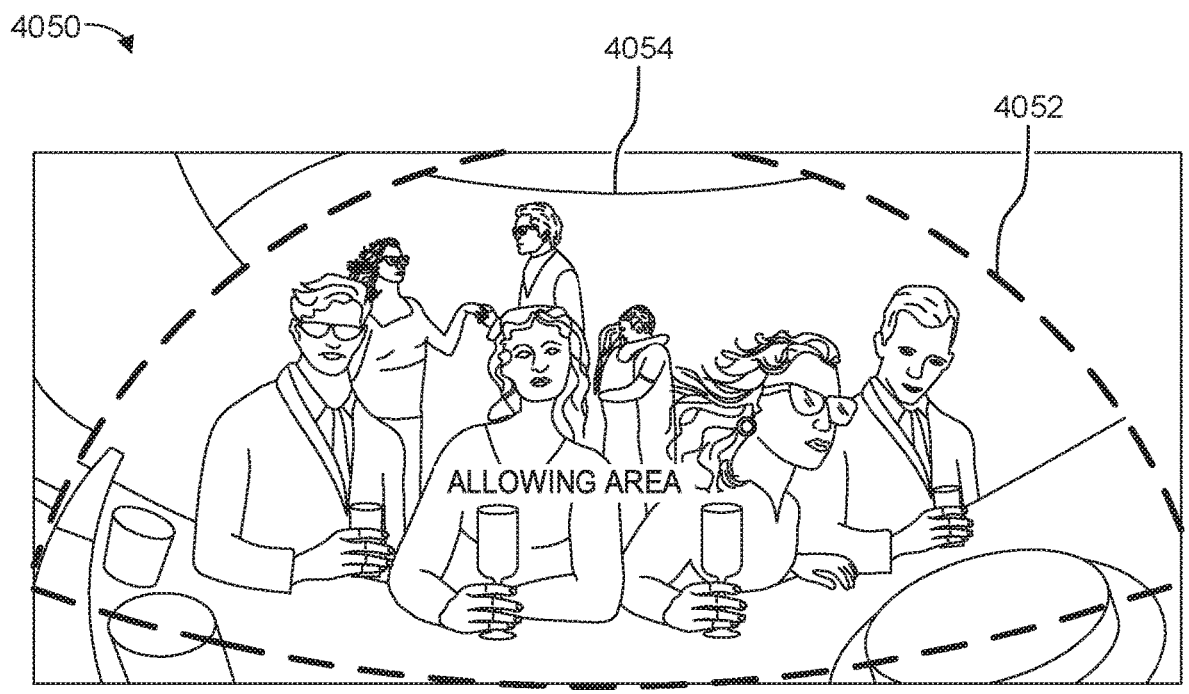

FIGS. 40A and 40B are illustration diagrams showing an example bouncing effect according to some embodiments. A processor may provide bounce back/rebound effects (e.g., auditory, tactile, or visual) at a boundary line 4004, 4054 between an allowed area 4002, 4052 and a non-allowed area. At first, a viewer may not view content within a non-allowed area. The non-allowed area may be unlocked by making a payment (or paid admission) or through user identification and access verification (e.g., a password or biometric information). After the non-allowed area is unlocked, the bouncing effects at the boundary line 4004, 4054 may be disabled.

For example, user A may view content (or move) only in the allowed area due to his/her age. In the allowed area, user A experiences a snapping or bouncing effect when attempting to look past the area's edge. If parents input user identification information, user A may move into the non-allowed area. In FIGS. 40A and 40B, an unauthorized viewer may be unable to look away from a group of people. A snap or bounce back effect prevents the viewer from seeing past the area boundary 4004, 4054.

FIG. 41 is a process diagram illustrating an example for handling restricted viewpoints according to some embodiments. FIG. 41 shows a process 4100 that changes the starting viewpoint 4106 from an original (or restricted) starting viewpoint 4102 and a changed starting viewpoint 4104. Some embodiments may use a restricting effect that prevents a viewer from seeing defined areas without special access. Restrictions may be based on age, (e.g., restrictions to adult content), parental controls, managed privacy settings, environmental properties of the viewing space (e.g., room size, public area, population density), and more factors can be listed as well. If a default starting viewpoint is restricted and a viewer lacks access, the starting viewpoint may be changed to a different starting viewpoint. The different starting viewpoint may include only the allowable area for the viewer.

FIG. 42 is a process diagram illustrating an example for adjusting a viewers starting viewpoint according to some embodiments. FIG. 42 shows an example process 4200 that compares an original starting viewpoint and a changed starting viewpoint. An object displayed in the multi-view (e.g., 360-degree) content (e.g., a car) may be determined to be important based on the videographers preference, the viewers intent (e.g., learning, shopping, relaxing, entertainment, gaming), the viewers profile information (e.g., gender, age), and information about the viewer's behavior/activities on social media.

The first starting viewpoint 4202 may be changed 4206 to the second viewpoint 4204 to emphasize the important object. To further emphasize an object, output modalities for the important object may be adjusted accordingly. If there are multiple conflicting factors, at least one of the starting viewpoint and one viewpoint-path may be adjusted based on the viewer's personal information. Also, at least one of the viewpoint-path and output modalities at the viewpoint may be changed based on measured reaction information (e.g., brain signal, facial expression, eye direction, and pulse) during playback. For example, if the viewer pays to access a certain restricted area or a certain visual object, the traversable area in the multi-view (e.g., 360-degree) content may be enlarged by a predetermined amount. For some embodiments, a visual object may be emphasized (such as by increasing the object's size or adding highlighting to the object), such as for an advertisement.

Figure 43:
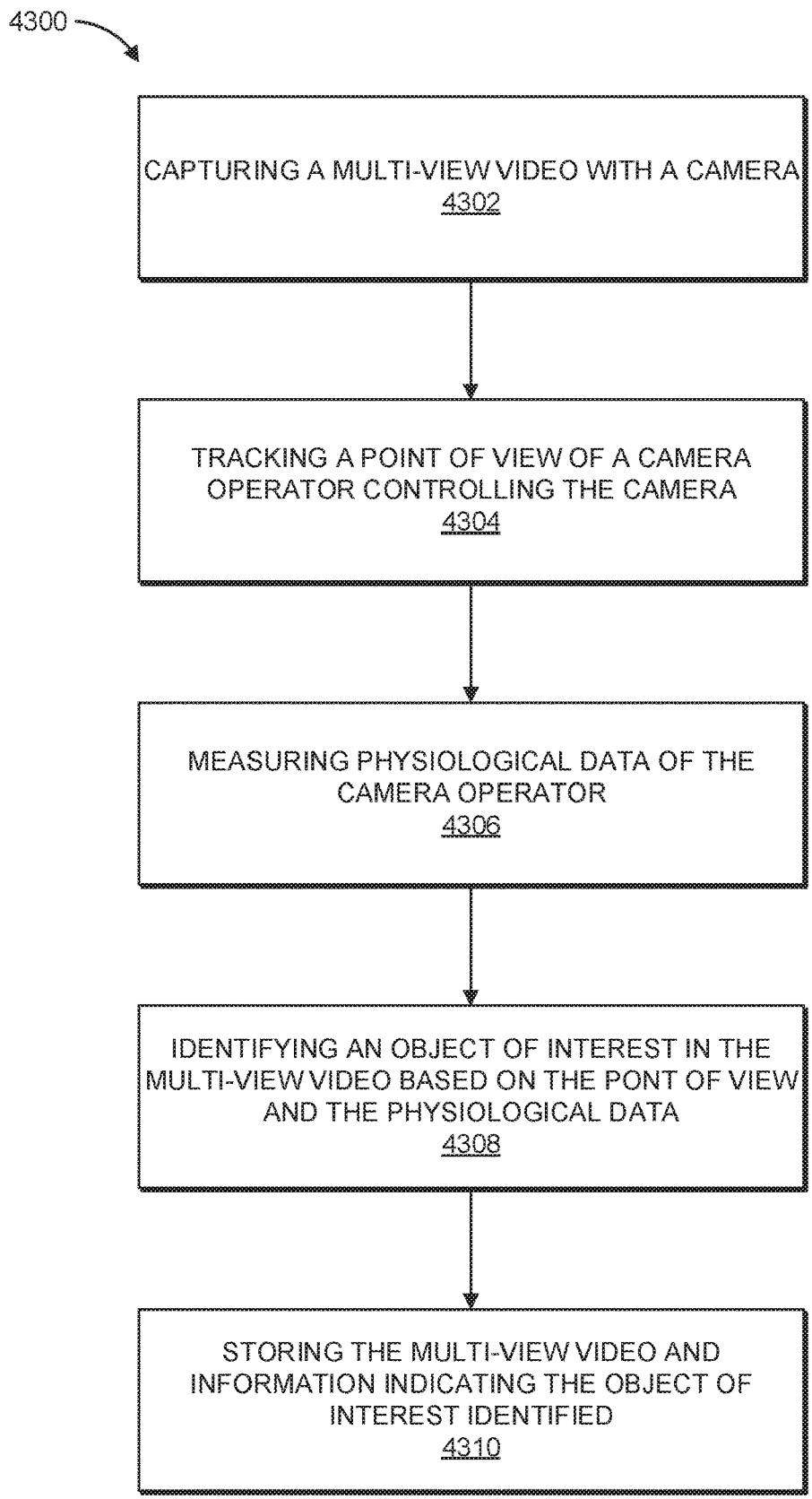
FIG. 43 is a flowchart illustrating an example process for tracking a camera operator's point of view and identifying an object of interest in a multi-view video according to some embodiments.

FIG. 43 is a flowchart illustrating an example process for tracking a camera operator's point of view and identifying an object of interest in a multi-view video according to some embodiments. For some embodiments, a method 4300 may include capturing 4302 a multi-view video with a camera. The method 4300 may further include tracking 4304 a point of view of a camera operator controlling the camera. The method 4300 may further include measuring 4306 physiological data of the camera operator. The method 4300 may further include identifying 4308 an object of interest in the multi-view video based on the point of view and the physiological data. The method 4300 may further include storing 4310 the multi-view video and information indicating the object of interest identified.

FIG. 44 is a flowchart illustrating an example process for implementing a display effect based on the point of view of the camera operator and the viewer according to some embodiments. For some embodiments, a method 4400 may include displaying 4402 a portion of a multi-view video of a viewable display of a head-mounted device (HMD) worn by a user, wherein the viewable display of the HMD defines a point of view of the user with respect to the multi-view video. The method 4400 may further include receiving 4404 information regarding a point of view of a camera operator other than the user and an object of interest in the multi-view video, the point of view of the camera operator being with respect to the multi-view video, and the object of interest is identified as being within the point of view of the camera operator and is indicated as being of interest to the camera operator. The method 4400 may further include responsive to determining 4406 that the point of view of the user as defined by the viewable display of the HMD overlaps with the point of view of the camera operator, rendering the object of interest in the portion of the multi-view video displayed to the user and within the point of view of the user. The method 4400 may further include determining 4408 that the point of view of the user as defined by the viewable display of the HMD no longer overlaps with the point of view of the camera operator. The method 4400 may further include responsively implementing 4410 a display effect to continue rendering the object of interest within the point of view of the user even as the point of view of the user as defined by the viewable display of the HMD no longer overlaps with the point of view of the camera operator.

Figure 45:
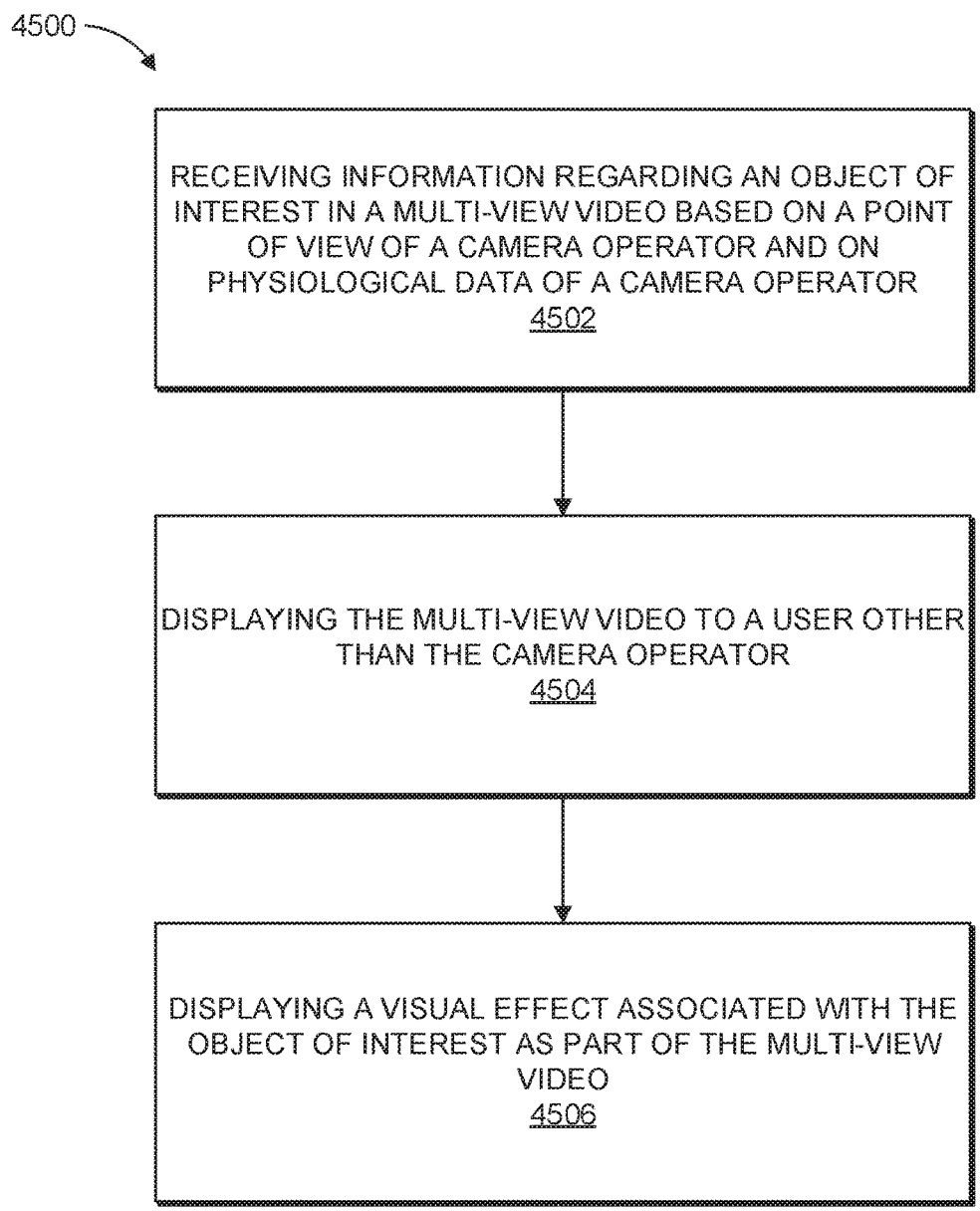
FIG. 45 is a flowchart illustrating an example process for displaying a visual effect associated with an object of interest according to some embodiments.

FIG. 45 is a flowchart illustrating an example process for displaying a visual effect associated with an object of interest according to some embodiments. For some embodiments, a method 4500 may include receiving 4502 information regarding an object of interest in a multi-view video based on a point of view of a camera operator and on physiological data of a camera operator. For some embodiments, the physiological data and the point of view of the camera operator may be recorded at the time that the camera operator controls the recording of the multi-view video. The method 4500 may include displaying 4504 the multi-view video to a user other than the camera operator (such as an end user/viewer). The method 4500 may include displaying 4506 a visual effect associated with the object of interest as part of the multi-view video.

While the methods and systems in accordance with some embodiments are discussed in the context of virtual reality (VR), some embodiments may be applied to mixed reality (MR)/augmented reality (AR) contexts as well. Although the term "head mounted display (HMD)" is used herein in accordance with some embodiments, some embodiments may be applied to a wearable device (which may or may not be attached to the head) capable of, e.g., VR, AR, and/or MR for some embodiments. While the term "videographer" is used herein in accordance with some embodiments, in some embodiments, a videographer may include, e.g., a camera operator, a director, or a remote operator of one or more cameras. For some embodiments, a videographer may wear one or more cameras. For some embodiments, a videographer may be at a location remote from the one or more video cameras. Although the term "level of interest" of an object is used herein in accordance with some embodiments, "level of importance" of an object may be used for some embodiments. Although the term "object of interest" is used herein in accordance with some embodiments, the terms "important object," "important content," and "important virtual object" may be used for some embodiments.

The emulation devices may be designed to implement one or more tests of other devices in a lab environment and/or in an operator network environment. For example, the one or more emulation devices may perform the one or more, or all, functions while being fully or partially implemented and/or deployed as part of a wired and/or wireless communication network in order to test other devices within the communication network. The one or more emulation devices may perform the one or more, or all, functions while being temporarily implemented/deployed as part of a wired and/or wireless communication network. The emulation device may be directly coupled to another device for purposes of testing and/or may performing testing using over-the-air wireless communications.

The one or more emulation devices may perform the one or more, including all, functions while not being implemented/deployed as part of a wired and/or wireless communication network. For example, the emulation devices may be utilized in a testing scenario in a testing laboratory and/or a non-deployed (e.g., testing) wired and/or wireless communication network in order to implement testing of one or more components. The one or more emulation devices may be test equipment. Direct RF coupling and/or wireless communications via RF circuitry (e.g., which may include one or more antennas) may be used by the emulation devices to transmit and/or receive data.

Some embodiments of a method may include: capturing a multi-view video with a camera; tracking a point of view of a camera operator controlling the camera; measuring physiological data of the camera operator; identifying an object of interest in the multi-view video based on the point of view and the physiological data; and storing the multi-view video and information indicating the object of interest identified.

For some embodiments, a method may further include: displaying the multi-view video; and displaying a visual effect based on at least one of the point of view of the camera operator and the physiological data of the camera operator.

For some embodiments, a method may further include: rendering the multi-view video to emphasize the object of interest; and displaying the rendered multi-view video.

For some embodiments, rendering the multi-view video to emphasize the object of interest may include: identifying a first portion of the multi-view video with the object of interest; identifying a second portion of the multi-view video without the object of interest; reducing a data size of the second portion of the multi-view video; and rendering the first portion of the multi-view video and the reduced data size second portion of the multi-view video.

For some embodiments, a method may further include: matching the object of interest with an emotional state based on the physiological data; and displaying a visual effect for the object of interest based on the matched emotional state.

For some embodiments, a method may further include: determining a portion of the multi-view video containing the object of interest; selecting a portion of the physiological data associated with the portion of the multi-view video containing the object of interest; and displaying a visual effect based on the selected portion of the physiological data.

For some embodiments, a method may further include displaying a visual effect of the object of interest based on a comparison of a point of view of a viewer of the multi-view video with a point of view of the camera operator.

For some embodiments, a method may further include: comparing a point of view (POV) of the camera operator with a POV of a viewer of the multi-view video; and determining an amount of overlap between the POV of the camera operator and the POV of the viewer.

For some embodiments, physiological data may include measurements of at least one of a pupil size of the camera operator, a pulse rate of the camera operator, and a motion of the camera operator.

For some embodiments, a method may further include: displaying the multi-view video; determining a point of view (POV) overlap as an amount of area overlap between a POV of the camera operator and a POV of a viewer of the multi-view video; setting a visual effect intensity proportional to the POV overlap; and displaying a visual effect with an intensity equal to the visual effect intensity.

For some embodiments, a method may further include setting the visual effect based on an overall emotional state of the camera operator and a characteristic identified with the object of interest.

For some embodiments, a method may further include responsive to detecting the object of interest in the POV of the viewer, increasing the visual effect intensity.

For some embodiments, a method may further include: displaying the multi-view video to be synchronous with a head movement of a viewer of the multi-view video; and responsive to detecting an alignment of the POV of the viewer and the POV of the camera operator, displaying a visual effect for an emotional state associated with the object of interest.

For some embodiments, a method may further include: displaying the multi-view video to be synchronous with a head movement of a viewer of the multi-view video; and responsive to detecting a proximity between a point of view (POV) of the viewer and the POV of the camera operator, displaying a visual effect indicating the proximity between the POV of the viewer and the POV of the camera operator.

For some embodiments, identifying the object of interest in the multi-view video based on the point of view and the physiological data may include: identifying a plurality of objects in the multi-view video; determining, for each of the plurality of objects, a sustaining time equal to a length of time that the point of view of the camera operator points to the respective object; determining, for each of the plurality of objects, an object frequency equal to a frequency of times that the point of view of the camera operator points to the respective object; associating, for each of the plurality of objects, a portion of the physiological data to the respective object; and determining, for each of the plurality of objects, a level of interest based on the sustaining time, the object frequency, and the portion of the physiological data for the respective object.

For some embodiments, tracking the point of view of the camera operator may track the eye position of the camera operator.

For some embodiments, tracking the point of view of the camera operator may include: capturing an image of at least one eye of the camera operator; and determining the eye direction of the camera operator using the image of at least one eye of the camera operator.

For some embodiments, a method may further include: presenting an effect based on at least one of the point of view of the camera operator and the physiological data of the camera operator, wherein the effect may include at least one of a sonic effect and a haptic effect.

For some embodiments, the multi-view video may include a 360-degree video.

Some embodiments of an apparatus may include: a processor; and a non-transitory computer-readable medium storing instructions that are operative, when executed by the processor, to perform a method described above.

For some embodiments, an apparatus may further include: a gaze-tracking sensor; a camera; a physiological sensor; and a display.

For some embodiments, an apparatus may further include: a point of view comparison module; an emotion estimation module; an emotion tagging module; and a memory storage device.

Some embodiments of a method may include: identifying an object of interest in a multi-view video based on a point of view and physiological data of a camera operator; displaying the multi-view video; and displaying a visual effect associated with the object of interest.

Some embodiments of a method may include: capturing a multi-view video with a multi-view camera; tracking a view direction and a point of view of a camera operator controlling the camera using an eye tracker mounted on the camera; measuring physiological data of the camera operator; identifying an object of interest in the multi-view video based on the view direction and the physiological data, wherein the object of interest is within the point of view of the camera operator; displaying a portion of the multi-view video on a viewable display of a head-mounted device (HMD) worn by a user other than the camera operator, wherein the viewable display of the HMD defines a point of view of the user; rendering the identified object of interest in the portion of the multi-view video displayed to the user and within the point of view of the user when the point of the view of the user is determined to overlap with the point of view of the camera operator; and implementing a display effect to continue rendering the identified object of interest within the point of view of the user even when the point of the view user no longer overlaps with the point of view of the camera operator.

Some embodiments of an apparatus may include: a processor; and a non-transitory computer-readable medium storing instructions that are operative, when executed by the processor, to perform a method listed above.

For some embodiments, an apparatus may further include: a gaze-tracking sensor; a camera; a physiological sensor; and a display.

Some embodiments of a method may include: displaying a portion of a multi-view video on a viewable display of a head-mounted device (HMD) worn by a user, wherein the viewable display of the HMD defines a point of view of the user with respect to the multi-view video; receiving information regarding a point of view of a camera operator other than the user and an object of interest in the multi-view video, the point of view of the camera operator being with respect to the multi-view video, and the object of interest is identified as being within the point of view of the camera operator and is indicated as being of interest to the camera operator; responsive to determining that the point of view of the user as defined by the viewable display of the HMD overlaps with the point of view of the camera operator, rendering the object of interest in the portion of the multi-view video displayed to the user and within the point of view of the user; determining that the point of view of the user as defined by the viewable display of the HMD no longer overlaps with the point of view of the camera operator; and responsively implementing a display effect to continue rendering the object of interest within the point of view of the user even as the point of view of the user as defined by the viewable display of the HMD no longer overlaps with the point of view of the camera operator.

For some embodiments, a method may further include: measuring physiological data of the camera operator; and tracking eye position of the camera operator, wherein the object of interest may be identified as being within the point of view of the camera operator and may be indicated as being of interest to the camera operator based on the physiological data and the eye position of the camera operator.

Some embodiments of an apparatus may include: a processor; and a non-transitory computer-readable medium storing instructions that are operative, when executed by the processor, to perform a method listed above.

For some embodiments, an apparatus may further include: a gaze-tracking sensor; a camera; a physiological sensor; and a display.

Some embodiments of a method may include: recording contextually enhanced 360-degree video, wherein recording contextually enhanced 360-degree video may include: capturing data depicting a 360-degree field of view using a first camera, tracking eye movements of a videographer using a second camera, and measuring physiological indicators of the videographer using sensors; identifying an object of interest in frames of the recorded 360-degree video based on the tracked eye movements; rendering the recorded 360-degree video to emphasize frames including the identified object of interest; and during playback of the rendered 360-degree video, applying real-time visual effects to the rendered 360-degree video based on the tracked eye movements and the measured physiological indicators.

For some embodiments, the first camera may be a 360-degree video camera.

For some embodiments, tracking eye movements may include pupil tracking.

For some embodiments, tracking eye movements may include iris tracking.

For some embodiments, tracking eye movements may include object model tracking.

For some embodiments, tracking eye movements may include glint tracking.

For some embodiments, physiological indicators may include at least one of a heartrate, a galvanic skin response, EEG data, ECG data, EMG data.

For some embodiments, sensors may be embedded in a HMD.

For some embodiments, sensors may be embedded in a wearable device that may be wirelessly coupled to a HMD.

For some embodiments, identifying the object of interest in frames of the recorded 360-degree video may be further based on the measured physiological indicators.

For some embodiments, a method may further include tagging objects of interest with estimated emotional states during recording so that emotional indicators and effects can be provided to a viewer during playback.

For some embodiments, rendering the recorded 360-degree video to emphasize frames including the identified object of interest comprises enlarging the identified object of interest.

For some embodiments, rendering the recorded 360-degree video to emphasize frames including the identified object of interest may include shrinking and merging frames that may be deemed unimportant.

For some embodiments, visual effects to the rendered 360-degree video may include zoom effects, snap effects, bounce effects, restriction effects, brightness effects, magnetic effects, friction effects, and viewpoint trajectory effects.

For some embodiments, the applied visual effect intensity may be commensurate with an overlap area of a videographer's and a viewers respective points-of-view.

For some embodiments, a method may further include providing indications of a videographer's emotional state based on the sensor data and an object-attribute analysis.

For some embodiments, a method may be carried out by a HMD.

Some embodiments of a method may include: rendering 360-degree content to be in sync with a content viewer's head movement; responsive to detecting proximity between the content viewer's POV and the recorded videographer's POV, providing indicating effects in the viewers current field of view; and responsive to detecting content viewers POV fully aligning with the recorded videographer's POV, providing emotional effects associated with objects that were sensed as important to the videographer.

For some embodiments, indicating effects may be provided towards contextually important objects to bias a current user's POV towards the videographer's recorded POV.

For some embodiments, indicating effect intensity may be increased in proportion to a matched area between a current users POV and the videographer's recorded POV containing a contextually important object.

For some embodiments, emotional effects may be based on (i) the videographer's overall emotional state using the measured sensor values, as well as (ii) identified characteristics of the important object.

Some embodiments of an apparatus may include: a sensor module; a gaze-tracking module; a video capture unit; a display; a recorded-emotion-indicator module; and a processor, communication hub, and data storage containing instruction executable by the processor for carrying out a set of tasks, the set of tasks may include: recording new contextually-enhanced 360-degree video with the sensor module, the gaze-tracking module, and the video capture module; and displaying recorded contextually-enhanced 360-degree video with the display and indicating emotional data using the recorded-emotion-indicator module.

For some embodiments, an apparatus may be embodied as a HMD.

For some embodiments, an apparatus may further include a VR content creator and storage, wherein: the VR content creator may include a POV comparison unit, an emotion estimator, and an emotion tagging unit, and may be configured to generate contextually-enhanced 360-degree video from 360-degree video, eye tracking data, and sensor data; and the storage may include the viewer's personal information, VR object attributes, and an emotion data look-up table used by the VR content creator to generate the contextually-enhanced 360-degree video.

For some embodiments, an apparatus may be embodied as a server.

For some embodiments, a 360 degree/panoramic content/video may be recorded and captured for a viewer by a videographer (e.g., a camera operator).

For some embodiments, the camera operator's eye may be tracked.

For some embodiments, a biometric sensor value (heart rate/EEG/ECG) and/or motion sensor value may be measured related to the camera operator.

For some embodiments, the objects which are contextually important to the camera operator may be determined.

For some embodiments, the objects which are contextually important to the camera operator may be determined based on eye tracking and/or measured sensor value.

For some embodiments, the camera operator's POV may be stored against the determined contextually important objects.

For some embodiments, the camera operator's overall emotional state may be associated with the determined contextually important objects in the determined POV.

For some embodiments, the overall emotional state may be determined based on measured sensor value in certain period of time in view of certain objects in camera operator's POV.

For some embodiments, the 360-degree content may be rendered for the viewer.

For some embodiments, proximity between content viewers POV and the recorded POV by camera operator may be detected.

For some embodiments, indicating effects a may be re provided in the field of view responsive to the detection of proximity between the content viewers POV and the recorded POV by a camera operator.

For some embodiments, synthesized effects (such as friction, vibration, zoom, snap, brightness, sound, haptics playback, and heart rate) may be provided if the content viewers POV matches the recorded POV of the camera operator.

For some embodiments, synthesized effects (such as friction, vibration, zoom, snap, brightness, sound, haptics playback, and heart rate) may be provided in the current field of view onto contextually important objects to the camera operator.

Some embodiments of a method may include creating the camera operator's context aware 360-degree content for a viewer of content.

Some embodiments of a method may include determining the objects that are important for the camera operator.

Some embodiments of a method may include tracking a camera operator's eye, which may include: determining frequency of blink and determining duration of gaze.

Some embodiments of a method may include utilizing values from biometric sensor and motion sensor attached to the camera operator, which may include spike or increase of heart rate and acceleration.

Some embodiments of a method may include calculating a camera operator's overall emotional state based on each measured sensor value in certain period of time in view of certain objects in the camera operator's POV.

Some embodiments of a method may include correlating the camera operator's overall emotional state against the determined contextually important objects in the determined POV.

Some embodiments of a method may include presenting the content captured by the camera operator to the viewer.

Some embodiments of a method may include presenting the content to the viewer based upon the movements of the viewer.

Some embodiments of a method may include comparing the viewer's POV and the camera operator's POV.

Some embodiments of a method may include providing indicating effects accordingly in the current field of view if closeness in the POV is detected.

Some embodiments of a method may include providing effects, such as friction, vibration, zoom, snap, brightness, sound, and haptic effects, onto the objects which were important for the camera operator Although features and elements are described above in particular combinations, one of ordinary skill in the art will appreciate that each feature or element can be used alone or in any combination with the other features and elements. One of ordinary skill in the art appreciates that various modifications and changes can be made without departing from the scope of the invention as set forth in the claims below. In the foregoing specification, specific embodiments have been described. Accordingly, the specification and figures are to be regarded in an illustrative rather than a restrictive sense, and all such modifications are intended to be included within the scope of present teachings.

Moreover, in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way but may also be configured in ways that are not listed.

Some embodiments may be comprised of one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions may be implemented by a state machine that has no stored program instructions, or in one or more application specific integrated circuits (ASICs), in which each function or some combinations of certain of the functions are implemented as custom logic. A combination of the two functions may be used for some embodiments.

Accordingly, some embodiments, or portions thereof, may combine one or more processing devices with one or more software components (e.g., program code, firmware, resident software, micro-code, etc.) stored in a tangible computer-readable memory device, which in combination from a specifically configured apparatus that performs the functions as described herein. These combinations that form specially programmed devices may be generally referred to herein "modules". The software component portions of the modules may be written in any computer language and may be a portion of a monolithic code base or may be developed in more discrete code portions such as is typical in object-oriented computer languages. In addition, the modules may be distributed across a plurality of computer platforms, servers, terminals, and the like. A given module may even be implemented such that separate processor devices and/or computing hardware platforms perform the described functions.

Moreover, an embodiment can be implemented as a computer-readable storage medium having computer readable code stored thereon for programming a computer (e.g., comprising a processor) to perform a method as described and claimed herein. Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

The Abstract of the Disclosure is provided to allow the reader to quickly ascertain the nature of the technical disclosure. The Abstract is submitted with the understanding that the Abstract will not be used to interpret or limit the scope or meaning of the claims. In addition, in the foregoing Detailed Description, various features are grouped together in various embodiments with the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

Note that various hardware elements of one or more of the described embodiments are referred to as "modules" that carry out (i.e., perform, execute, and the like) various functions that are described herein in connection with the respective modules. As used herein, a module includes hardware (e.g., one or more processors, one or more microprocessors, one or more microcontrollers, one or more microchips, one or more application-specific integrated circuits (ASICs), one or more field programmable gate arrays (FPGAs), one or more memory devices) deemed suitable by those of skill in the relevant art for a given implementation. Each described module also may include instructions executable for carrying out the one or more functions described as being implemented by the respective module, and those instructions may take the form of or include hardware (or hardwired) instructions, firmware instructions, software instructions, and/or the like, and may be stored in any suitable non-transitory computer-readable medium or media, such as commonly referred to as RAM, ROM, etc.

Although features and elements are described above in particular combinations, one of ordinary skill in the art will appreciate that each feature or element may be used alone or in any combination with the other features and elements. In addition, the methods described herein may be implemented in a computer program, software, or firmware incorporated in a computer-readable medium for execution by a computer or processor. Examples of computer-readable storage media include, but are not limited to, a read only memory (ROM), a random-access memory (RAM), a register, cache memory, semiconductor memory devices, magnetic media such as internal hard disks and removable disks, magneto-optical media, and optical media such as CD-ROM disks, and digital versatile disks (DVDs). A processor in association with software may be used to implement a radio frequency transceiver for use in a WTRU, UE, terminal, base station, RNC, or any host computer.

What is Claimed:

What is claimed is:

1. A method comprising:
    displaying multi-view video on a head mounted display (HMD) device of a user, the multi-view video associated with a point of view of a camera operator;
    responsive to determining that a point of view of the user overlaps with the point of view of the camera operator, setting an effect intensity as a function of an amount of overlap between the point of view of the camera operator and the point of view of the user,
    wherein the point of view of the user is defined by a viewable display of the HMD device; and
    using an effect, in accordance with the effect intensity, to highlight an object of interest in the displayed multi-view video.

2. The method of claim 1,
    wherein using the effect in accordance with the effect intensity to highlight the object of interest adjusts a brightness of the object of interest, and
    wherein the effect intensity is a brightness level to which the brightness of the object of interest is adjusted.

3. The method of claim 1,
    wherein using the effect in accordance with the effect intensity to highlight the object of interest adjusts a zoom level of the object of interest, and
    wherein the effect intensity is the zoom level to which the object of interest is adjusted.

4. The method of claim 1,
    wherein using the effect in accordance with the effect intensity to highlight the object of interest plays a sound, and
    wherein the effect intensity is a volume level at which the sound is played.

5. The method of claim 1,
    wherein using the effect in accordance with the effect intensity to highlight the object of interest causes a haptic module to vibrate, and
    wherein the effect intensity is an intensity at which the haptic module vibrates.

6. The method of claim 1, further comprising determining the object of interest based on eye tracking of the camera operator at a time of capture of the multi-view video.

7. The method of claim 1, further comprising determining the object of interest based on physiological sensor information recorded from the camera operator at a time of capture of the multi-view video.

8. The method of claim 1, further comprising:
    capturing the multi-view video with a camera;
    tracking the point of view of the camera operator;
    measuring physiological data of the camera operator; and
    identifying the object of interest in the multi-view video based on the point of view of the camera operator and the physiological data of the camera operator.

9. The method of claim 1, further comprising:
    comparing the point of view of the camera operator with the point of view of the user; and
    determining the amount of overlap that the point of view of the user overlaps with the point of view of the camera operator.

10. The method of claim 1, further comprising:
    responsive to detecting a proximity between the point of view of the user and the point of view of the camera operator, displaying a visual effect indicating the proximity between the point of view of the user and the point of view of the camera operator,
    wherein displaying the multi-view video comprises displaying the multi-view video to be synchronous with a head movement of the user.

11. The method of claim 1, wherein the effect has an intensity equal to the effect intensity.

12. The method of claim 1, further comprising determining the point of view of the user.

13. The method of claim 1, further comprising determining whether the point of view of the user overlaps with the point of view of the camera operator.

14. The method of claim 1, wherein the object of interest is identified as being within the point of view of the camera operator and is indicated as being of interest to the camera operator.

15. The method of claim 1, wherein setting the effect intensity as the function of the amount of overlap between the point of view of the camera operator and the point of view of the user comprises setting the effect intensity based proportionally on the amount of overlap between the point of view of the camera operator and the point of view of the user.

16. An apparatus comprising:
    a processor; and
    a non-transitory computer-readable medium storing instructions that are operative, when executed by the processor, to cause the apparatus to:
        display multi-view video on a head mounted display (HMD) device of a user, the multi-view video associated with a point of view of a camera operator;
        responsive to determining that a point of view of the user overlaps with the point of view of the camera operator, set an effect intensity as a function of an amount of overlap between the point of view of the camera operator and the point of view of the user,
        wherein the point of view of the user is defined by a viewable display of the HMD device; and
        use an effect, in accordance with the effect intensity, to highlight an object of interest in the displayed multi-view video.

17. The apparatus of claim 16, further comprising:
a gaze-tracking sensor;
a camera;
a physiological sensor; and
a display.

18. A method comprising:
displaying multi-view video on a head mounted display (HMD) device of a user, the multi-view video associated with a point of view of a camera operator;
rendering, within a point of view of the user and while the point of view of the user overlaps with the point of view of camera operator, as part of the displayed multi-view video, an object of interest identified as being in the point of view of the camera operator, the point of view of the user being defined by a viewable display of the HMD device; and
responsive to determining that the point of view of the user no longer overlaps with the point of view of the camera operator, implementing a display effect to continue rendering the identified object of interest within the point of view of the user.

19. The method of claim 18, further comprising:
receiving information regarding the point of view of the camera operator and the object of interest in the multi-view video, the point of view of the camera operator being with respect to the multi-view video, and the object of interest is indicated as being of interest to the camera operator.

20. The method of claim 19, further comprising:
capturing the multi-view video with a multi-view camera;
tracking a view direction and the point of view of the camera operator controlling the camera using an eye tracker mounted on the camera;
measuring physiological data of the camera operator; and
identifying the object of interest in the multi-view video based on the view direction and the physiological data.

* * * * *